US006525046B1

(12) United States Patent
Cirillo et al.

(10) Patent No.: US 6,525,046 B1
(45) Date of Patent: Feb. 25, 2003

(54) AROMATIC HETEROCYCLIC COMPOUNDS AS ANTIINFLAMMATORY AGENTS

(75) Inventors: Pier Francesco Cirillo, Woodbury, CT (US); Roger Dinallo, Woodbury, CT (US); John Robinson Regan, Larchmont, NY (US); Paul S. Riska, Danbury, CT (US); Alan David Swinamer, Bethel, CT (US); Zhulin Tan, Danbury, CT (US); Brian Andrew Walter, Ridgefield, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/165,372

(22) Filed: Jun. 7, 2002

Related U.S. Application Data

(60) Continuation-in-part of application No. 09/879,776, filed on Jun. 12, 2001, now abandoned, which is a division of application No. 09/484,638, filed on Jan. 18, 2000, now Pat. No. 6,319,921.

(51) Int. Cl.$^7$ .................. A61K 31/5377; A61K 31/541; A61P 19/02; C07D 413/12; C07D 417/12
(52) U.S. Cl. .................. 514/227.8; 514/230.8; 514/236.5; 544/58.2; 544/131; 544/140; 546/275.4; 546/256
(58) Field of Search .................. 544/131, 140, 544/58.2; 546/275.4; 514/227.8, 236.5

(56) References Cited

U.S. PATENT DOCUMENTS

| | | | |
|---|---|---|---|
| 4,105,766 A | 8/1978 | Alexander | |
| 4,435,567 A | 3/1984 | Lugosi et al. | |
| 5,162,360 A | * 11/1992 | Creswell et al. | 514/371 |
| 5,686,455 A | 11/1997 | Adams et al. | |
| 5,739,143 A | 4/1998 | Adams et al. | |
| 5,777,097 A | 7/1998 | Lee et al. | |
| 5,783,664 A | 7/1998 | Lee et al. | |
| 5,859,041 A | 1/1999 | Liverton et al. | |
| 5,869,043 A | 2/1999 | McDonnell et al. | |
| 5,871,934 A | 2/1999 | Lee et al. | |
| 5,916,760 A | 6/1999 | Goeddel et al. | |
| 5,948,885 A | 9/1999 | Stein et al. | |
| 6,242,453 B1 | 6/2001 | Cirillo et al. | |
| 6,319,921 B1 | 11/2001 | Cirillo et al. | |

FOREIGN PATENT DOCUMENTS

| | | |
|---|---|---|
| DE | 293 352 | 8/1991 |
| EP | 0 272 866 | 6/1988 |
| EP | 0 395 144 | 10/1990 |
| EP | 0 418 071 | 3/1991 |
| EP | 0692483 | 1/1996 |
| EP | 0859054 | 8/1998 |
| EP | 0922762 | 6/1999 |
| EP | 0 955 293 | 10/1999 |
| JP | 61228444 | 10/1986 |
| WO | WO 93/24458 | 9/1993 |
| WO | WO 94/18170 | 8/1994 |
| WO | WO 94/22866 | 10/1994 |
| WO | WO 96/25157 | 8/1996 |
| WO | WO 96/40143 | 12/1996 |
| WO | WO 97/16442 | 5/1997 |
| WO | WO 97/22704 | 6/1997 |
| WO | WO 97/33883 | 9/1997 |
| WO | WO 97/35855 | 10/1997 |
| WO | WO 97/35856 | 10/1997 |
| WO | WO 97/44467 | 11/1997 |
| WO | WO 97/47618 | 12/1997 |
| WO | WO 97/48697 | 12/1997 |
| WO | WO 98/07425 | 2/1998 |
| WO | WO 98/15618 | 4/1998 |
| WO | WO 98/27098 | 6/1998 |
| WO | WO 98/52558 | 11/1998 |
| WO | WO 98/52559 | 11/1998 |
| WO | WO 99/00357 | 1/1999 |
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO 99/32463 | 7/1999 |
| WO | WO 99/46244 | 9/1999 |

OTHER PUBLICATIONS

Jeffrey C. Boehm & Jerry L. Adams, New Inhibitors of p38 kinase, Expert Opin. Ther. Patents (2000) 10(1):25–37.
Two novel structural classes of p38 kinase inhibitors; Exp. Opin. Ther. Patents (1999) 9(4) 477–480.
SB 203580, Calbiochem –Cat. No 559389 –Revised May 30, 1997.
Jagadish C. Sircar, et al; Pyrazolo [5,1–b] quinazolin–9 ones: A New Series of Antiallergic Agents, J. Med. Chem. 1981, 24, 735–742.
U.S. patent application Ser. No. 09/503,263 filed Feb. 14, 2000; Zhang, L. et al; Polycyclo Heterocyclic Derivatives as Antiinflammatory Agents.
U.S. patent application Ser. No. 09/611,109 filed Jun. 7, 2000, Zhang, L. et al; Process for Synthesis of Heteroaryl Substituted Urea Compounds Useful as Antiinflammatory Agents.

* cited by examiner

Primary Examiner—Robert W. Ramsuer
(74) Attorney, Agent, or Firm—Robert P. Raymond; Anthony P. Bottino; Alan R. Stempel

(57) ABSTRACT

Disclosed are novel aromatic heterocyclic compounds of the formula(I) wherein $Ar_1, Ar_2, L, Q$ and X are described herein. The compounds are useful in pharmaceutic compositions for treating diseases or pathological conditions involving inflammation such as chronic inflammatory diseases. Also disclosed are processes of making such compounds.

(I)

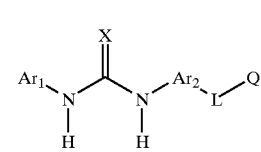

6 Claims, No Drawings

AROMATIC HETEROCYCLIC COMPOUNDS AS ANTIINFLAMMATORY AGENTS

RELATED APPLICATION DATA

This application is a continuation in-part of U.S. application Ser. No. 09/879,776 filed Jul. 12, 2001 now abandoned, which is a divisional of U.S. application Ser. No. 09/484,638 filed Jan. 18, 2000, now U.S. Pat. No. 6,319,921.

TECHNICAL FIELD OF THE INVENTION

This invention relates to novel aromatic heterocyclic compounds of formula (I):

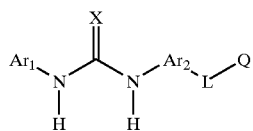

wherein $Ar_1$, $Ar_2$, X, L and Q are defined below, which inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). Studies suggest that inflammatory changes mediated by cytokines may be involved in the pathogenesis of restenosis after percutaneous transluminal coronary angioplasty (PTCA) (Tashiro, H., et al., 2001 March, *Coron. Artery Dis.* 12(2) :107–13). An important and accepted therapeutic approach for potential drug intervention in these diseases is the reduction of proinflammatory cytokines such as TNF (also referred to in its secreted cell-free form as TFNα) and IL-1β. A number of anti-cytokine therapies are currently in clinical trials. Efficacy has been demonstrated with a monoclonal antibody directed against TFNα in a number of autoimmune diseases (Heath, P.,"CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, *Lancet* 349: 521–524). The monoclonal antibody is thought to function by binding to both soluble TFNα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TFNα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrition* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother*. 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner. Res*. 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc. Soc. Exp. Biol. Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment. Pharmacol. Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med. Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin. Exp. Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TFNα and IL-1α are also important mediators of septic shock and associated cardiopulmonary dysfunction, acute respiratory distress syndrome (ARDS) and multiple organ failure. In a study of patients presenting at a hospital with sepsis, a correlation was found between TFNα and IL-6 levels and septic complications (Terregino et al., 2000, *Ann. Emerg. Med.* 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med. Hypotheses* 47, 423). An inhibitor of TNFα production, HU-211, was shown to improve the outcome of closed brain injury in an experimental model (Shohami, et al., 1997, *J. Neuroimmunol.* 72, 169). Atherosclerosis is known to have an inflammatory component and cytokines such as IL-1 and TNF have been suggested to promote the disease. In an animal model an IL-1 receptor antonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J. Resp. & Crit. Care Med.*, 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3–12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by administration of an anti-IL-1 monoclonal antibody before epicutaneous application of an allergen (Muller, et al., 1996, *Am. J. Contact Dermat.* 7, 177). Data obtained from IL-1 knock out mice indicates the critical involvement in fever for this cytokine (Kluger et al., 1998, *Clin. Exp. Pharmacol. Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am. J. Clin. Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am. J. Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevate levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokines Mol. Ther.* 1, 107). Several infectious diseases, such as influenza, indicate IL-6 and IFN alpha as key factors in both symptom formation and in host defense (Hayden, et al., 1998, *J. Clin. Invest.* 101, 643). Overexpression of IL-6 has been implicated in the pathology of a number of diseases including multiple myeloma, rheumatoid arthritis, Castleman's disease, psoriasis and postmenopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J. R. Coll. Physicians Lond* 32, 56). Interferon γ (IFNγ) has been implicated in a number of diseases. It has been associated with increased collagen deposition that is a central histopathological feature of graft-versus-host disease (Parkman, 1998, *Curr. Opin. Hematol.* 5, 22). Following kidney transplantation, a patient was diagnosed with acute myclogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk. Lymphoma.* 19, 173). The development of insulin-dependent diabetes (Type 1) can be correlated with the accumulation in pancreatic islet cells of T-cells producing IFN γ (Ablumunits, et al., 1998, *J. Autoimmun.* 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann. Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl.* 12, 76). Allergic subjects produce mRNA specific for IFN γ following challenge with Vespula venom (Bonay, et al., 1997, *Clin. Exp. Immunol.* 109, 342). The expression of a number of cytokines, including IFN γ has been shown to increase following a delayed type hypersensitivity reaction thus indicating a role for IFN γ in atopic dermatitis (Szepietowski, et al., 1997, *Br. J. Dermatol.* 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am. J. Trop. Med. Hyg.* 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc. Soc. Exp. Biol. Med.* 217, 64). Patients, chronically infected with hepatitis B virus (HBV) can develop cirrhosis. and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin. Immunopathol.* 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J.+Bone Miner Res.* 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon.* 43, 277). IFN γ is required for progression of chronic intestinal inflammation in such diseases as Crohn's disease and inflammatory bowel disease (IBD) presumably through the intermediacy of CD4+ lymphocytes probably of the THI phenotype (Sartor 1996, *Aliment Pharmacol Ther.* 10 Suppl 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et aL, 1998, *Clin Exp Allergy* 28, 74).

WO 01/01986 discloses particular compounds alleged to having the ability to inhibit TNF-alpha. The specific inhibitors disclosed are structurally distinct from the novel compounds disclosed in the present application disclosed hereinbelow. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wemicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF SUMMARY OF THE INVENTION

The work cited above supports the principle that inhibition of cytokine production will be beneficial in the treatment of various disease states.

It is therefore an ect of the invention to provide novel compounds which inhibit the release of inflammatory cytokines such as interleukin-1 and tumor necrosis factor.

It is a further object of the invention to provide methods for treating diseases and pathological conditions involving inflammation such as chronic inflammatory disease.

It is yet a further object of the invention to provide processes of preparation of the above-mentioned novel compounds.

DETAILED DESCRIPTION OF THE INVENTION

The present invention is directed to compounds of the formula (I):

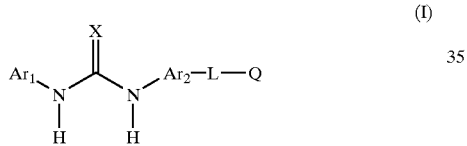

wherein
- $Ar_1$ is a heterocyclic group selected from the group consisting of pyrrole, pyrrolidine, pyrazole, imidazole, oxazole, thiazole, furan and thiophene;
- and wherein $Ar_1$ may be substituted by one or more $R_1$, $R_2$ or $R_3$;
- $Ar_2$ is:
  - phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with one to three $R_2$ groups;
- L, a linking group, is a:
  - $C_{1-10}$ saturated or unsaturated branched or unbranched carbon chain;
  - wherein one or more methylene groups are optionally independently replaced by O, N or S; and
  - wherein said linking group is optionally substituted with 0–2 oxo groups and one or more $C_{1-4}$ branched or unbranched alkyl which may be substituted by one or more halogen atoms;
- Q is selected from the group consisting of:
  a) phenyl, naphthyl, pyridine, pyrimidine, pyridazine, imidazole, benzimidazole, furan, thiophene, pyran, naphthyridine, oxazo[4,5-b] pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups consisting of halogen, $C_{1-6}$ alkyl and $C_{1-6}$ alkoxy;
  b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl;
  c) $C_{1-6}$ alkoxy, secondary or tertiary amine wherein the amino nitrogen is covalently bonded to groups selected from the group consisting of $C_{1-3}$ alkyl and $C_{1-5}$ alkoxyalkyl and phenyl wherein the phenyl ring is optionally substituted with one to two groups consisting of halogen, $C_{1-6}$ alkoxy, hydroxy or mono- or di-($C_{1-3}$ alkyl)amino, $C_{1-6}$ alkyl-S(O)$_r$, phenyl-S(O)$_r$, wherein the phenyl ring is optionally substituted with one to two groups consisting of halogen, $C_{1-6}$ alkoxy, hydroxy or mono- or di-($C_{1-3}$ alkyl)amino;
- $R_1$ is selected from the group consisting of:
  (a) $C_{3-10}$ branched unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, $NH_2C(O)$ and di($C_{1-3}$)alkylaminocarbonyl;
  (b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which may optionally be partially or fully halogenated and which may optionally be substituted with one to three $C_{1-3}$ alkyl groups, or an analog of such cycloalkyl group wherein one to three ring methylene groups are replaced by groups independently selected from O, S, CHOH, >C=O, >C=S and NH;
  (c) $C_{3-10}$ branched alkenyl which may optionally be partially or fully halogenated, and which is optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl and bicycloheptanyl, hydroxy, cyano, $C_{1-3}$ alkyloxy which is optionally partially or fully halogenated, $NH_2C(O)$, mono- or di($C_{1-3}$)alkylaminocarbonyl;

d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups;

e) cyano; and, f) methoxycarbonyl, ethoxycarbonyl and propoxycarbonyl;

$R_2$ is selected from the group consisting of:
a $C_{1-6}$ branched or unbranched alkyl which may optionally be partially or fully halogenated, acetyl, aroyl, $C_{1-4}$ branched or unbranched alkoxy, which may optionally be partially or fully halogenated, halogen, methoxycarbonyl and phenylsulfonyl;

$R_3$ is selected from the group consisting of:
a) a phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl; wherein such phenyl, naphthyl or heterocyclic group is optionally substituted with one to five groups selected from the group consisting of a $C_{1-6}$ branched or unbranched alkyl, phenyl, naphthyl, heterocycle selected from the group hereinabove described, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, hydroxy, cyano, $C_{1-3}$ alkyloxy which may optionally be partially or fully halogenated, phenyloxy, naphthyloxy, hetaryloxy wherein the heterocyclic moiety is selected from the group hereinabove described, nitro, amino, mono- or di-($C_{1-3}$)alkylamino, phenylamino, naphthylamino, heterocyclylamino wherein the heterocyclyl moiety is selected from the group hereinabove described, $NH_2C(O)$, a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-$S(O)_2$, di-($C_{1-3}$)alkylamino-$S(O)_2$, $R_4$—$C_{1-5}$ alkyl, $R_5$—$C_{1-5}$ alkoxy, $R_6$—C(O)—$C_{1-5}$ alkyl and $R_{1-7}$—$C_{1-5}$ alkyl($R_8$)N;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from the group consisting of cylopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from phenyl, naphthyl and heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heterocyclyloxy wherein the heterocyclyl moiety is selected from the group hereinabove described, nitro, amino, mono- or di-($C_{1-3}$)alkylamino, phenylamino, naphthyamino, heterocyclylamino wherein the heterocyclyl moiety is selected from the group hereinabove described, $NH_2C(O)$, a mono- or di-($C_{1-3}$)alkyl aminocarbonyl, $C_{1-4}$ alkyl-OC(O), $C_{1-5}$ alkyl-C(O)—$C_{1-4}$ branched or unbranched alkyl, an amino —$C_{1-5}$ alkyl, mono- or di-($C_{1-3}$)alkylamino-$C_{1-5}$ alkyl, $R_9$—$C_{1-5}$ alkyl, $R_{10}$—$C_{1-5}$ alkoxy, $R_{11}$—C(O)—$C_{1-5}$ alkyl, and $R_{12}$—$C_{1-5}$ alkyl($R_{13}$)N;

c) cycloalkyl selected from the group consisting of cyclopentanyl, cyclohexanyl, cycloheptanyl, bicyclopentanyl, bicyclohexanyl and bicycloheptanyl, which the cycloalkyl may optionally be partially or fully halogenated and which may optionally be substituted with one to three $C_{1-3}$ alkyl groups;

d) $C_{5-7}$ cycloalkenyl, selected from the group consisting of cyclopentenyl, cyclohexenyl, cyclohexadienyl, cycloheptenyl, cycloheptadienyl, bicyclohexenyl and bicycloheptenyl, wherein such cycloalkenyl group may optionally be substituted with one to three $C_{1-3}$ alkyl groups; and e) acetyl, aroyl, alkoxycarbonylalkyl or phenylsulfonyl;

f) $C_{1-6}$ branched or unbranched alkyl which may optionally be partially or fully halogenated;

wherein
or $R_1$ and $R_2$ taken together may optionally form a fused phenyl or pyridinyl ring, each $R_8$, $R_{13}$ is independently selected from the group consisting of:
hydrogen and $C_{1-4}$ branched or unbranched alkyl which may optionally be partially or fully halogenated;

each $R_4$, $R_5$, $R_6$, $R_7$, $R_9$, $R_{10}$, $R_{11}$ and $R_{12}$ is independently selected from the group consisting of:
morpholine, piperidine, piperazine, imidazole and tetrazole;

m=0, 1, 2;
r=0, 1, 2;
t=0, 1, 2;
X=O or S and
physiologically acceptable acids or salts thereof.

A preferred subgeneric aspect of the invention comprises compounds of the formula(I) wherein $Ar_2$ is naphthyl, tetrahydronaphthyl, indanyl or indenyl.

A more preferred subgeneric aspect of the invention comprises compounds of the formula(I) wherein $Ar_2$ is naphthyl.

A yet more preferred subgeneric aspect of the invention comprises compounds of the formula (I), as described in the immediate previous paragraph, wherein:

$Ar_1$ is thiophene or pyrazole;
$Ar_2$ is 1-naphthyl;
L is $C_{1-6}$ saturated or unsaturated branched or unbranched carbon chain
wherein
one or more methylene groups are optionally independently replaced by O,N or S; and
wherein said linking group is optionally substituted with 0–2 oxo groups and one or more $C_{1-4}$ branched or unbranched alkyl which may be substituted by one or more halogen atoms;
$R_1$ is selected from the group consisting of $C_{3-10}$alkyl branched or unbranched, cyclopropyl and cyclohexyl which may optionally be partially or fully halogenated and which may optionally be substituted with one to three $C_{1-3}$ alkyl groups;
$R_3$ is selected from the group consisting of $C_{1-4}$alkyl branched or unbranched, cyclopropyl, cyclopentyl, phenyl, pyridinyl each being optionally substituted as described above and alkoxycarbonylalkyl.

A yet further preferred subgeneric aspect of the invention comprises compounds of the formula (I), as described in the immediate previous paragraph, wherein $Ar_1$ is pyrazole.

A still yet further preferred subgeneric aspect of previous the invention comprises compounds of the formula (I), as described in the immediate paragraph, wherein L is $C_{1-5}$ saturated carbon chain wherein one or more methylene groups are optionally independently replaced by O,N or S; and
wherein said linking group is optionally substituted with 0–2 oxo groups and one or more $C_{1-4}$ branched or unbranched alkyl which may be substituted by one or more halogen atoms;
Particularly preferred embodiments of L are propoxy, ethoxy, methoxy, methyl, propyl, $C_{3-5}$ acetylene or methylamino each being optionally substituted are described herein.

A more particularly preferred embodiment of L is ethoxy optionally substituted.

The following compounds are representative of the compounds of formula(I):

1-[5-tert-Butyl-2-p-tolyl-2H-pyrazol-3-yl]-3-[4-(2-morpholin-4-yl-ethoxy)naphthalen-1-yl]-urea;
1-[5-tert-Butyl-2-p-tolyl-2H-pyrazol-3-yl]-3-[4-(2-(cis-2,6-dimethylmorpholin-4-yl)ethoxy)naphthalen-1-yl]-urea;
1-[5-tert-Butyl-2-p-tolyl-2H-pyrazol-3-yl]-3-[4-(2-(trans-2,6-dimethylmorpholin-4-yl)ethoxy)naphthalen-1-yl]-urea;
1-[5-tert-Butyl-2-p-tolyl-2H-pyrazol-3-yl]-3-[4-(2-(2-(methoxymethyl)morpholin-4-yl)ethoxy)naphthalen-1-yl]-urea;
1-[5-tert-Butyl-2-p-tolyl-2H-pyrazol-3-yl]-3-[4-(2-(morpholin-4-yl)-2-oxoethoxy)naphthalen-1-yl]-urea;
1-[5-tert-Butyl-2-p-tolyl-2H-pyrazol-3-yl]-3-[4-(2-(morpholin-4-yl)-2-methylethoxy)naphthalen-1-yl]-urea;
1-[5-tert-Butyl-2-p-tolyl-2H-pyrazol-3-yl]-3-[4-(2-(morpholin-4-yl)-1-methylethoxy)naphthalen-1-yl]-urea;
1-[5-tert-Butyl-2-p-tolyl-2H-pyrazol-3-yl]-3-[4-(2-thiomorpholin-4-yl-ethoxy)naphthalen-1-yl]-urea;
1-[5-tert-Butyl-2-p-tolyl-2H-pyrazol-3-yl]-3-[4-(2-(1-oxothiomorpholin-4-yl)ethoxy)naphthalen-1-yl]-urea;
1-[5-tert-Butyl-2-p-tolyl-2H-pyrazol-3-yl]-3-[4-(2-morpholin-4-yl-ethoxy)-3-methylnaphthalen-1-yl]-urea;
1-[5-tert-Butyl-2-p-tolyl-2H-pyrazol-3-yl]-3-[4-(2-piperidin-4-yl-ethoxy)naphthalen-1-yl]-urea;
1-[5-tert-Butyl-2-p-tolyl-2H-pyrazol-3-yl]-3-[4-(2-(1-acetylpiperidin-4-yl)ethoxy)naphthalen-1-yl]-urea;
1-[5-tert-Butyl-2-p-tolyl-2H-pyrazol-3-yl]-3-[4-(2-thiazolidin-3-yl-ethoxy)naphthalen-1-yl]-urea;
1-[5-tert-Butyl-2-p-tolyl-2H-pyrazol-3-yl]-3-[4-(2-(morpholin-4-yl-carbonyloxo)ethoxy)naphthalen-1-yl]-urea;
1-[5-tert-Butyl-2-p-tolyl-2H-pyrazol-3-yl]-3-[4-(2-(tetrahydropyran-4-yl)ethoxy)naphthalen-1-yl]-urea;
1-[5-tert-Butyl-2-p-tolyl-2H-pyrazol-3-yl]-3-[4-(2-(N-methyl-2-methoxyethylamino)ethoxy)naphthalen-1-yl]-urea;
1-[5-tert-Butyl-2-p-tolyl-2H-pyrazol-3-yl]-3-[4-(2-(1-oxo-tetrahydrothiophen-3-yl)ethoxy)naphthalen-1-yl]-urea;
1-[5-tert-Butyl-2-p-tolyl-2H-pyrazol-3-yl]-3-[4-(3-mopholin-4-yl-propyl)naphthalen-1-yl]-urea;
1-[5-tert-Butyl-2-p-tolyl-2H-pyrazol-3-yl]-3-[4-(morpholin-4-yl-methyl)naphthalen1-yl]-urea;
1-[5-tert-Butyl-2-p-tolyl-2H-pyrazol-3-yl]-3-[4-(3-thiazolidin-3-yl-propyl)naphthalen1-yl]-urea;
1-[5-tert-Butyl-2-p-tolyl-2H-pyrazol-3-yl]-3-[4-(3-(tetrahydopyran-2-yl-oxy)propyl)naphthalen-1-yl]-urea;
1-[5-tert-Butyl-2-p-tolyl-2H-pyrazol-3-yl]-3-[4-(2-pyridin-4-yl-ethyl)naphthalen-1-yl]-urea;
1-[5-tert-Butyl-2-p-tolyl-2H-pyrazol-3-yl]-3-[4-(2-pyridin-4-yl-ethenyl)naphthalen-1-yl]-urea;
1-[5-tert-Butyl-2-p-tolyl-2H-pyrazol-3-yl]-3-[4-(3-(morpholin-4-yl)propyn1-yl)naphthalen-1-yl]-urea;
1-[5-tert-Butyl-2-p-tolyl-2H-pyrazol-3-yl]-3-[4-(3-(tetrahydropyran-2-yl-oxy)propyn-1-yl)naphthalen-1-yl]-urea;
1-[5-tert-Butyl-2-p-tolyl-2H-pyrazol-3-yl]-3-[4-(3-(methoxymethyloxy)propyn-1-yl)naphthalen-1-yl]-urea;
1-[5-tert-Butyl-2-p-tolyl-2H-pyrazol-3-yl]-3-[4-(3-(morpholin-4-yl)-3-methylpropyn-1-yl)naphthalen-1-yl]-urea;
1-[5-tert-Butyl-2-p-tolyl-2H-pyrazol-3-yl]-3-[4-(3-(morpholin-4-yl)-3,3-dimethylpropyn-1-yl)naphthalen-1-yl]-urea;
1-[5-tert-Butyl-2-p-tolyl-2H-pyrazol-3-yl]-3-[4-(3-(tetrahydropyran-2-yl-oxy)butyn-1-yl)naphthalen-1-yl]-urea;
1-[5-tert-Butyl-2-p-tolyl-2H-pyrazol-3-yl]-3-[4-(3-(furan-2-ylcarbonyloxy)propyn-1-yl)naphthalen-1-yl]-urea;
1-[5-tert-Butyl-2-p-tolyl-2H-pyrazol-3-yl]-3-[4-(3-(piperdin-1-yl)propyn-1-yl)naphthalen-1-yl]-urea;
1-[5-tert-Butyl-2-p-tolyl-2H-pyrazol-3-yl]-3-[4-(3-(2-methoxymethylmorpholin-4-yl)propyn-1-yl)naphthalen-1-yl]-urea;
1-[5-tert-Butyl-2-p-tolyl-2H-pyrazol-3-yl]-3-[4-(pyridin-4-yl-methoxy)naphthalen-yl]-urea;
1-[5-tert-Butyl-2-p-tolyl-2H-pyrazol-3-yl]-3-[4-(2-pyridin-4-yl-ethoxy)naphthalen-1-yl]-urea;
1-[5-tert-Butyl-2-p-tolyl-2H-pyrazol-3-yl]-3-[4-(3-pyridin-4-yl-propoxy)naphthalen-1-yl]-urea;

1-[5-tert-Butyl-2-p-tolyl-2H-pyrazol-3-yl]-3-[4-(2-imidazol-1-yl-ethoxy)naphthalen-1-yl]-urea;
1-[5-tert-Butyl-2-p-tolyl-2H-pyrazol-3-yl]-3-[4-(2-benzimidazol-1-yl-ethoxy)naphthalen-1-yl]-urea;
1-[5-tert-Butyl-2-p-tolyl-2H-pyrazol-3-yl]-3-[4-(2-(3,4-dimethoxyphenyl)-ethoxy)naphthalen-1-yl]-urea;
1-[5-tert-Butyl-2-p-tolyl-2H-pyrazol-3-yl]-3-[4-(pyridin-4-yl-methylamino)naphthalen-1-yl]-urea;
1-[5-tert-Butyl-2-p-tolyl-2H-pyrazol-3-yl]-3-[4-(pyridin-4-yl-carbonylamino)naphthalen-1-yl]-urea;
1-[5-tert-Butyl-2-p-tolyl-2H-pyrazol-3-yl]-3-[4-(morpholin-4-yl-acetamido)naphthalen-1-yl]-urea;
1-[5-tert-Butyl-2-p-tolyl-2H-pyrazol-3-yl]-3-[4-(pyridin-3-yl-methylamino)naphthalen-1-yl]-urea;
1-[5-tert-Butyl-2-p-tolyl-2H-pyrazol-3-yl]-3-[4-(pyridin-3-yl-carbonylamino)naphthalen-1-yl]-urea;
1-[5-iso-Propyl-2-phenyl-2H-pyrazol-3-yl]-3-[4-(2-morpholin-4-yl-ethoxy)naphthalen-1-yl]-urea;
1-[5-(Tetrahydropyran-3-yl)-2-phenyl-2H-pyrazol-3-yl]-3-[4-(2-morpholin-4-ethoxy)naphthalen-1-yl]-urea;
1-[5-cyclohexyl-2-phenyl-2H-pyrazol-3-yl]-3-[4-(2-morpholin-4-yl-ethoxy)naphthalen-1-yl]-urea;
1-[5-(2,2,2-trifluoroethyl)-2-phenyl-2H-pyrazol-3-yl]-3-[4-(2-morpholin-4-yl-ethoxy)naphthalen-1-yl]-urea;
1-[5-(1-methylcycloprop-1-yl)-2-phenyl-2H-pyrazol-3-yl]-3-[4-(2-morpholin-4-yl-ethoxy)naphthalen-1-yl]-urea;
1-[5-ethoxycarbonyl-2-phenyl-2H-pyrazol-3-yl]-3-[4-(2-morpholin-4-yl-ethoxy)naphthalen-1-yl]-urea;
1-[5-(1-methylcyclohex-1-yl)-2-phenyl-2H-pyrazol-3-yl]-3-[4-(2-morpholin-4-yl-ethoxy)naphthalen-1-yl]-urea;
1-[5-tert-butyl-2-methyl-2H-pyrazol-3-yl]-3-[4-(2-morpholin-4-yl-ethoxy)naphthalen-1-yl]-urea;
1-[5-tert-butyl-2-benzyl-2H-pyrazol-3-yl]-3-[4-(2-morpholin-4-yl-ethoxy)naphthalen-1-yl]-urea;
1-[5-tert-butyl-2-(4-chlorophenyl)-2H-pyrazol-3-yl]-3-[4-(2-morpholin-4-yl-ethoxy)naphthalen-1-yl]-urea;
1-[5-tert-butyl-2-butyl-2H-pyrazol-3-yl]-3-[4-(2-morpholin-4-yl-ethoxy)naphthalen-1-yl]-urea;
1-[5-tert-butyl-2-(ethoxycarbonylmethyl)-2H-pyrazol-3-yl]-3-[4-(2-morpholin-4-yl-ethoxy)naphthalen-1-yl]-urea;
1-[5-tert-butyl-2-(4-methyl-3-carbamylphenyl)-2H-pyrazol-3-yl]-3-[4-(2-morpholin-4-yl-ethoxy)naphthalen-1-yl]-urea;
1-[5-tert-butyl-2-(4-methyl-3-(2-ethoxycarbonylvinyl)phenyl)-2H-pyrazol-3-yl]-3-[4-(2-morpholin-4-yl-ethoxy)naphthalen-1-yl]-urea;
1-[5-tert-butyl-2-(4-methyl-3-(morpholin-4-yl)methylphenyl)-2H-pyrazol-3-yl]-3-[4-(2-morpholin-4-yl-ethoxy)naphthalen-1-yl]-urea;
1-[5-tert-butyl-2-(4-methyl-3-dimethylaminomethylphenyl)-2H-pyrazol-3-yl]-3-[4-(2-morpholin-4-yl-ethoxy)naphthalen-1-yl]-urea;
1-[5-tert-butyl-2-(3-(2-morpholin-4-yl-ethyl)phenyl)-2H-pyrazol-3-yl]-3-[4-(2-morpholin-4-yl-ethoxy)naphthalen-1-yl]-urea;
1-[5-tert-butyl-2-(3-(tetrahydropyran-4-ylamino)phenyl)-2H-pyrazol-3-yl]-3-[4-(2-morpholin-4-yl-ethoxy)naphthalen-1-yl]-urea;
1-[5-tert-butyl-2-(3-dimethylaminomethylphenyl)-2H-pyrazol-3-yl]-3-[4-(2-morpholin-4-yl-ethoxy)naphthalen-1-yl]-urea;
1-[5-tert-butyl-2-(4-(tetrahydropyran-4-ylamino)phenyl)-2H-pyrazol-3-yl]-3-[4-(2-morpholin-4-yl-ethoxy)naphthalen-1-yl]-urea;
1-[5-tert-butyl-2-(4-(3-benzylureido)phenyl)-2H-pyrazol-3-yl]-3-[4-(2-morpholin-4-yl-ethoxy)naphthalen-1-yl]-urea;
1-[5-tert-butyl-2-(2-chloropyridin-5-yl)-2H-pyrazol-3-yl]-3-[4-(2-morpholin-4-ethoxy)naphthalen-1-yl]-urea;
1-[5-tert-butyl-2-(2-methylpyridin-5-yl)-2H-pyrazol-3-yl]-3-[4-(2-morpholin-4-yl-ethoxy)naphthalen-1-yl]-urea;
1-[5-tert-butyl-2-(2-methoxypyridin-5-yl)-2H-pyrazol-3-yl]-3-[4-(2-morpholin-4-yl-ethoxy)naphthalen-1-yl]-urea;
1-[5-tert-butyl-2-(pyridin-3-yl)-2H-pyrazol-3-yl]-3-[4-(2-morpholin-4-yl-ethoxy)naphthalen-1-yl]-urea;
1-[5-tert-butyl-2-(2-methylpyridin-5-yl)-2H-pyrazol-3-yl]-3-[4-(2-pyridin-4-yl-ethoxy)naphthalen-1-yl]-urea;
1-[5-tert-butyl-2-(2-methylpyridin-5-yl)-2H-pyrazol-3-yl]-3-[4-(2-(trans-2,6-dimethylmorpholin-4-yl)ethoxy)naphthalen-1-yl]-urea;
1-[5-tert-butyl-2-(2-methylpyridin-5-yl)-2H-pyrazol-3-yl]-3-[4-(3-morpholin-4-yl-propyn-1-yl)naphthalen-1-yl]-urea;
1-[5-tert-Butyl-2-p-tolyl-2H-pyrazol-3-yl]-3-[4-(2-(2-dimethylaminomethylmorpholin-4-yl)ethoxy)naphthalen-1-yl]-urea;
1-[5-tert-butyl-2-iso-propyl-2H-pyrazol-3-yl]-3-[4-(2-morpholin-4-yl-ethoxy)naphthalen-1-yl]-urea;
1-[5-tert-butyl-2-cyclopropyl-2H-pyrazol-3-yl]-3-[4-(2-morpholin-4-yl-ethoxy)naphthalen-1-yl]-urea;
1-[5-tert-butyl-2-(thiophen-3-yl)-2H-pyrazol-3-yl]-3-[4-(2-morpholin-4-yl-ethoxy)naphthalen-1-yl]-urea;
1-[5-tert-butyl-2-cyclopentyl-2H-pyrazol-3-yl]-3-[4-(2-morpholin-4-yl-ethoxy)naphthalen-1-yl]-urea;
1-[5-tert-butyl-2-iso-propyl-2H-pyrazol-3-yl]-3-[4-(tetrahydropyran-4-yl-ethoxy)naphthalen-1-yl]-urea;
1-[5-tert-butyl-2-cyclopropyl-2H-pyrazol-3-yl]-3-[4-(1-oxo-tetrahydrothiophen-3-yl-ethoxy)naphthalen-1-yl]-urea;
1-[5-tert-butyl-2-(thiophen-3-yl)-2H-pyrazol-3-yl]-3-[4-(2-pyridinyl-4-yl-ethoxy)naphthalen-1-yl]-urea;
1-[5-tert-butyl-2-cyclopentyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(3-(pyridin-4-yl)propyn-1-yl)naphthalen-1-yl]-urea;
1-[5-tert-Butyl-2-p-tolyl-2H-pyrazol-3-yl]-3-[4-(3-(2-methylaminopyridin-4-yl)propyn-1-yl)naphthalen-1-yl]-urea;
1-[5-tert-Butyl-2-p-tolyl-2H-pyrazol-3-yl]-3-[4-(3-(1-oxo-tetrahydothiophen-3-yl)propyn-1-yl)naphthalen-1-yl]-urea;
1-[5-tert-Butyl-2-p-tolyl-2H-pyrazol-3-yl]-3-[4-(3-(thiazolidin-3-yl)propyn-1-yl)naphthalen-1-yl]-urea;
1-[5-tert-Butyl-2-p-tolyl-2H-pyrazol-3-yl]-3-[4-(3-(tetrahydropyran-4-yl)propyn-1-yl)naphthalen-1-yl]-urea;
1-[5-tert-Butyl-2-p-tolyl-2H-pyrazol-3-yl]-3-[4-(2-methylaminopyrimidin-4-yl-methoxy)naphthalen-1-yl]-urea;
1-[5-tert-Butyl-2-p-tolyl-2H-pyrazol-3-yl]-3-[4-(2-(2-methylaminopyrimidin-4-yl)ethoxy)naphthalen-1-yl]-urea;
1-[5-tert-Butyl-2-p-tolyl-2H-pyrazol-3-yl]-3-[4-(2-(4-methoxybenzimidazol-1-yl)ethoxy)naphthalen-1-yl]-urea;
1-[5-tert-Butyl-2-p-tolyl-2H-pyrazol-3-yl]-3-[4-(2-(4-methylaminobenzimidazol-1-yl)ethoxy)naphthalen-1-yl]-urea;
1-[5-tert-Butyl-2-p-tolyl-2H-pyrazol-3-yl]-3-[4-(2-(2-imidazo[4,5-b]pyridin-1-yl)ethoxy)naphthalen-1-yl]-urea;
1-[5-tert-Butyl-2-p-tolyl-2H-pyrazol-3-yl]-3-[4-(2-[1,8]naphthyridin-4-yl)ethoxy)naphthalen-1-yl]-urea;

1-[5-tert-Butyl-2-p-tolyl-2H-pyrazol-3-yl]-3-[4-(2-(3,4-dihydro-2H-pyrano[2,3-b]pyridin-5-yl)ethoxy)naphthalen-1-yl]-urea;
1-[5-tert-Butyl-2-pyridin-3-yl-2H-pyrazol-3-yl]-3-[4-(2-methylaminopyrimidin-4-methoxy)naphthalen-1-yl]-urea;
1-[5-tert-Butyl-2-(2-methylpyridin-5-yl)-2H-pyrazol-3-yl]-3-[4-(2-(2-methylaminopyrimidin-4-yl)ethoxy)naphthalen-1-yl]-urea;
1-[5-tert-Butyl-2-(2-methylpyridin-5-yl)-2H-pyrazol-3-yl]-3-[4-(2-(4-methoxybenzimidazol-1-yl)ethoxy)naphthalen-1-yl]-urea;
1-[5-tert-Butyl-2-(2-methylpyridin-5-yl)-2H-pyrazol-3-yl]-3-[4-(2-(4-methylaminobenzimidazol-1-yl)ethoxy)naphthalen-1-yl]-urea;
1-[5-tert-Butyl-2-(2-methylpyridin-5-yl)-2H-pyrazol-3-yl]-3-[4-(2-(2-imidazo[4,5-b]pyridin-1-yl)ethoxy)naphthalen-1-yl]-urea;
1-[5-tert-Butyl-2-(2-methylpyridin-5-yl)-2H-pyrazol-3-yl]-3-[4-(2-[1,8]naphthyridin-4-yl)ethoxy)naphthalen-1-yl]-urea;
1-[5-tert-Butyl-2-(2-methylpyridin-5-yl)-2H-pyrazol-3-yl]-3-[4-(2-(3,4-dihydro-2H-pyrano[2,3-b]pyridin-5-yl)ethoxy)naphthalen-1-yl]-urea;
1-[5-tert-Butyl-2-cyclopropyl-2H-pyrazol-3-yl]-3-[4-(2-methylaminopyrimidin-4-yl-methoxy)naphthalen-1-yl]-urea;
1-[5-tert-Butyl-2-cyclopropyl-2H-pyrazol-3-yl]-3-[4-(2-(2-methylaminopyrimidin-4-yl)ethoxy)naphthalen-1-yl]-urea;
1-[5-tert-Butyl-2-cyclopropyl-2H-pyrazol-3-yl]-3-[4-(2-(4-methoxybenzimidazol-1-yl)ethoxy)naphthalen-1-yl]-urea;
1-[5-tert-Butyl-2-cyclopropyl-2H-pyrazol-3-yl]-3-[4-(2-(4-methylaminobenzimidazol-1-yl)ethoxy)naphthalen-1-yl]-urea;
1-[5-tert-Butyl-2-methyl-2H-pyrazol-3-yl]-3-[4-(2-(2-imidazo[4,5-b]pyridin-1-yl)ethoxy)naphthalen-1-yl]-urea;
1-[5-tert-Butyl-2-methyl-2H-pyrazol-3-yl]-3-[4-(2-[1,8]naphthyridin-4-yl)ethoxy)naphthalen-1-yl]-urea;
1-[5-tert-Butyl-2-methyl-2H-pyrazol-3-yl]-3-[4-(2-(3,4-dihydro-2H-pyrano[2,3-b]pyridin-5-yl)ethoxy)naphthalen-1-yl]-urea and their physiologically acceptable acids or salts thereof.
Preferred compounds of the formula(I) are:

1-[5-tert-Butyl-2-p-tolyl-2H-pyrazol-3-yl]-3-[4-(2-morpholin-4-yl-ethoxy)naphthalen-1-yl]-urea;
1-[5-tert-Butyl-2-p-tolyl-2H-pyrazol-3-yl]-3-[4-(2-(cis-2,6-dimethylmorpholin-4-yl)ethoxy)naphthalen-1-yl]-urea;
1-[5-tert-Butyl-2-p-tolyl-2H-pyrazol-3-yl]-3-[4-(2-(trans-2,6-dimethylmorpholin-4-yl)ethoxy)naphthalen-1-yl]-urea;
1-[5-tert-Butyl-2-p-tolyl-2H-pyrazol-3-yl]-3-[4-(2-(2-(methoxymethyl)morpholin-4-yl)ethoxy)naphthalen-1-yl]-urea;
1-[5-tert-Butyl-2-p-tolyl-2H-pyrazol-3-yl]-3-[4-(2-(morpholin-4-yl)-2-oxoethoxy)naphthalen-1-yl]-urea;
1-[5-tert-Butyl-2-p-tolyl-2H-pyrazol-3-yl]-3-[4-(2-(morpholin-4-yl)-2-methylethoxy)naphthalen-1-yl]-urea;
1-[5-tert-Butyl-2-p-tolyl-2H-pyrazol-3-yl]-3-[4-(2-(morpholin-4-yl)-1-methylethoxy)naphthalen-1-yl]-urea;
1-[5-tert-Butyl-2-p-tolyl-2H-pyrazol-3-yl]-3-[4-(2-thiomorpholin-4-yl-ethoxy)naphthalen-1-yl]-urea;
1-[5-tert-Butyl-2-p-tolyl-2H-pyrazol-3-yl]-3-[4-(2-(1-oxothiomorpholin-4-yl)ethoxy)naphthalen-1-yl]-urea;
1-[5-tert-Butyl-2-p-tolyl-2H-pyrazol-3-yl]-3-[4-(2-morpholin-4-yl-ethoxy)-3-methylnaphthalen-1-yl]-urea;
1-[5-tert-Butyl-2-p-tolyl-2H-pyrazol-3-yl]-3-[4-(2-(morpholin-4-yl-carbonyloxo)ethoxy)naphthalen-1-yl]-urea;
1-[5-tert-Butyl-2-p-tolyl-2H-pyrazol-3-yl]-3-[4-(2-(tetrahydropyran-4-yl)ethoxy)naphthalen-1-yl]-urea;
1-[5-tert-Butyl-2-p-tolyl-2H-pyrazol-3-yl]-3-[4-(2-(1-oxo-tetrahydrothiophen-3-yl)ethoxy)naphthalen-1-yl]-urea;
1-[5-tert-Butyl-2-p-tolyl-2H-pyrazol-3-yl]-3-[4-(3-morpholin-4-yl-propyl)naphthalen-1-yl]-urea;
1-[5-tert-Butyl-2-p-tolyl-2H-pyrazol-3-yl]-3-[4-(morpholin-4-yl-methyl)naphthalen-1-yl]-urea;
1-[5-tert-Butyl-2-p-tolyl-2H-pyrazol-3-yl]-3-[4-(2-pyridin-4-yl-ethyl)naphthal-1-yl]-urea;
1-[5-tert-Butyl-2-p-tolyl-2H-pyrazol-3-yl]-3-[4-(3-(morpholin-4-yl)propyn-1-yl)naphthalen-1-yl]-urea;
1-[5-tert-Butyl-2-p-tolyl-2H-pyrazol-3-yl]-3-[4-(3-(tetrahydropyran-2-yl-oxy)propyn-1-yl)naphthalen-1-yl]-urea;
1-[5-tert-Butyl-2-p-tolyl-2H-pyrazol-3-yl]-3-[4-(3-(tetrahydropyran-2-yl-oxy)butyn-1-yl)naphthalen-1-yl]-urea;
1-[5-tert-Butyl-2-p-tolyl-2H-pyrazol-3-yl]-3-[4-(3-(piperdin-1-yl)propyn-1-yl)naphthalen-1-yl]-urea;
1-[5-tert-Butyl-2-p-tolyl-2H-pyrazol-3-yl]-3-[4-(3-(2-methoxymethylmorpholin-4-yl)propyn-1-yl)naphthalen-1-yl]-urea;
1-[5-tert-Butyl-2-p-tolyl-2H-pyrazol-3-yl]-3-[4-(pyridin-4-yl-methoxy)naphthalen-1-yl]-urea;
1-[5-tert-Butyl-2-p-tolyl-2H-pyrazol-3-yl]-3-[4-(2-pyridin-4-yl-ethoxy)naphthalen-1-yl]-urea;
1-[5-tert-Butyl-2-p-tolyl-2H-pyrazol-3-yl]-3-[4-(3-pyridin-4-yl-propoxy)naphthalen-1-yl]-urea;
1-[5-tert-Butyl-2-p-tolyl-2H-pyrazol-3-yl]-3-[4-(2-imidazol-1-yl-ethoxy)naphthalen-1-yl]-urea;
1-[5-tert-Butyl-2-p-tolyl-2H-pyrazol-3-yl]-3-[4-(2-(3,4-dimethoxyphenyl)-ethoxy)naphthalen-1-yl]-urea;
1-[5-tert-Butyl-2-p-tolyl-2H-pyrazol-3-yl]-3-[4-(pyridin-4-yl-methylamino)naphthalen-1-yl]-urea;
1-[5-iso-Propyl-2-phenyl-2H-pyrazol-3-yl]-3-[4-(2-morpholin-4-yl-ethoxy)naphthalen-1-yl]-urea;
1-[5-cyclohexyl-2-phenyl-2H-pyrazol-3-yl]-3-[4-(2-morpholin-4-yl-ethoxy)naphthalen-1-yl]-urea;
1-[5-(2,2,2-trifluoroethyl)-2-phenyl-2H-pyrazol-3-yl]-3-[4-(2-morpholin-4-yl-ethoxy)naphthalen-1-yl]-urea;
1-[5-(1-methylcycloprop-1-yl)-2-phenyl-2H-pyrazol-3-yl]-3-[4-(2-morpholin-4-yl-ethoxy)naphthalen-1-yl]-urea;
1-[5-(1-methylcyclohex-1-yl)-2-phenyl-2H-pyrazol-3-yl]-3-[4-(2-morpholin-4-yl-ethoxy)naphthalen-1-yl]-urea;
1-[5-tert-butyl-2-methyl-2H-pyrazol-3-yl]-3-[4-(2-morpholin-4-yl-ethoxy)naphthalen-1-yl]-urea;
1-[5-tert-butyl-2-(4-chlorophenyl)-2H-pyrazol-3-yl]-3-[4-(2-morpholin-4-yl-ethoxy)naphthalen-1-yl]-urea;
1-[5-tert-butyl-2-butyl-2H-pyrazol-3-yl]-3-[4-(2-morpholin-4-yl-ethoxy)naphthalen-1-yl]-urea;
1-[5-tert-butyl-2-(4-methyl-3-carbamylphenyl)-2H-pyrazol-3-yl]-3-[4-(2-morpholin-4-yl-ethoxy)naphthalen-1-yl]-urea;
1-[5-tert-butyl-2-(4-methyl-3-(morpholin-4-yl)methylphenyl)-2H-pyrazol-3-yl]-3-[4-(2-morpholin-4-yl-ethoxy)naphthalen-1-yl]-urea;
1-[5-tert-butyl-2-(4-methyl-3-dimethylaminomethylphenyl)-2H-pyrazol-3-yl]-3-[4-(2-morpholin-4-yl-ethoxy)naphthalen-1-yl]-urea;
1-[5-tert-butyl-2-(3-dimethylaminomethylphenyl)-2H-pyrazol-3-yl]-3-[4-(2-morpholin-4-yl-ethoxy)naphthalen-1-yl]-urea;
1-[5-tert-butyl-2-(2-chloropyridin-5-yl)-2H-pyrazol-3-yl]-3-[4-(2-morpholin-4-yl-ethoxy)naphthalen-1-yl]-urea;
1-[5-tert-butyl-2-(2-methylpyridin-5-yl)-2H-pyrazol-3-yl]-3-[4-(2-morpholin-4-yl-ethoxy)naphthalen-1-yl]-urea;
1-[5-tert-butyl-2-(2-methoxypyridin-5-yl)-2H-pyrazol-3-yl]-3-[4-(2-morpholin-4-yl-ethoxy)naphthalen-1-yl]-urea;
1-[5-tert-butyl-2-(pyridin-3-yl)-2H-pyrazol-3-yl]-3-[4-(2-morpholin-4-yl-ethoxy)naphthalen-1-yl]-urea;
1-[5-tert-butyl-2-(2-methylpyridin-5-yl)-2H-pyrazol-3-yl]-3-[4-(2-pyridin-4-yl-ethoxy)naphthalen-1-yl]-urea;

1-[5-tert-butyl-2-(2-methylpyridin-5-yl)-2H-pyrazol-3-yl]-3-[4-(2-(trans-2,6-dimethylmorpholin-4-yl)ethoxy)naphthalen-1-yl]-urea;

1-[5-tert-butyl-2-(2-methylpyridin-5-yl)-2H-pyrazol-3-yl]-3-[4-(3-morpholin-4-yl-propyn-1-yl)naphthalen-1-yl]-urea.

Particularly preferred compounds of the formula(I) are:

1-[5-tert-Butyl-2-p-tolyl-2H-pyrazol-3-yl]-3-[4-(2-morpholin-4-yl-ethoxy)naphthalen-1-yl]-urea;

1-[5-tert-Butyl-2-p-tolyl-2H-pyrazol-3-yl]-3-[4-(2-(1-oxothiomorpholin-4-yl)ethoxy)naphthalen-1-yl]-urea;

1-[5-tert-butyl-2-(2-methylpyridin-5-yl)-2H-pyrazol-3-yl]-3-[4-(2-pyridin-4-ethoxy)naphthalen-1-yl]-urea;

1-[5-tert-butyl-2-(2-methoxypyridin-5-yl)-2H-pyrazol-3-yl]-3-[4-(2-morpholin-4-yl-ethoxy)naphthalen-1-yl]-urea or 1-[5-tert-butyl-2-methyl-2H-pyrazol-3-yl]-3-[4-(2-morpholin-4-yl-ethoxy)naphthalen-1-yl]-urea.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes all such tautomers.

The term "aroyl" as used in the present specification shall be understood to mean "benzoyl" or "naphthoyl".

The invention includes pharmaceutically acceptable derivatives of compounds of formula (I). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof.

The term "metabolite" shall be understood to mean any of the compounds of the formula (I) which are capable of being hydroxylated or oxidized, enzymatically or chemically, as will be appreciated by those skilled in the art. Nonlimiting examples of metabolites of the formula (I) are shown in the table below:

| Structure | Name |
|---|---|
| 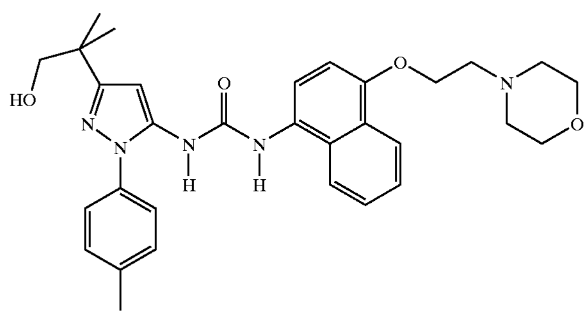 | 1-[5-(2-hydroxy-1,1-dimethyl-ethyl)-2-p-tolyl-2H-pyrazol-3-yl]-3-[4-(2-morpholin-4-yl-ethoxy)-naphthalen-]-yl]-urea |
| 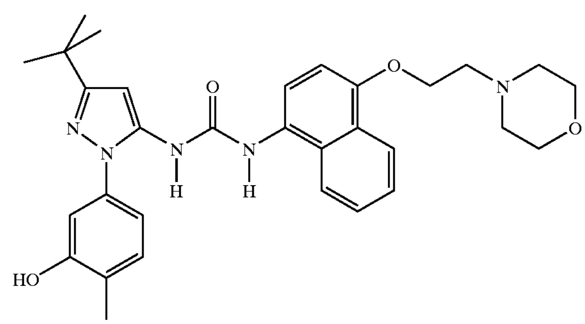 | 1-[5-tert-butyl-2-(3-hydroxy-4-methyl-phenyl)-2H-pyrazol-3-yl]-3-[4-(2-morpholin-4-yl-ethoxy)-naphthalen-1-yl]-urea |
| 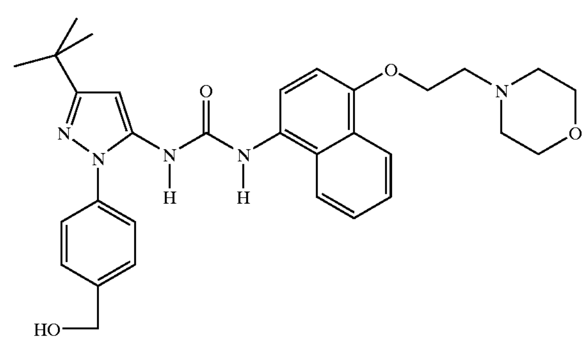 | 1-[5-tert-butyl-2-(4-hydroxymethyl-phenyl)-2H-pyrazol-3-yl]-3-[4-(2-morpholin-4-yl-ethoxy)-naphthalen-1-y]-urea |

-continued

| Structure | Name |
|---|---|
| 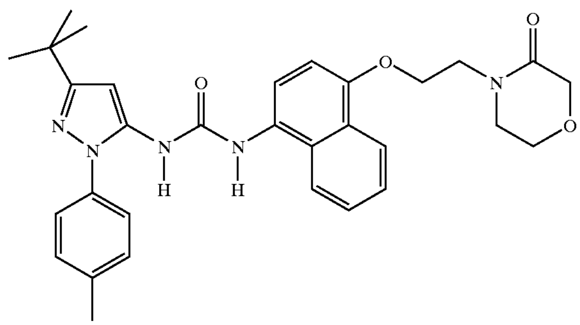 | 1-[5-tert-butyl-2-p-tolyl-2H-pyrazol-3-yl]-3-{4-[2-(3-oxo-morpholin-4-yl)-ethoxy]-naphthalen-1-yl}-urea |
| 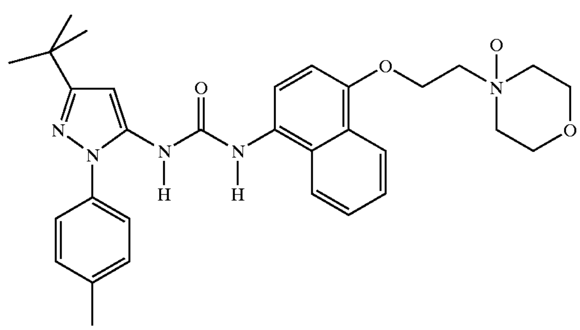 | 1-[5-tert-butyl-2-p-tolyl-2H-pyrazol-3-yl]-3-{4-[2-(4-oxy-morpholin-4-yl)-ethoxy]-naphthalen-1-yl}-urea |
| 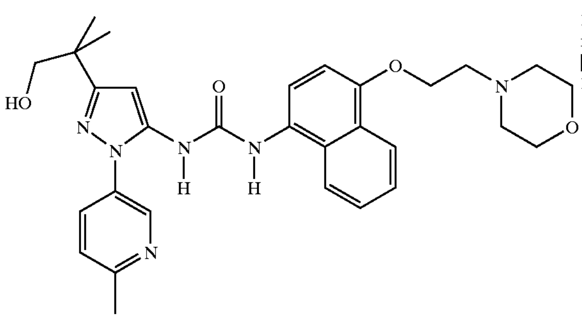 | 1-[5-(2-hydroxy-1,1-dimethyl-ethyl)-2-(6-methyl-pyridin-3-yl)-2H-pyrazol-3-yl]-3-[4-(2-morpholin-4-yl-ethoxy)-naphthalen-1-yl]-urea |
| 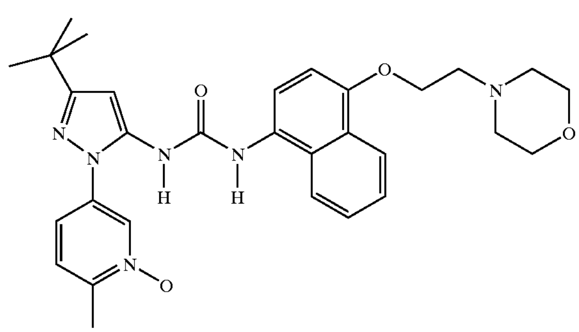 | 1-[5-tert-butyl)-2-(1-oxy-6-methyl-pyridin-3-yl)-2H-pyrazol-3-yl]-3-[4-(2-morpholin-4-yl-ethoxy)-naphthalen-1-yl]-urea |

-continued

| Structure | Name |
|---|---|
| 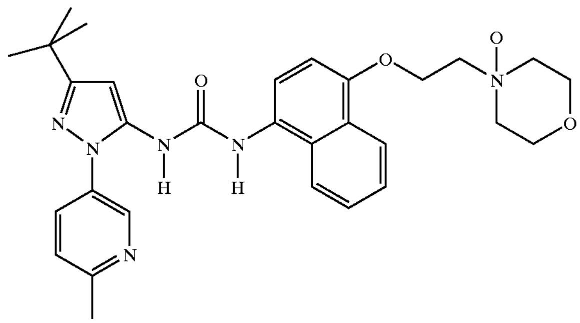 | 1-[5-tert-butyl)-2-(6-methyl-pyridin-3-yl)-2H-pyrazol-3-yl]-3-{4-[2-(4-oxy-morpholin-4-yl)-ethoxy]-naphthalen-1-yl}-urea |
| 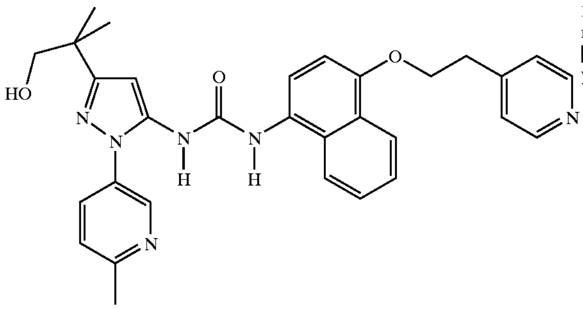 | 1-[5-(2-hydroxy-1,1-dimethyl-ethyl)-2-(6-methyl-pyridin-3-yl)-2H-pyrazol-3-yl]-3-[4-(2-pyridin-4-yl-ethoxy)-naphthalen-1-yl]-urea |
| 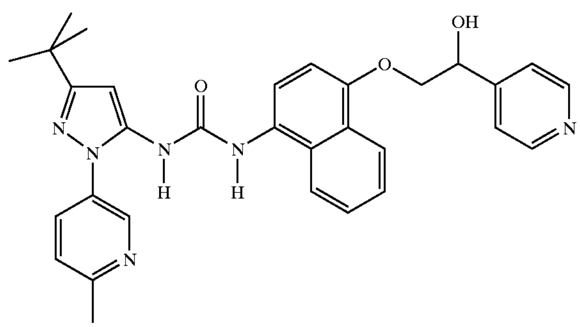 | 1-[5-tert-butyl)-2-(6-methyl-pyridin-3-yl)-2H-pyrazol-3-yl]-3-[4-(2-hydroxy-2-pyridin-4-yl-ethoxy)-naphthalen-1-yl]-urea |
| 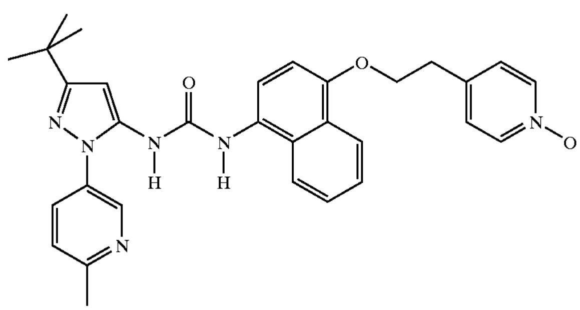 | 1-[5-tert-butyl)-2-(6-methyl-pyridin-3-yl)-2H-pyrazol-3-yl]-3-{4-[2-(1-oxy-pyridin-4-yl)-ethoxy]-naphthalen-1-yl}-urea |
| 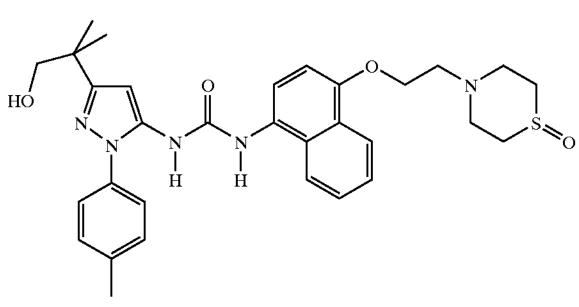 | 1-[5-(2-hydroxy-1,1-dimethyl-ethyl)-2-p-tolyl-2H-pyrazol-3-yl]-3-{4-[2-(1-oxo-thiomorpholin-4-yl)-ethoxy]-naphthalen-1-yl}-urea |

| Structure | Name |
|---|---|
| 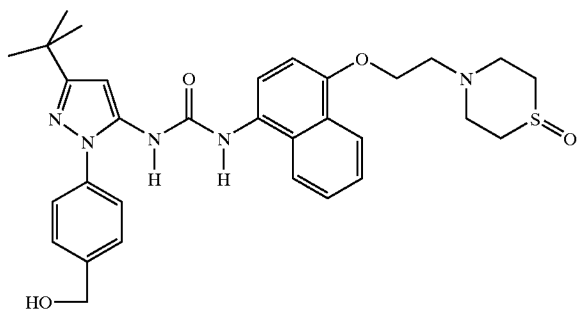 | 1-[5-tert-butyl-2-(4-hydroxymethyl-phenyl)-2H-pyrazol-3-yl]-3-{4-[2-(1-oxo-thiomorpholin-4-yl)-ethoxy]-naphthalen-1-yl}-urea |
| 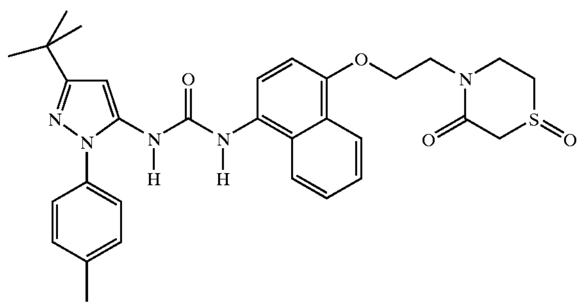 | 1-[5-tert-butyl-2-p-tolyl-2H-pyrazol-3-yl]-3-{4-[2-(1,3 dioxo-thiomorpholin-4-yl)-ethoxy]-naphthalen-1-yl]-urea |
| 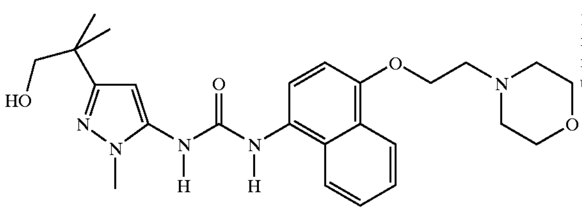 | 1-[5-(2-hydroxy-1,1-dimethyl-ethyl)-2-methyl-2H-pyrazol-3-yl]-3-[4-(2-morpholin-4-yl-ethoxy)-naphthalen-1-yl]-urea |
| 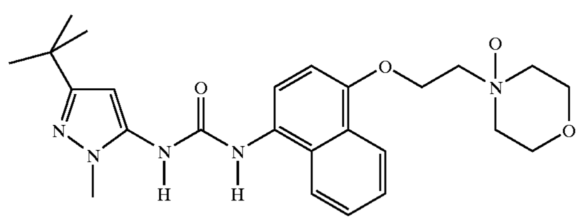 | 1-[5-tert-butyl-2-methyl-2H-pyrazol-3-yl]-3-{4-[2-(4-oxy-morpholin-4-yl)-ethoxy]-naphthalen-1-yl}-urea |
| 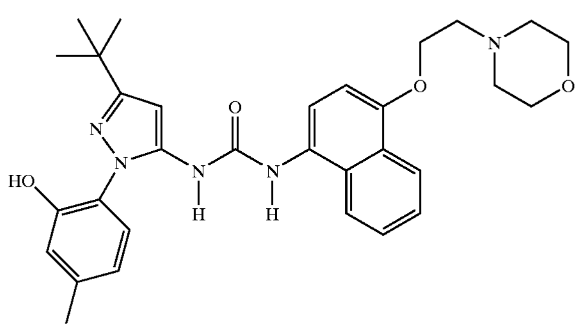 | 1-[5-tert-Butyl-2-(2-hydroxy-4-methyl-phenyl)-2H-pyrazol-3-yl]-3-[4-(2-morpholin-4-yl-ethoxy)-naphthalen-1-yl]-urea |

| Structure | Name |
|---|---|
| 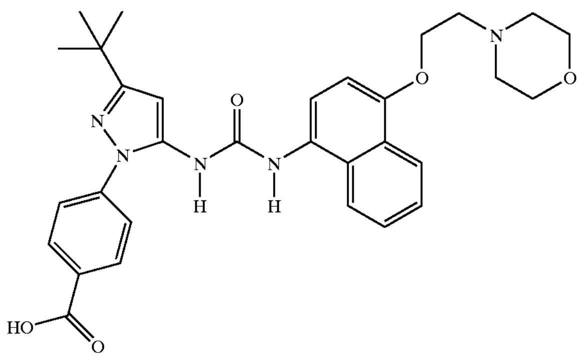 | 4-(3-tert-Butyl-5-{3-[4-(2-morpholin-4-yl-ethoxy)-naphthalen-1-yl]-ureido}-pyrazol-1-yl)-benzoic acid |
| 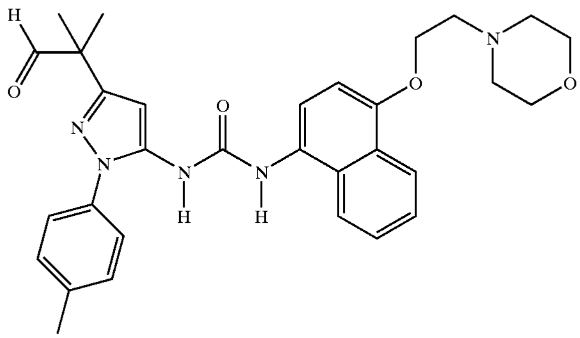 | 1-[5-(1,1-Dimethyl-2-oxo-ethyl)-2-p-tolyl-2H-pyrazol-3-yl]-3-[4-(2-morpholin-4-yl-ethoxy)-naphthalen-1-yl]-urea |
| 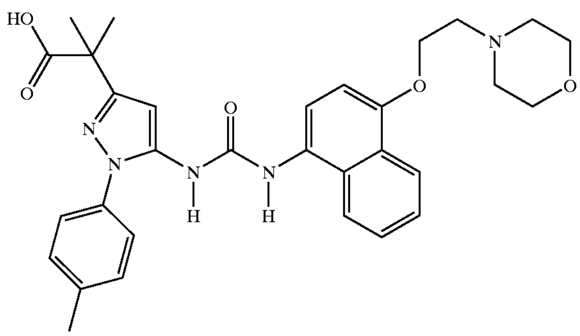 | 2-Methyl-2-(5-{3-[4-(2-morpholin-4-yl-ethoxy)-naphthalen-1-yl]-ureido}-1-p-tolyl-1H-pyrazol-3-yl)-propionic acid |
| 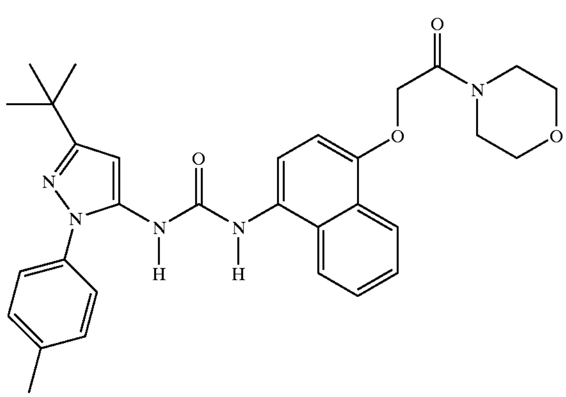 | 1-(5-tert-Butyl-2-p-tolyl-2H-pyrazol-3-yl)-3-[4-(2-morpholin-4-yl-2-oxo-ethoxy)-naphthalen-1-yl]-urea |

| Structure | Name |
|---|---|
| (structure shown) | 1-(5-tert-Butyl-2-p-tolyl-2H-pyrazol-3-yl)-3-{4-[2-(1-oxo-1$\lambda^4$-thiomorpholin-4-yl)-ethoxy]-naphthalen-1-yl}-urea |

These metabolite compounds were evaluated and all had $IC_{50} < 10$ uM in the THP cell assay described below. The compounds are therefore useful for treating cytokine mediated diseases or conditions.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and $N-(C_1-C_4 \text{ alkyl})_4^+$ salts.

In addition, the compounds of this invention include prodrugs of compounds of the formula (I). Prodrugs include those compounds that, upon simple chemical transformation, are modified to produce a compound of formula (I). Simple chemical transformations include hydrolysis, oxidation and reduction. Specifically, when a prodrug of this invention is administered to a patient, the prodrug may be transformed into a compound of formula (I), thereby imparting the desired pharmacological effect.

GENERAL SYNTHETIC METHODS

The invention additionally provides for methods of making the compounds of the formula (I) and its metabolites. The compounds of the invention may be prepared by the general methods and examples presented below, and methods known to those of ordinary skill in the art. Further reference in this regard may be made to U.S. Pat. No. 6,297,381, U.S. application Ser. No. 09/505,582, U.S. Pat. No. 6,358,945, Ser. No. 09/484,638, U.S. Pat. No. 6,319,921, Ser. Nos. 09/735,160, 09/902,085, 09/698,442, U.S. Pat. No. 6,407,238, Ser. Nos. 09/834,797, 09/611,109, U.S. provisional application Nos. 60/206,327, 60/216,283, 60/295,909, 60/293,600, 60/291,425, 60/283,642 and 60/268,841. Each of the aforementioned are incorporated herein by reference in their entirety.

The compounds of the invention may be prepared by Method A, B, or C as illustrated in Scheme I, preferably method C.

Scheme I

Method A

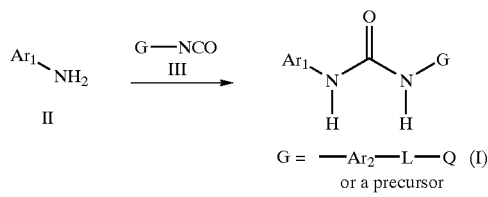

$G = -Ar_2-L-Q$ (I)
or a precursor

Method B

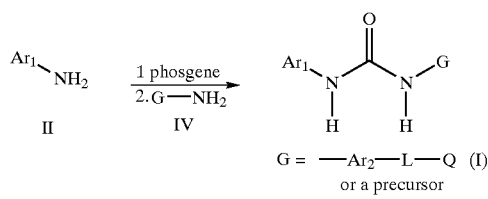

$G = -Ar_2-L-Q$ (I)
or a precursor

Method C

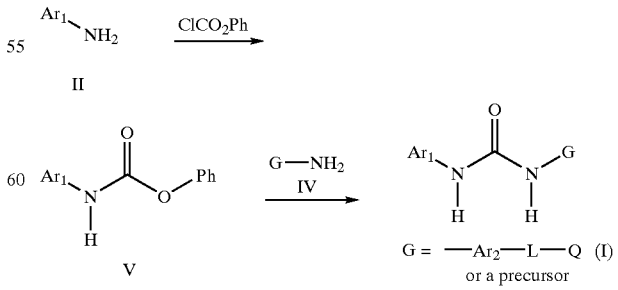

$G = -Ar_2-L-Q$ (I)
or a precursor

In Method A, a mixture of an aminoheterocycle of formula II and an arylisocyanate of formula III is dissolved in a non-protic, anhydrous solvent such as THF, ether, toluene, dioxane or ethyl acetate. The preferred solvent is THF. The mixture is stirred at between 0–45° C., preferably at 25° C., for 2–24 hr, and the volatiles are removed. Purification of the residue by recrystallization from an appropriate solvent such as ethyl acetate/hexanes, ethyl acetate/methanol, THF/petroleum ether, ethanol/water or by silica gel chromatography, using for example, hexanes and ethyl acetate as eluents, provides the product of formula I.

In Method B, an aminoheterocycle of formula II is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5–30 min, with 10 min being preferable. The organic layer is dried, with agents such as $MgSO_4$ or $Na_2SO_4$, and the volatiles removed to provide the corresponding isocyanate of formula II. The isocyanate and arylamine IV are mixed in a non-protic, anhydrous solvent such as THF, ether, toluene, dioxane, methylene chloride or ethyl acetate. The preferred solvent is THF. The mixture is stirred at between 0–45° C., preferably at 25° C., for 2–24 hr, and the volatiles are removed. Purification of the residue by recrystallization or by silica gel chromatography, as above, provides the product of formula I.

In Method C, an aminoheterocycle of formula II is dissolved in a halogenated solvent, such as methylene chloride, chloroform or dichloroethane. The preferred solvent is methylene chloride. A suitable base such as triethylamine may be added, followed by phenyl chloroformate. The mixture is stirred at between 0–85° C., preferably at reflux temperature, for 2–24 hr, and the volatiles are removed providing carbamate V. The carbamate and arylamine IV are mixed in a non-protic, anhydrous solvent such as THF, ether, toluene, dioxane, methylene chloride or ethyl acetate. The preferred solvent is THF. The mixture is stirred at between 0–110C, preferably at reflux temperature, for 2–24 hr, and the volatiles are removed. Purification of the residue as above provides the product of formula I.

The method used to produce an aminoheterocycle of formula II will depend on the nature of the desired heterocycle. In general, intermediates of formula II can be made by methods known to those skilled in the art. Some general methods are illustrated in the schemes below. Compounds G-NCO or $G-NH_2$ in Scheme I may be commercially available, or may be prepared by methods known to those skilled in the art. If G is a precursor of $Ar_2$—L-Q, the desired final product of formula (I) may be constructed by methods known to those skilled in the art. Illustrative examples are contained in the Synthetic Examples section below.

Desired aminopyrazoles of formula XIII can be prepared as described in Scheme II. A hydrazine of formula VIII, bearing substituent $R_3$, may be prepared by Method D or E. In Method D, an aryl bromide of formula VI is dissolved in a non-protic, inert solvent, such as THF, 1,4-dioxane or diethyl ether, and cooled to low temperature under an inert atmosphere. The preferred temperature for the solution is −77° C. A strong base dissolved in a non-protic, inert solvent, such as hexanes, THF or ether, is added dropwise while maintaing a reaction temperature below 0° C. and preferably below −60° C. The preferred bases are alkyl lithium reagents and the most preferred is sec-butyl lithium. After the addition of the base, the reaction mixture is stirred for 10 a period of time between thirty and ninety minutes or until all the starting aryl bromide has been consumed. An excess of dialkyl azodicarboxylate is added while maintaining a reaction temperature below 0° C. and preferrably below −60° C. The preferred dialkyl azodicarboxylate is di-tert-butyl azodicarboxylate. The reaction is stirred at cold temperatures and warmed to room temperature after 0.5 hr to 2 hr. The reaction is quenched with the addition of water and the product extracted into a non-protic solvent, such as ethyl acetate, diethyl ether or chloroform. The organic layers are dried with agents such as $MgSO_4$ or $Na_2SO_4$ and the volatiles removed. The residue is dissolved in protic solvents, such as methanol or iso-propanol, cooled, preferably to 0–5° C. and treated with acid. Preferred acids are hydrochloric, hydrobromic, sulfuric and trifluoroacetic. The most preferred is hydrochloric in gaseous form. After the addition of excess acid the mixture is heated at the reflux temperature of the solvent until all starting material has been consumed. After cooling the product aryl-hydrazine of formula VIII salt is filtered and dried.

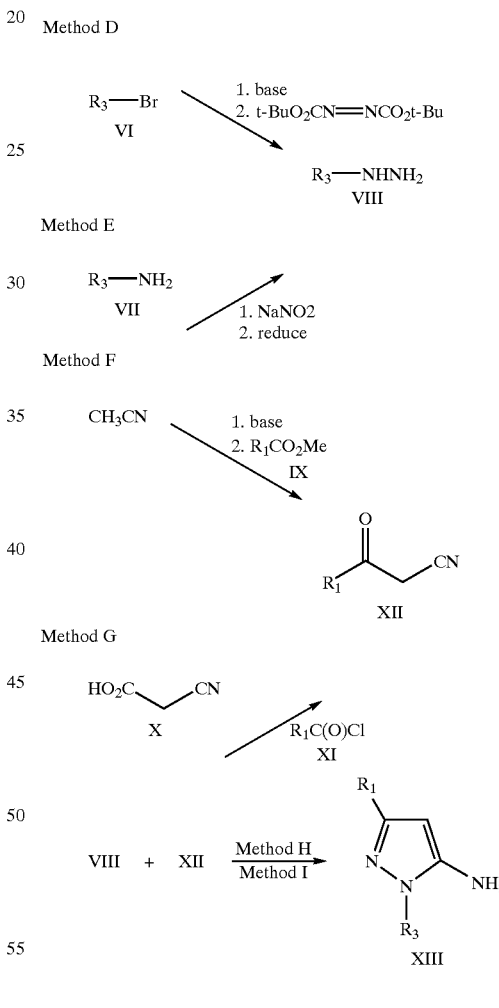

Scheme II

In Method E, an aryl amine bearing $R_3$ of formula VII is dissolved in a concentrated aqueous acid such as hydrochloric, hydrobromic or sulfuric and cooled to ice bath temperatures. The most preferred acid is hydrochloric with concentrations between 3–8 N with the most preferred concentration of 6 N. A nitrosating reagent in water is added dropwise while maintaining a cold temperature. The preferred temperature is 0–5° C. The preferred reagent is sodium nitrite. The reaction is stirred between 10–90 min and a reducing agent is added while maintaining cold temperatures. The 10 preferred temperature is 0–5° C. Reducing agents include zinc, iron, samarium iodide and tin(II) chloride. The most preferred agent is tin(II) chlroride dissolved in aqueous hydrochloride with a concentration of 3–8 N with a most preferred concentration of 6 N. The reaction is stirred between 0.5–3 hr and quenched with alkali to a pH between 12–14. Alkali reagents include sodium hydroxide, potassium hydroxide, lithium hydroxide and calcium hydroxide. The most preferred alkali reagent is potassium hydroxide. The aqueous solution is extracted with a non-protic organic solvent, such as diethyl ether, chloroform, ethyl acetate and methylene chloride. The organic layers are dried with agents such as $MgSO_4$ and $Na_2SO_4$ and the volatiles removed to provide the aryl-hydrazine (VIII) which can be carried forward without further purification.

A β-ketonitrile bearing $R_1$ (XII) may be prepared by Method F or G. In Method F, a metal hydride, such as sodium hydride, potassium hydride or lithium hydride, is suspended in an anhydrous, inert, non-protic solvent, such as diethyl ether, THF and dioxane, at temperatures between 35–85° C. The most preferred metal hydride is sodium hydride and the most preferred solvent is THF at a temperature of 75° C. An alkyl ester, preferably a methyl ester (IX), and acetonitrile is dissolved in an anhydrous, inert, non-protic solvent, such as diethyl ether, THF or dioxane and added dropwise to the metal hydride suspension. The preferred solvent is THF. The mixture is kept at elevated temperatures between 3–24 hours, cooled to room temperature and diluted with a non-protic solvent and aqueous acid. The organic layer is washed with water and brine, dried, with agents such as $MgSO_4$ and $Na_2SO_4$, and the volatiles removed to provide the β-ketonitrile (XII) which could be used without further purification.

Alternatively, following Method G, a solution of a strong base, such as alkyl lithium reagents and metal amide reagents, such as n-butyl lithium, sec-butyl lithium, methyl lithium and lithium diisopropylamide, in an anhydrous, inert, non-protic solvent, such as diethyl ether, THF and dioxane, is cooled below 0° C. The preferred base is n-butyl lithium, the preferred solvent is THF and the preferred temperature is −77° C. A solution of cyanoacetic acid (X) in an anhydrous, inert, non-protic solvent, such as diethyl ether, THF and dioxane, and most preferrably THF, is added dropwise while maintaining a reaction temperature below 0° C. and preferrably at −77° C. The reaction is stirred between 10–45 min while warming to 0° C. The solution of the dianion of cyanoacetic is cooled to temperatures below −25° C. and preferrably at −77° C. An alkyl acid chloride (XI) dissolved in an anhydrous, inert, non-protic solvent, such as diethyl ether, THF and dioxane, and most preferrably THF, is added. The reaction mixture is warmed to 0° C. between 10–30 min. and quenched with aqueous acid. The product is extracted with an organic solvent, such as chloroform, ethyl acetate, ether and methylene chloride. The combined organic extracts are dried, with agents such as $MgSO_4$ and $Na_2SO_4$, and the volatiles removed to provide the β-ketonitrile (XII) which could be used without further purification.

The desired aminopyrazole (XIII) may then be prepared by Method H or I. In Method H, aryl hydrazine VIII and β-ketonitrile XII are mixed in an organic solvent, such as toluene, ethanol, iso-propanol or t-butanol. The preferred solvent is ethanol. An acid, such as hydrochloric acid, p-toluene sulfonic acid or sulfuric acid, is added, The preferred acid is concentrated hydrochloric acid. The mixture is heated to temperatures between 50–100° C., preferrably at 80° C., for 10–24 hr and cooled to room temperature. The mixture is diluted with non-protic organic solvent, such as ethyl acetate, ether, chloroform and methylene chloride, and washed with aqueous alkali, such as sodium bicarbonate and potassium carbonate. The organic layer is dried, with agents such as $MgSO_4$ and $Na_2SO_4$, and the volatiles removed to provide a residue which is purified by recrystallization or silica gel chromatography using hexanes and ethyl acetate as eluents. The product-rich fractions are collected and the volatiles removed to provide the desired amonopyrazole (XIII).

Alternatively, using Method I, aryl hydrazine VIII and β-ketonitrile XII are mixed in an organic solvent, such as toluene, ethanol, iso-propanol or t-butanol. The preferred solvent is toluene. The mixture is heated at reflux temperatures for 3–24 hrs with azeotropic removal of water and worked up as described above providing the aminopyrazole XIII.

A general synthesis for desired aminothiophenes is illustrated in Scheme III, Method J.

Scheme III

Method J

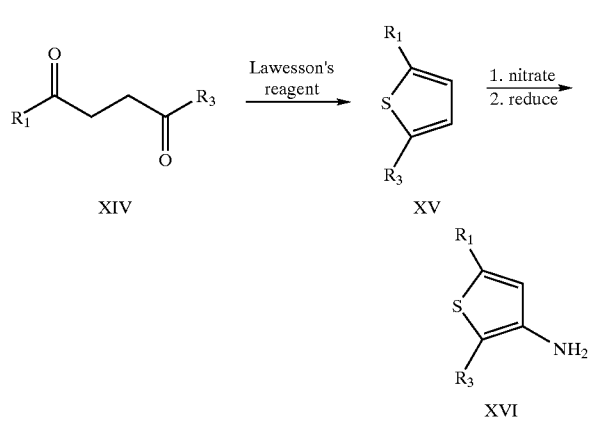

A mixture of 1-aryl-5-alkyl-butane-1,4-dione (XIV) and a sulfating reagent, such as Lawesson's reagent or phosphorous (V) sulfide, and preferrably Lawesson's reagent, is dissolved in a non-protic, anhydrous solvent, such as toluene, THF and dioxane. The preferred solvent is toluene. The mixture is heated at elevated temperatures and preferrably at a solvent-refluxing temperature for 1–10 hr. The volatiles are removed and the residue is purified by silica gel chromatography using hexanes and ethyl acetate as eluent. The product-rich fractions are collected and the volatiles removed to provide the substituted thiophene XV.

A mixture of substituted thiophene XV is dissolved in a solvent such as acetic anhydride or acetic acid. The preferred solvent is acetic anhydride. The mixture is cooled to 0–30° C. and preferrably to −10° C. A solution of concentrated nitric acid in a solvent such as acetic anhydride or acetic acid, with the preferred solvent being acetic anhydride is added while cooling 0–30° C. and preferrably to −10° C. The mixture is stirred between 10 –120 min, poured onto ice and extracted with a non-protic solvent such as diethyl ether, chloroform, ethyl acetate or methylene chloride. The organic extracts are washed with aqueous alkali, dried with agents such as $MgSO_4$ and $Na_2SO_4$ and the volatiles removed. The residue is purified by silica gel chromatography using hexanes and ethyl acetate as eluents. The product-rich fractions are collected and the volatiles removed to provide the 2-aryl-5-alkyl-3-nitrothiophene. The 2-aryl-5-alkyl-3-nitrothiophene is reduced by metals, such as iron, tin and zinc or catalytic hydrogenation. The preferred reduction occurs with iron in acetic acid at temperatures between 50–110° C. and preferrably at 100° C. for 5–30 min. After cooling to room temperature the reaction is diluted with water, neutralized with alkali, such as sodium hydroxide, potassium hydroxide, potassium carbonate or sodium bicarbonate, and extracted with a non-protic solvent such as diethyl ether, ethyl acetate or methylene chloride. The organic extracts are dried with agents such as $MgSO_4$ and $Na_2SO_4$ and the volatiles removed to provide the desired aminothiophene XVI.

Other desired aminoheterocycles can be prepared by methods known in the art and described in the literature. The examples that follow are illustrative and, as recognized by one skilled in the art, particular reagents or conditions could be modified as needed for individual compounds. Intermediates used in the schemes below are either commercially available or easily prepared from commercially available materials by those skilled in the art.

Scheme IV outlines a general scheme for desired aminofurans as described by Stevenson et al. (J. Am. Chem. Soc., 1937, 59, 2525). An ethyl aroylacetate (XVII) is dissolved in a non-protic solvent, such as ether or THF, and treated with a strong base, such as sodium, sodium ethoxide or sodium hydride, and the anion is reacted with a bromomethyl alkylketone (XVIII) at low temperatures, such as 0° C. After stirring the reaction until no starting material remains, it is poured onto cold water and extracted with a non-protic solvent. The combined extracts are dried with agents such as $MgSO_4$ or $Na_2SO_4$. The diketo-ester (XIX) may be carried forward without further purification or purified by distillation or silica gel chromatography. The diketo-ester in a protic solvent, such as ethanol, is heated in the presence of a mineral acid, such as sulfuric or hydrochloric, for 5–10 hr. and extracted with a non-protic solvent. The combined extracts are dried with agents such as $MgSO_4$ or $Na_2SO_4$. The furan-ester (XX) may be carried forward without further purification or purified by distillation or silica gel chromatography. The furan-ester in a protic solvent, such as ethanol, is treated with hydrazine hydrate and the mixture heated for 2–5 days. The hydrazide is isloated as above and treated with hot formic acid and the resulting furan-amine (XXI) purified by distillation or silica gel chromatography.

Scheme IV

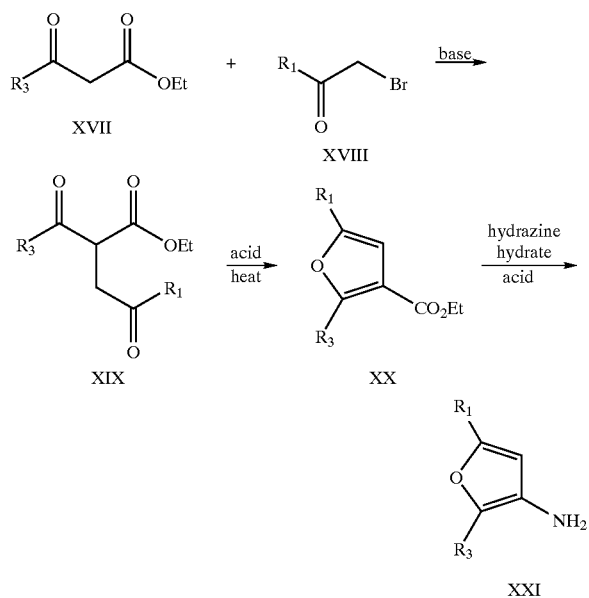

The synthesis of substituted 4-aminooxazoles may be achieved analogous to a procedure described by Lakhan et al. (J. Het. Chem., 1988, 25, 1413) and illustrated in Scheme V. A mixture of aroyl cyanide (XXII), aldeyde (XXIII) and anhydrous ammonium acetate in acetic acid is heated at 100–110° C. for 3–6 hr, cooled to room temperature and quenched with water. Extraction by a non-protic solvent provides the product XXIV which can be carried forward without further purification or purified by recrystallization or silica gel chromatography.

Scheme V

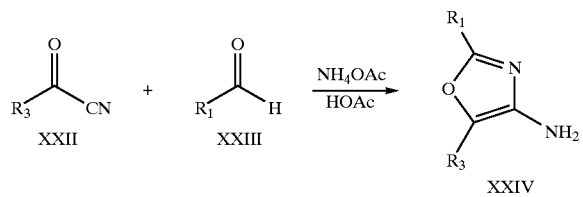

The synthesis of substituted 3-aminopyrroles (XXVIII) may be achieved in a manner analogous to Aiello et al., J. Chem. Soc. Perkins Trans. I, 1981, 1. This is outlined in Scheme VI. A mixture of aryldioxoalkane (XXV) and amine (XXVI) in acetic acid is heated at 100–110° C. for 3–6 hr and worked up in the usual manner. The product (XXVII) in acetic acid is treated with a nitrating agent, such as nitric acid and potassium nitrate in concentrated sulfuric acid. The mixture is poured onto cold water and extracted with a non-protic solvent. The combined extracts are dried with agents such as $MgSO_4$ and $Na_2SO_4$. Removal of the volatiles provides the nitro-pyrrole which which may be carried forward without further purification or purified by recrystallization or silica gel chromatography. The nitro-pyrrole is reduced to the amine with iron in acetic acid or by catalytic hydrogenation using palladium on activated carbon. The aminopyrrole (XXVIII) may be carried forward without further purification or purified by recrystallization or silica gel chromatography.

Scheme VI

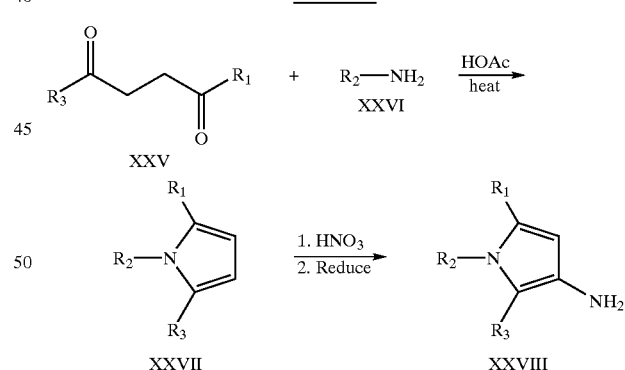

In an analogous fashion, a mixture of amine XXIX and 3-aryl-2,5-dioxoalkane (XXX) in acetic acid is heated between 80–110° C. for 2–24 hr. The reaction is diluted with water and extracted with an organic solvent. The combined extracts are dried with agents such as $MgSO_4$ or $Na_2SO_4$ and the volatiles removed. The resulting pyrrole is treated with a nitrating agent and subsequently reduced to XXXI as described above. The product may be carried forward without further purification or purified by recrystallization or silica gel chromatography. This process is illustrated in Scheme VII.

Scheme VII

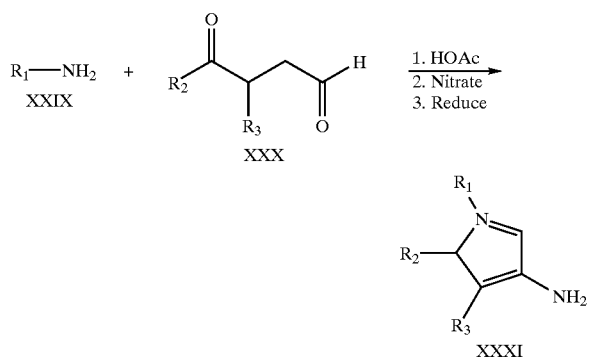

Substituted 5-aminothiazoles (XXXV) may be prepared in a manner analogous to Gerwald et al., *J. Prakt. Chem.* 1973, 315, 539. As illustrated in Scheme VIII, to a mixture of aminocyanide XXXII, aldehyde XXXIII and sulfur in an anhydrous solvent, such as ethanol and methanol, is added dropwise a base, such as triethylamine. The mixture is heated at 50° C. for 1–3 hr. The mixture is cooled and the excess sulfur removed. Acetic acid is added to neutralize the mixture and the solid collected. The imine XXXIV is treated with acid, such as hydrchloric and toluenesulfonic acid, in water and an organic solvent. After the starting material is consumed the reaction is worked up and the product XXXV may be carried forward without further purification or purified by recrystallization or silica gel chromatography.

Scheme VIII

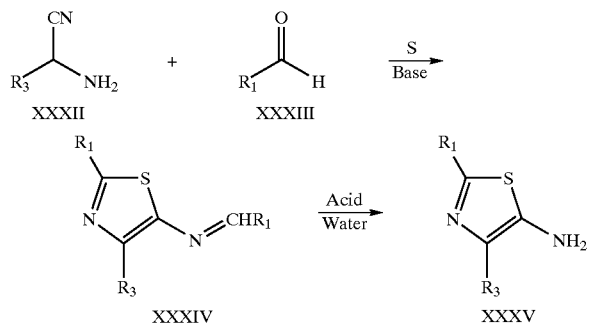

A synthesis of substituted 2-aminothiophenes (XXXVII), analous to a procedure described by Gewald et al. (*J. Prakt. Chem.*, 1973, 315, 539) is illustrated in Scheme IX. A mixture of disubstituted thiophene-3-carboxylic acid (XXXVI) in a protic solvent, such as acetic acid, at a temperature of 0–50° C. is treated with a nitrating agent, such as nitric acid or potassium nitrate in concentrated sulfuric acid. After the starting material has been consumed the reaction is poured onto ice and the product extracted with a non-protic solvent. The combined extracts are dried with agents such as $MgSO_4$ and $Na_2SO_4$ and the volatiles removed. The nitrothiophene is reduced to the amine with iron in acetic acid or by catalytic hydrogenation using palladium on activated carbon. The amino-thiophene may be carried forward without further purification or purified by recrystallization or silica gel chromatography.

Scheme IX

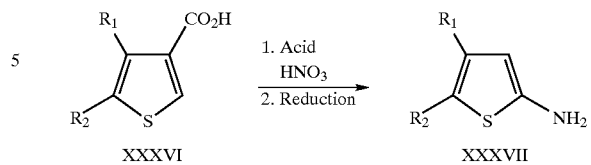

1,5-Disubstituted-3-aminopyrazoles (XL) may be prepared as shown in Scheme X, in a fashion analogous to the procedure described by Ege et al. (J. Het. Chem., 1982, 19, 1267). Potassium is added to anhydrous t-butanol and the mixture cooled to 5° C. Hydrazine XXXVIII is added, followed by cyanodibromoalkane XXXIX. The mixture is heated at refluxing temperatures for 3–10 hr. The mixture is cooled to room temperature and poured onto ice water. The product is extracted with an organic solvent. The combined extracts are dried with agents such as $MgSO_4$ or $Na_2SO_4$ and the volatiles removed. The product XL may be carried forward without further purification or purified by recrystallization or silica gel chromatography.

Scheme X

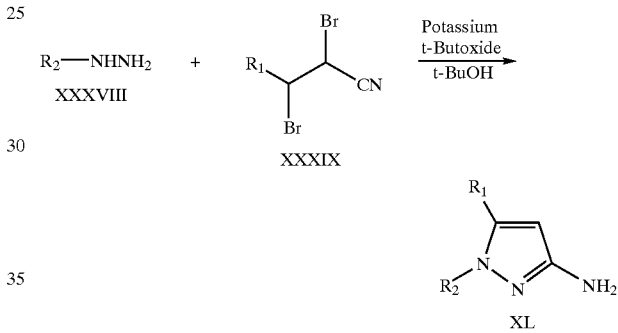

The synthesis of 2-amino-3,5-disubstituted thiophenes shown in Scheme XI, is done in a fashion analogous to Knoll et al., *J. Prakt. Chem.*, 1985, 327, 463. A mixture of substituted N-(3-aminothioacryloyl)-formamidine (XLI) and substituted bromide (XLII) in a protic solvent, such as methanol or ethanol, is heated, preferably at a reflux temperature, for 5–30 min and cooled below room temperature. The product thiophene-imine is filtered and dried. The thiophene-imine XLIII is converted to the thiophene-amine (XLIV) by treatment with aqueous acid.

Scheme XI

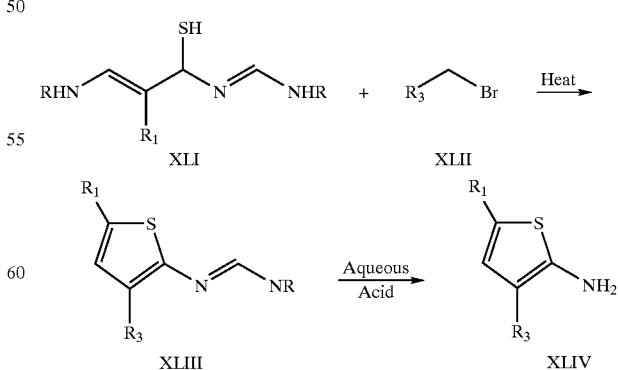

The synthesis of 1,4-disubstituted-2-aminopyrroles (XLVIII) may be accomplished in a manner analogous to Brodrick et al. (*J. Chem. Soc. Perkin Trans.* I, 1975, 1910), and as illustrated in Scheme XII. The potassium salt of formylnitrile XLV in water is treated with amine XLVI and acetic acid and the mixture heated at 50–90° C. for 5–30 min. The aminonitrile XLVII is collected by filtration upon cooling and then is stirred at room temperature with a base such as ethanolic potassium ethoxide for 2–5 hr and the volatiles removed. The residue is diluted with water and extracted with an organic solvent. The combined extracts are dried with agents such as $MgSO_4$ and $Na_2SO_4$ and the volatiles removed. The product (XLVIII) may be carried forward without further purification or purified by recrystallization or silica gel chromatography.

Scheme XII

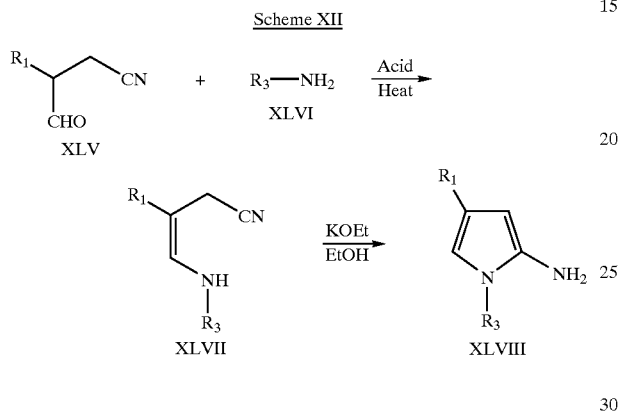

The preparation of 1,2-disubstituted-4-aminoimidazoles (L) by reduction of the corresponding nitro compound (XLIX), for example with iron in acetic acid or catalytic hydrogenation may be accomplished as described by Al-Shaar et al. (*J. Chem. Soc. Perkin Trans.* I, 1992, 2779) and illustrated in Scheme XIII.

Scheme XIII

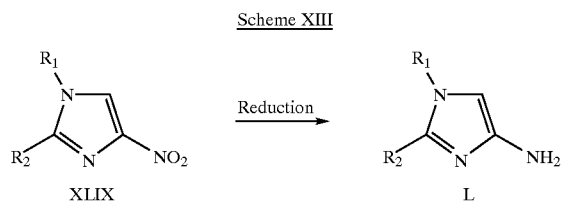

2,4-Disubstituted 5-aminooxazoles (LV) may be prepared in a manner analogous to the procedure described by Poupaert et al. (Synthesis, 1972, 622) and illustrated in Scheme XIV. Acid chloride LI is added to a cold mixture of 2-aminonitrile LII and a base such as triethylamine in a non-protic solvent, such as THF, benzene, toluene or ether. The preferred temperature is 0° C. The mixture is stirred for 12–24 hr and washed with water. The volatiles are removed and the product LIII treated with ethylmercaptan and dry hydrogen chloride in dry methylene chloride for 5–30 min. The solid 5-imino-1,3-oxazole hydrochloride (LIV) is collected by filtration, dissolved in dry pyridine and the solution saturated with hydrogen sulfide during 4 hr at 0° C. The mixture is diluted with an organic solvent and washed with water and dried. Removal of the volatiles provides the 5-amino-1,3-oxazole product (LV) which may be carried forward without further purification or be purified by silica gel chromatography.

Scheme XIV

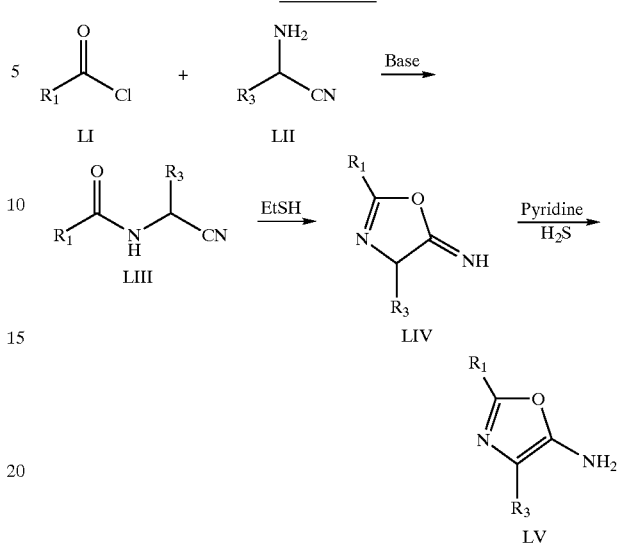

The synthesis of 1,4-disubstituted-2-aminopyrazoles may be accomplished as illustrated in Scheme XV and described in Lancini et al., *J. Het. Chem.*, 1966, 3, 152.

To a mixture of substituted aminoketone (LVI) and cyanamide in water and acetic acid was added aqueous sodium hydroxide until pH 4.5 is reached. The mixture is heated at 50–90° C. for 1–5 hr, cooled and basicified with ammonium hydroxide. The product LVII is collected by filtration and dried.

Scheme XV

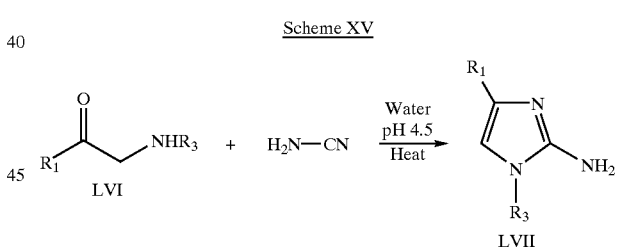

As in the cases described above, the synthesis of many other aminoheterocycles useful as intermediates may be accomplished by methods similar to those described in the literature or known to those skilled in the art. Several additional examples are illustrated in Scheme XVI. 2,5-Disubstituted-3-aminotriazoles (LVIII) have been described by Plenkiewicz et al. (*Bull. Chem. Soc. Belg.* 1987, 96, 675). 1,3-Disubstituted-4-aminopyrazoles (LIX) have been described by Guarneri et al. (*Gazz. Chim. Ital.* 1968, 98, 569). Damany et al. (*Tetrahedron*, 1976, 32, 2421) describe a 2-amino-3-substituted benzothiophene (LX). A 3-aminoindole (LXI) is described by Foresti et al. (*Gazz. Chim. Ital.*, 1975, 125, 151). Bristow et al. (*J. Chem. Soc.*, 1954, 616) describe an imidazo[1,2-a]pyridin-2-yl amine (LXII).

Scheme XVI

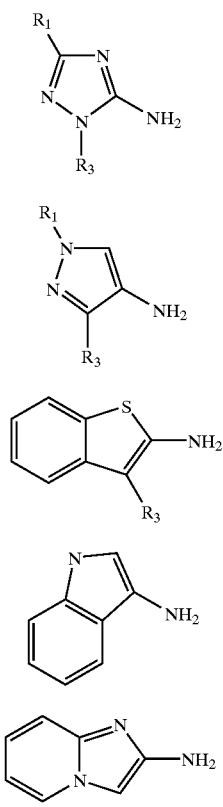

METHODS OF THERAPEUTIC USE

The compounds of the invention effectively block inflammatory cytokine production from cells. The inhibition of cytokine production is an attractive means for preventing and treating a variety of disorders associated with excess cytokine production, e.g., diseases and pathological conditions involving inflammation. Thus, the compounds of the invention are useful for the treatment of such conditions. These encompass chronic inflammatory diseases including, but not limited to, osteoarthritis, multiple sclerosis, Guillain-Barre syndrome, Crohn's disease, ulcerative colitis, psoriasis, graft versus host disease, systemic lupus erythematosus and insulin-dependent diabetes mellitus. The compounds of the invention can also be used to treat other disorders associated with the activity of elevated levels of proinflammatory cytokines such as responses to various infectious agents and a number of diseases of autoimmunity such as rheumatoid arthritis, toxic shock syndrome, diabetes and inflammatory bowel diseases unrelated to those listed above are discussed in the Background of the Invention.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of formula(I) may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)).

Dosage levels and requirements are well-recognized in the art and may be selected by those of ordinary skill in the art from available methods and techniques suitable for a particular patient. Reference in this regard may be made to U.S. provisional application No. 60/339,249. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be

SYNTHETIC EXAMPLES

Example 1

Synthesis of 1-[5-(2-Hydroxy-1,1-dimethyl-ethyl)-tolyl-2H-pyrazol-3-yl]-3-[4-(2-morpholin-4-yl-ethoxy)-naphthalen-1yl]-urea

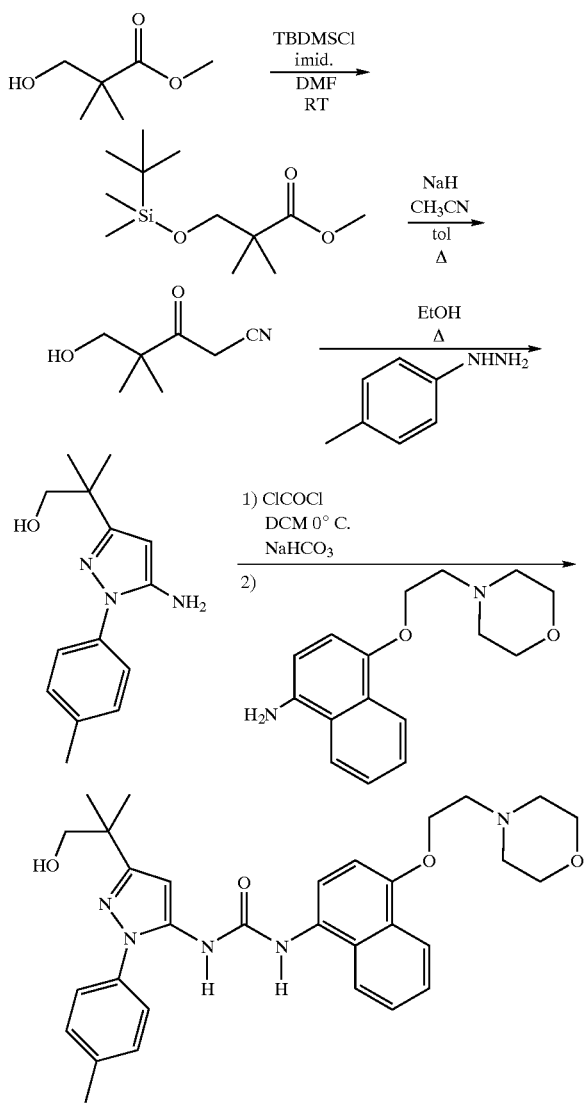

1

A round bottom flask was charged with methyl-2,2,-dimethyl-3-hydroxypropionate (4.22 g, 31.9 mmol) and 60 mL of anhydrous DMF. Imidazole (3.26 g, 47.8 mmol, 1.5 equiv.) and tert-butyl-dimethylsilyl chloride (5.77 g, 38.3 mmol, 1.2 equiv.) were then added. The mixture was left stirring under inert atmosphere for 12 h, then quenched with water (200 mL) and extracted three times with ether. The combined organic extracts were washed with water and brine, then dried (MgSO$_4$) and filtered. Removal of solvent in vacuo afforded 8.25 g of the silyl ether as a colorless oil (quantitative yield) of reasonable purity by $^1$H NMR to allow use as is for the next reaction.

To a suspension of NaH (60% in mineral oil, 550 mg, 13.7 mmol, 1.4 equiv.) in 17 mL anhydrous toluene at reflux was added dropwise a solution of the above silyl ether (2.44 g, 9.90 mmol) and acetonitrile (0.72 mL, 13.9 mmol, 1.4 equiv.) in 8.0 mL toluene. After addition was complete (~1 h) the mixture was refluxed for a further 5 h, then allowed to cool to ambient temperature. Dilute aqueous HCl was then added to raise the pH to ~4, and the product was extracted with EtOAc twice. The combined organic extracts were washed twice with brine, dried (Na$_2$SO$_4$), filtered and the solvent was removed in vacuo. A crude pale yellow oil was obtained (1.10 g) which was a mixture consisting mostly of the desired de-silylated beta-keto-nitrile. This was used without purification in the next step.

A round bottom flask was charged with the above beta-keto-nitrile (500 mg, 3.55 mmol), 20 mL EtOH, and para-tolyl-hydrazine hydrochloride (563 mg, 3.55 mmol, 1.0 equiv.). The mixture was refluxed for 18 h, then allowed to cool, quenched with saturated aqueous NaHCO$_3$ solution and extracted with EtOAc. The combined organic extracts were washed with brine, dried (Na$_2$SO$_4$), filtered and the solvent was removed in vacuo. The desired pyrazolamine was obtained as an orange oil (689 mg, 2.81 mmol, 79%), which was clean by $^1$H NMR and used as is for the next reaction.

4-(2-Morpholin-4-yl-ethoxy)naphthalen-1-yl amine (266 mg, 0.98 mmol) was dissolved in 15 mL CH$_2$Cl$_2$ and 15 mL saturated aqueous NaHCO$_3$ solution was added. The mixture was cooled to 0° C. and the organic layer was treated with phosgene (20% in toluene, 1.5 mL, 2.9 mmol), which was added in one portion via syringe while the mixture was not stirring. After 20 min, stirring was stopped, the layers were separated and the aqueous layer was extracted with one portion of CH$_2$Cl$_2$. The combined organics were dried over Na$_2$SO$_4$, filtered and the CH$_2$Cl$_2$ was removed in vacuo. To this isocyanate residue in toluene was then added the above pyrazolamine (240 mg, 0.98 mmol) dissolved in 7 mL anhydrous THF and the mixture was left stirring at room temperature for 2 h. The solvent was removed in vacuo and the product urea was purified by column chromatography on silica gel, eluting with 5% MeOH in CH$_2$Cl$_2$. The resulting tan foam was recrystallized from ether/hexanes to afford 30 mg of the title compound in >95% purity.

Example 2

Synthesis of 1-(5-tert-Butyl-2-p-tolyl-2H-pyrazol-3-yl)-3-{4-[2-(4-oxy-morpholin-4-yl)-ethoxy]-naphthalen-1-}yl-urea

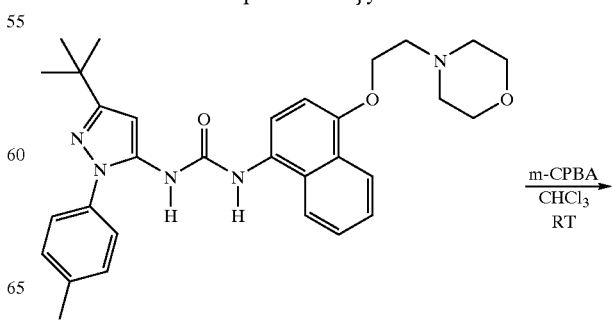

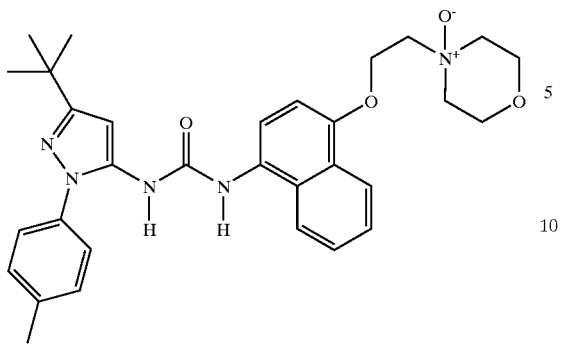

1-[5-tert-Butyl-2-p-tolyl-2H-pyrazol-3-[4-(2-morpholin-4-yl-ethoxy)naphthalen-1-yl]-urea (250 mg, 0.47 mmol) was dissolved in 0.5 mL CHCl₃ and cooled to 0° C. A solution of m-chloro-perbenzoic acid (m-CPBA) (82 mg, 0.47 mmol) in 0.5 mL CHCl₃ was added dropwise and the solution was stirred at 0° C. for 30 min. The resulting pink mixture solidified and was allowed to reach room temperature. Thin layer chromatography (100% EtOAc) indicated no starting material. This solid was suspended in ~5 mL CHCl₃, loaded onto a basic alumina column and eluted with 3:1 CHCl₃:MeOH. The resulting solid was triturated with warm (40° C.) EtOAc to afford 70 mg of the title compound, m.p. 191° C. (dec.).

Example 3

Synthesis of 1-[5-tert-Butyl-2-(3-hydroxy-4-methyl-phenyl)-2H-4pyrazol-3-yl]-3-[4-(2-morpholin-4yl-ethoxy)-naphthalen-1yl]-urea

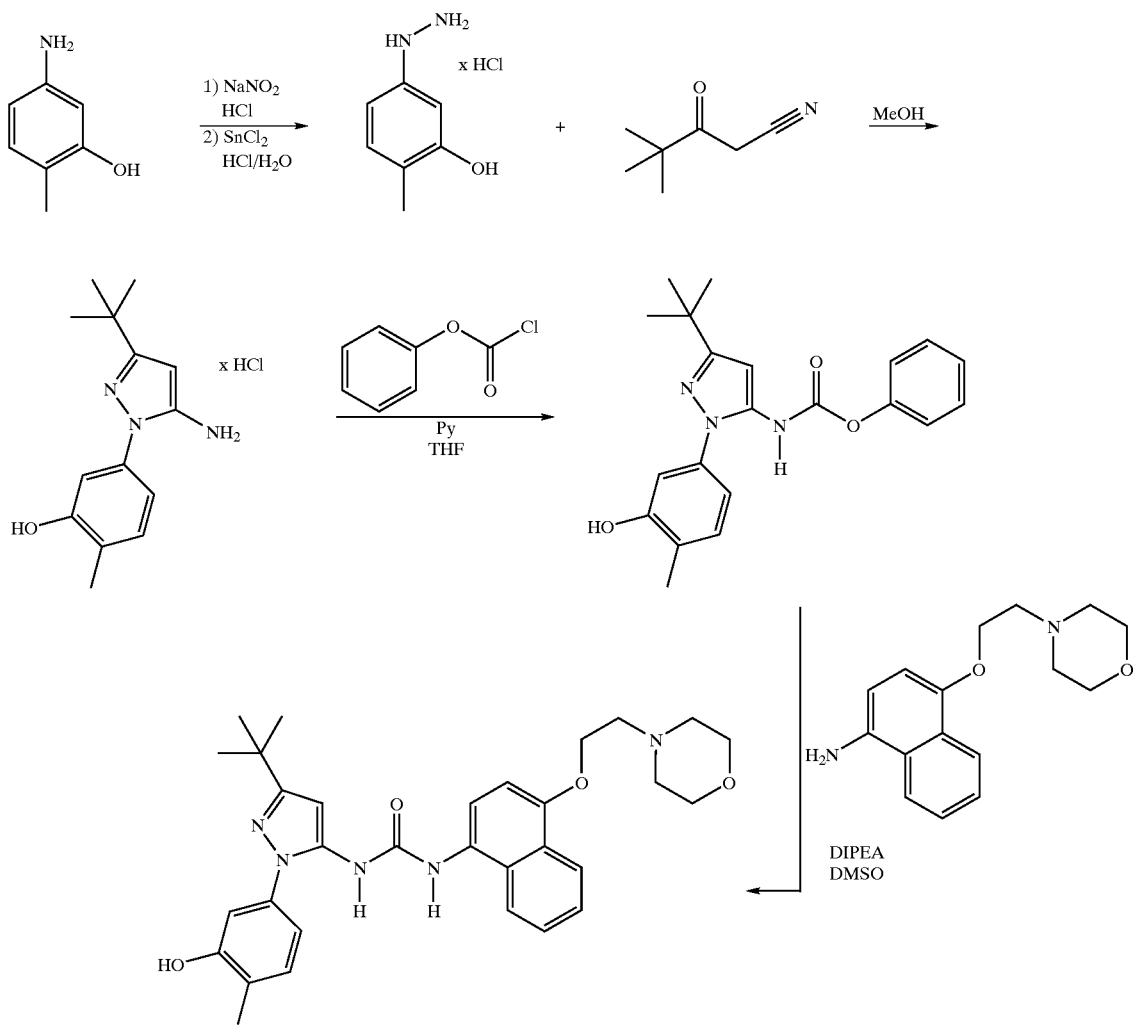

5-Amino-o-cresol (6.22 g, 50 mmol) was placed in a 250 mL round bottom flask together with 10 g ice. The material was cooled to −10° C. and 15 mL concentrated HCl was added. To this slurry was added a solution of sodium nitrite (3.45 g, 50 mmol) in 10 mL of water at −10° C. via pipette, the addition being done over 30 min. The yellow slurry turned to a dark solution. In another flask tin(II) chloride dihydrate (30.0 g, 133 mmol) was dissolved in 30 mL of concentrated HCl diluted with 30 mL of water, resulting in a clear, colorless solution, which was cooled to 0° C. To this tin solution was added the diazonium slurry and the mixture was stirred overnight. A white precipitate of crude hydrazine hydrochloride salt was obtained after cooling to −15° C. This was isolated by filtration with a Buchner funnel, and washed with hexanes (2×20 mL) to afford 12.60 g of a white solid.

The hydrazine hydrochloride salt obtained above was placed in a 250 mL round bottom flask. MeOH (200 mL) was added as well as 4,4-dimethyl-3-oxo-pentanenitrile (7.50 g, 60 mmol) and the mixture was stirred at room temperature over the weekend. The solvent was distilled off and the left over brown slurry was diluted with 100 mL EtOAc and stirred 15 min. Filtration and washing with 100 mL of hexanes affords 3.03 g of the desired pyrazolamine hydrochloride salt as an off-white solid.

A magnetically stirred slurry of the above pyrazolamine hydrochloride salt (1.41 g, 5.0 mmol) in 20 mL anhydrous THF under inert atmosphere was treated dropwise with excess pyridine until all solids were dissolved (3.0 mL). The solution was then cooled to −15° C. and phenyl chloroformate (0.70 mL, 6.7 mmol) was added dropwise over 2 min. The cooling bath was removed, the mixture allowed to reach room temperature and stir 1.5 h. HPLC showed 45% conversion to the desired phenyl carbamate, with 25% starting material and 20% byproduct from double addition of chloroformate. The reaction was quenched with 50 mL of water and extracted 3 times with EtOAc. The combined organic extracts were washed with water and brine, dried ($Na_2SO_4$) and filtered. Removal of solvents in vacuo afforded 2.74 g of a yellow oil. This was immediately used as is for urea formation by mixing with 4-(2-morpholin-4-yl-ethoxy)naphthalen-1-yl amine (1.10 g, 4.0 mmol) and N,N-diisopropyl-ethylamine (0.75 mL, 4.2 mmol) in 30 mL anhydrous DMSO. This mixture was heated at 50° C. for 3 h, then cooled to room temperature, quenched with water and extracted with EtOAc. The title compound (0.72 g) was isolated as a white solid by purification with silica gel column chromatography eluting with EtOH in $CH_2Cl_2$, followed by trituration from hot hexanes.

Example 4

Synthesis of 1-[5-tert-Butyl-2-(2-hydroxy-4-methyl-phenyl)-2H-pyrazol-3-yl]-3-[4-(2-morpholin-4-yl-ethoxy)-naphthalen-1-yl]-urea

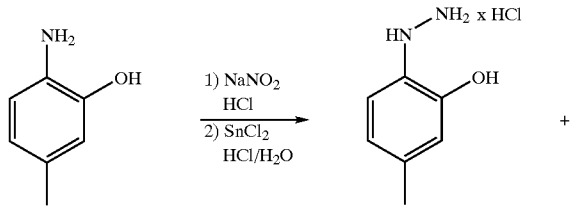

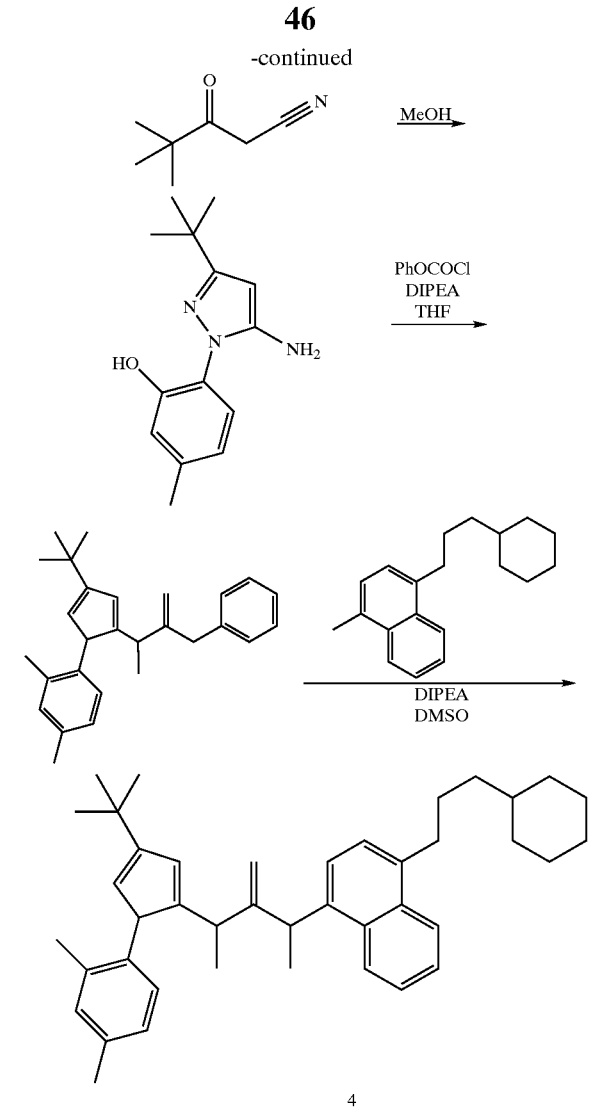

6-Amino-m-cresol (6.22 g, 50 mmol) was placed in a 250 mL round bottom flask together with 10 g ice. The material was cooled to −10° C. and 15 mL concentrated HCl was added. The color of the solid changed from yellow to grey. To this slurry was added a solution of sodium nitrite (3.45 g, 50 mmol) in 10 mL of water at −10° C. via pipette, the addition being done over 30 min. The slurry turned to a purple color. In another flask tin(II) chloride dihydrate (30.0 g, 133 mmol) was dissolved in 60 mL of 6 N HCl, resulting in a clear, colorless solution, which was cooled to 0° C. To this tin solution was added the diazonium salt and the mixture turned yellow immediately, then white. It was stirred overnight. After cooling to −20° C., the white precipitate of crude hydrazine hydrochloride salt was collected by filtration with a Buchner funnel, and washed with brine to afford 12.0 g of the desired hydrazine salt as a white solid.

The above hydrazine salt was dissolved in 150 mL MeOH and 4,4-dimethyl-3-oxo-pentanenitrile (7.50 g, 60 mmol) was added. The mixture was stirred at room temperature overnight. The solvent was distilled off in vacuo at ~30° C., and the residual brown slurry was diluted with 100 mL EtOAc. Water (20 mL) was added and $NaHCO_3$ solid until pH ~7. Filtration through diatomaceous earth afforded a red solution that was then loaded on Silica gel and eluted with 30% EtOAc in hexanes. The desired of pyrazolamine (0.85 g) was isolated as a yellow oil.

A magnetically stirred solution of the above pyrazolamine (0.75 g, 3.0 mmol) in 10 mL anhydrous THF under inert atmosphere was cooled to −10° C. and phenyl chloroformate (0.30 mL, 3.0 mmol) was added dropwise. The mixture was allowed to stir 2 h at 0° C. HPLC showed 50% conversion to the desired phenyl carbamate, with very little formation of bis-carbamate. N,N-diisopropyl-ethylamine (0.33 mL, 2.0 mmol) was added and formation of bis-carbamate was observed by HPLC before starting the starting pyrazolamine was completely consumed. The reaction was quenched with 50 mL of water and extracted 3 times with EtOAc. The combined organic extracts were washed with water and brine, dried (Na$_2$SO$_4$) and filtered. Removal of solvents in vacuo afforded 1.20 g of an orange oil. This was immediately used as is for urea formation by mixing with 4-(2-morpholin-4-yl-ethoxy)naphthalen-1-yl amine (0.34 g, 1.2 mmol) and N,N-diisopropyl-ethylamine (0.25 mL, 1.2 mmol) in 10 mL anhydrous DMSO. This mixture was heated at 50° C. for 2 h, then cooled to room temperature, quenched with water and extracted with EtOAc as before. The title compound was isolated as yellow-brown crystals (0.45 g) and was purified by dissolution in a minimum amount of EtOAc, followed by precipitation by addition of hexanes and filtration providing the product as white crystals (0.170 g).

Example 5

Synthesis of 4-(3-tert-Butyl-5-{3-[4-(2-morpholin-4-yl-ethoxy)-naphthalen-1-yl]-ureido}-pyrazol-1-yl)-benzoic Acid

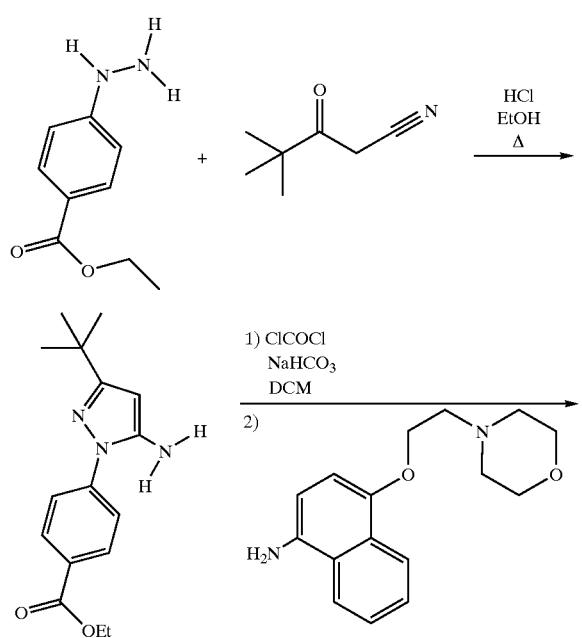

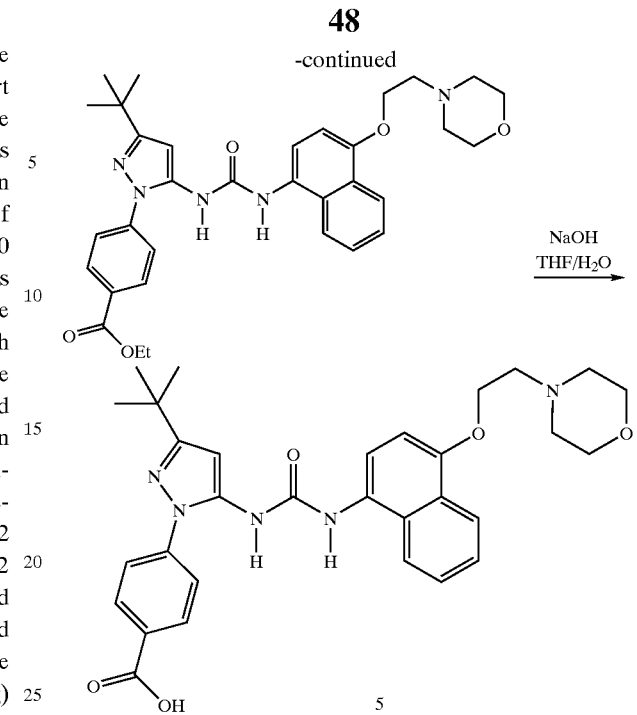

4-Hydrazino-benzoic acid ethyl ester (0.50 g, 2.77 mmol) was dissolved in 70 mL EtOH. 4,4-Dimethyl-3-oxo-pentanenitrile (0.35 g, 2.80 mmol) was then added, as well as 0.25 mL concentrated HCl. The mixture was gently refluxed overnight. Volatiles were then removed in vacuo and the product was purified by column chromatography on silica gel eluting with 15% EtOAc in petroleum ether to afford the desired pyrazolamine as a colorless solid (0.43 g, 54% yield).

4-(2-Morpholin-4-yl-ethoxy)naphthalen-1-yl amine is dissolved in equal amounts of CH$_2$Cl$_2$ and saturated aqueous NaHCO$_3$ solution. The mixture is cooled to 0° C. and the organic layer is treated with phosgene (20% in toluene), which is added in one portion via syringe while the mixture is not stirring. After 20 min stirring is stopped, the layers are separated and the aqueous layer is extracted with one portion of CH$_2$Cl$_2$. The combined organics are dried over Na$_2$SO$_4$, filtered and the CH$_2$Cl$_2$ is removed in vacuo. To this isocyanate residue in toluene is then added the above pyrazolamine dissolved in anhydrous THF and the mixture is left stirring at room temperature for 2 h. The solvent is removed in vacuo and the product urea is purified by column chromatography on silica gel using MeOH in CH$_2$Cl$_2$ as eluent.

The above urea is dissolved in THF and an equivalent volume of 0.5 M solution of LiOH in water is added. The resulting homogeneous mixture is stirred for three h until all ester is cleaved to the acid. Volatiles are evaporated, then 10% HCl in water is added and the product extracted with EtOAc. Purification by column chromatography and recrystallization affords title compound.

Example 6

Synthesis of 1-[5-tert-Butyl-2-(4-hydroxymethyl-phenyl)-2H-pyrazol-3-yl]-3-(4-(2-morpholin-4-yl-ethoxy)-naphthalen-1-yl]-urea

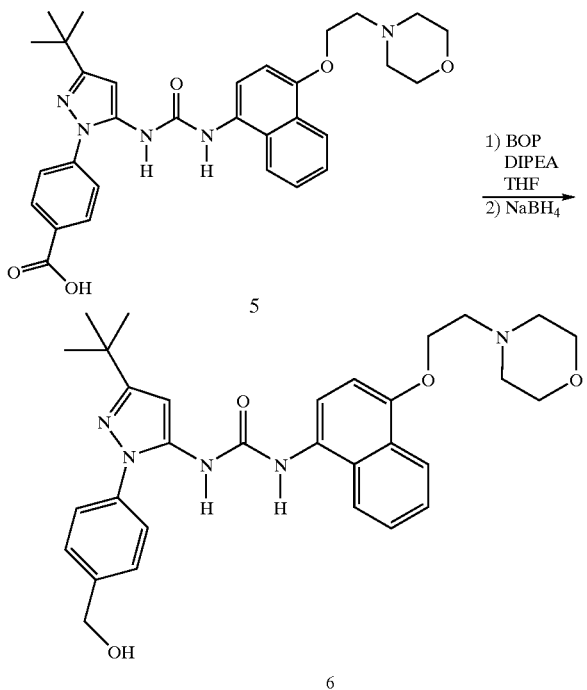

The benzyl-alcohol derivative 6 can be obtained by applying the method by R. P. McGeary *Tetrahedron Lett.* 1998, 39, 3319–3322.

N,N-diisopropyl-ethylamine (1.2 equiv.) is added to a stirred suspension of the urea acid 5 (1 equiv.) and benzotriazol-1-yloxy tris(dimethylamino)-phosphonium hexafluorophosphate (BOP reagent, 1.1 equiv.) in THF at room temperature. The resulting solution is stirred for 5 min, then NaBH$_4$ (1 equiv.) is added. After stirring for 20 min, the mixture is diluted with EtOAc, washed with 5% aqueous HCl, then saturated NaHCO$_3$ and brine. The organics are dried (Na$_2$SO$_4$), filtered and the solvent removed in vacuo to afford the title compound, which may be purified by column chromatography on silica gel.

Example 7

Synthesis of 1-(5-tert-Butyl-2-p-tolyl-2H prazol-3-yl)-3-[4-(2-morpholin-4-yl-2-oxo-ethoxy)-naphthalen-1-yl]-urea

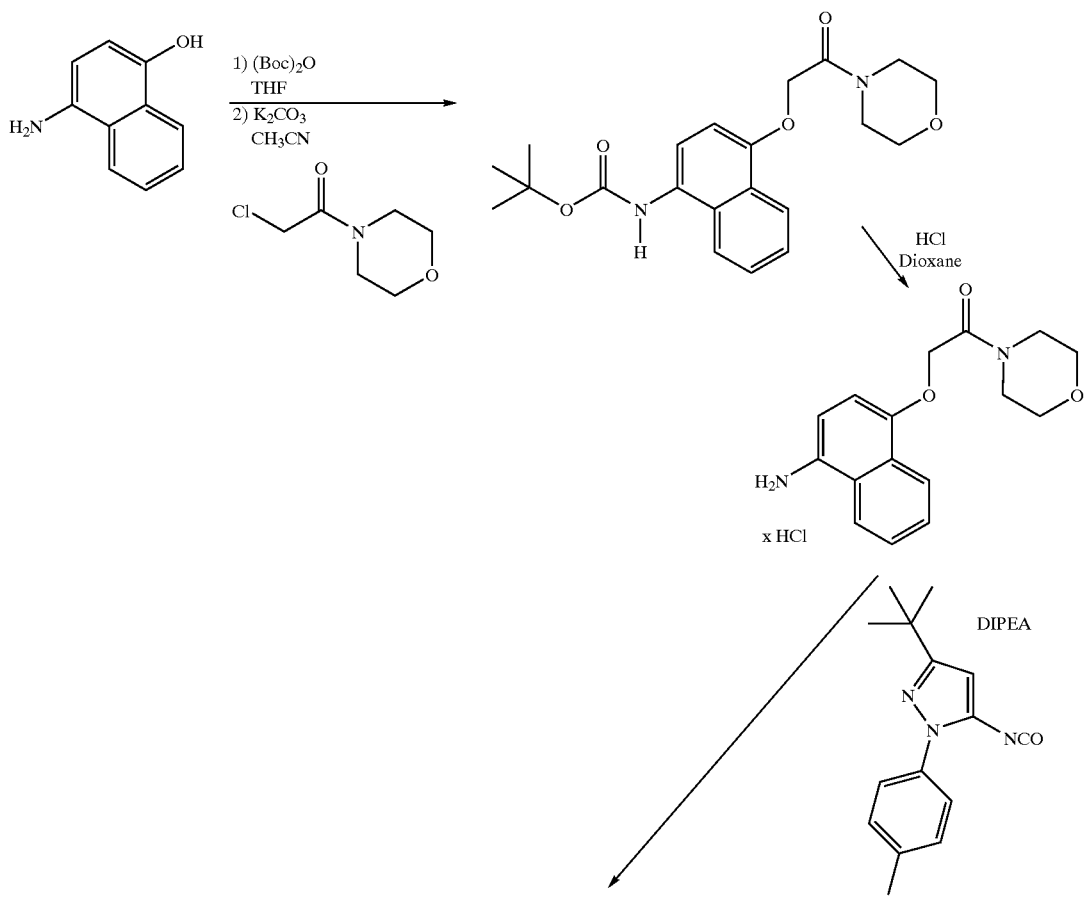

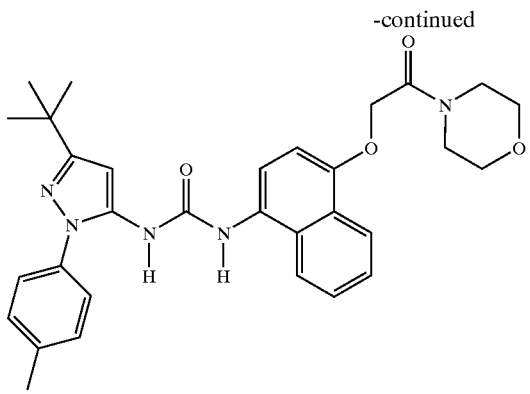

7

To a solution of 4-amino-naphth-1-ol hydrochloride (5.0 g, 25.6 mmol) in 25 mL THF at 0° C., potassium tert-butoxide solution (1 M in THF, 25.6 mL, 25.6 mmol) was added dropwise. After the addition was complete di-tert-butyl-dicarbonate (5.59 g, 25.6 mmol) was added in portions. The reaction mixture was left to warm to room temperature and stir overnight. The volatiles were then removed in vacuo, EtOAc was added and the organic layer was washed with water and brine, then dried (MgSO₄). Recrystallization from hexanes/EtOAc afforded 3.78 g of the N-Boc-aminonaphthol.

The N-Boc-aminonaphthol from above (436 mg, 1.7 mmol) was mixed with morpholine alpha-chloro acetamide (303 mg, 1.9 mmol), (made from mixing a solution of 0.55 mL morpholine in 5 mL of anhydrous ether at 0° C. with chloroacetyl chloride, followed by collection of the precipitate by vacuum filtration), and potassium carbonate (702 mg, 5.1 mmol) in 10 mL acetonitrile. The mixture was stirred for 4 h at 80° C., then allowed to cool, diluted with 15 mL EtOAc, washed with water and brine, dried (MgSO₄) and concentrated in vacuo. The residue was purified by column chromatography on silica gel to afford 350 mg of the desired ether.

The ether from above (259 mg, 0.67 mmol) was dissolved in 4.0 mL CH₂Cl₂ and treated at room temperature with HCl (4 M in 1,4-dioxane, 0.7 mL). The reaction was allowed to stir for 2 days. A precipitate formed. The solid was filtered and washed with dioxane to afford the aminonaphthyl ether hydrochloride salt (184 mg) as a gray solid.

To the above aminonaphthyl ether hydrochloride salt (154 mg, 0.48 mmol) in 4 mL anhydrous THF were added N,N-diisopropyl-ethylamine (0.37 mL, 1.7 mmol) and the pyrazole isocyanate (made from pyrazole and phosgene). The reaction mixture was left stirring over the weekend, then the solvent was removed and the residue was taken up in MeOH. The title compound precipitated as an off-white solid (100 mg).

Example 8

Synthesis of 1-[5-(1,1-Dimethyl-2-oxo-ethyl)-2-p-tolyl-2H-pyrazol-3-yl]-3-[4-(2-morpholin-4-yl-ethoxy)-naphthalen-1-yl]-urea

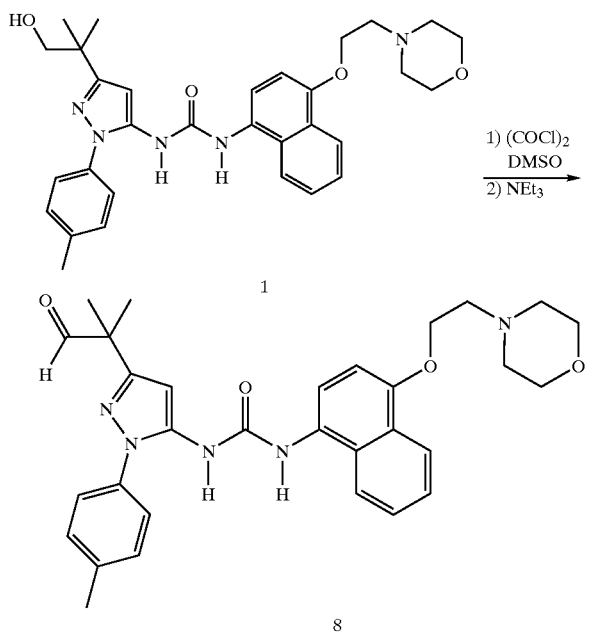

The title compound may be prepared by standard Swern oxidation (K. Omura and D. Swern, *Tetrahedron*, 1978, 34, 1651–1660) of the product of Example 1.

Example 9

Synthesis of 2-Methyl-2-(5-{3-[4(2-morpholin-4-yl-ethoxy)-naphthalen-1-yl]-ureido}-1-p-tolyl-1H-pyrazol-3-yl)-propionic Acid

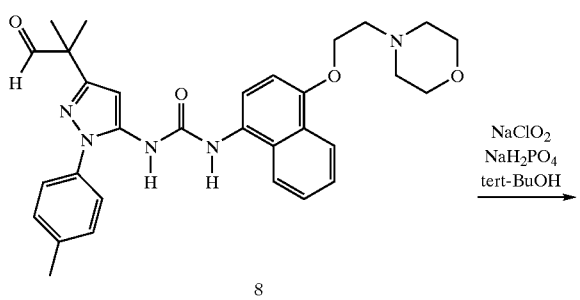

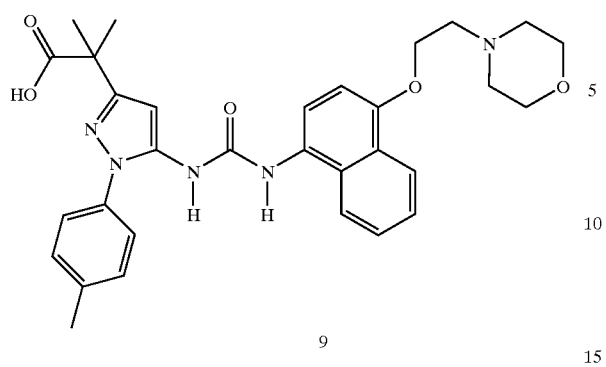

9

The title compound may be prepared by oxidation of the product of Example 8 (for a procedure see, for example: M. G. Constantino et al., *Synth. Commun.* 2000, 30 (18), 3327–3340).

Example 10

Synthesis of 1-(5-tert-Butyl-2-p-tolyl-2H-pyrazol-3-yl)-3-{4-[2-(3-oxo-morpholin-4-yl)-ethoxy]-naphthalen-1-yl}-urea

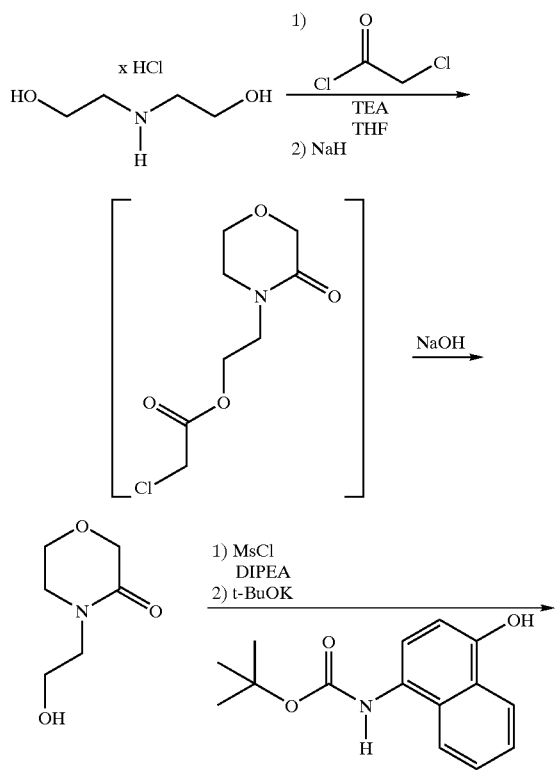

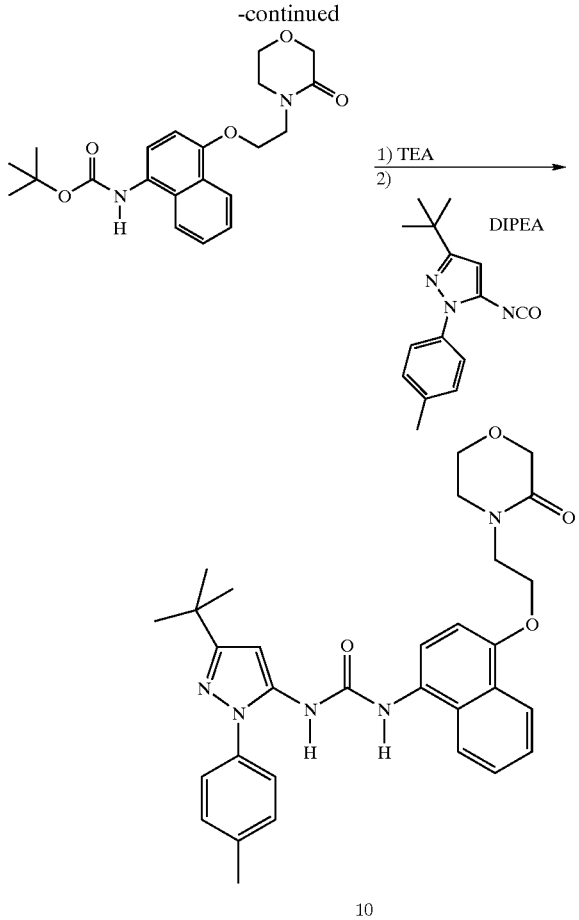

10

Diethanolamine hydrochloride is suspended in anhydrous THF and treated at 0° C. with triethylamine (3 equiv.) and dropwise with chloroacetyl chloride (2 equiv.). The mixture is allowed to reach room temperature and stir for 6 h to bis-protect at O and N. In the same pot a slight excess of sodium hydride is added, and the mixture is refluxed for hours to cyclize to the morpholinone ring intermediate (see *Tetrahedion Lett.*, 1999, 7227). Finally 2 N aqueous NaOH is added and refluxing is continued to O-deprotect. The mixture is cooled, the volatiles removed in vacuo and the hydroxyethylmorpholinone isolated from column chromatography on silica gel (dichloromethane/MeOH eluent mixture). This intermediate is treated with methane sulfonyl chloride and base to afford the methyl sulfonate, which is reacted with N-Boc-4-amino-1-naphthol as described in Example 7 to afford the naphthyl ether intermediate. After deprotection, reaction as in Example 7 with the pyrazole isocyanate forms the title compound.

Example 11

Synthesis of 1-(5-tert-Butyl-2-p-tolyl-2H-pyrazol-3-yl)-3-{4-[2-(1-oxo-1$\lambda^4$-thiomorpholin-4-yl)-ethoxy]-naphthalen-1-yl}-urea

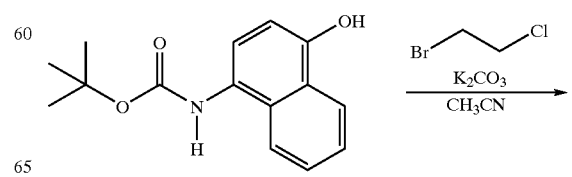

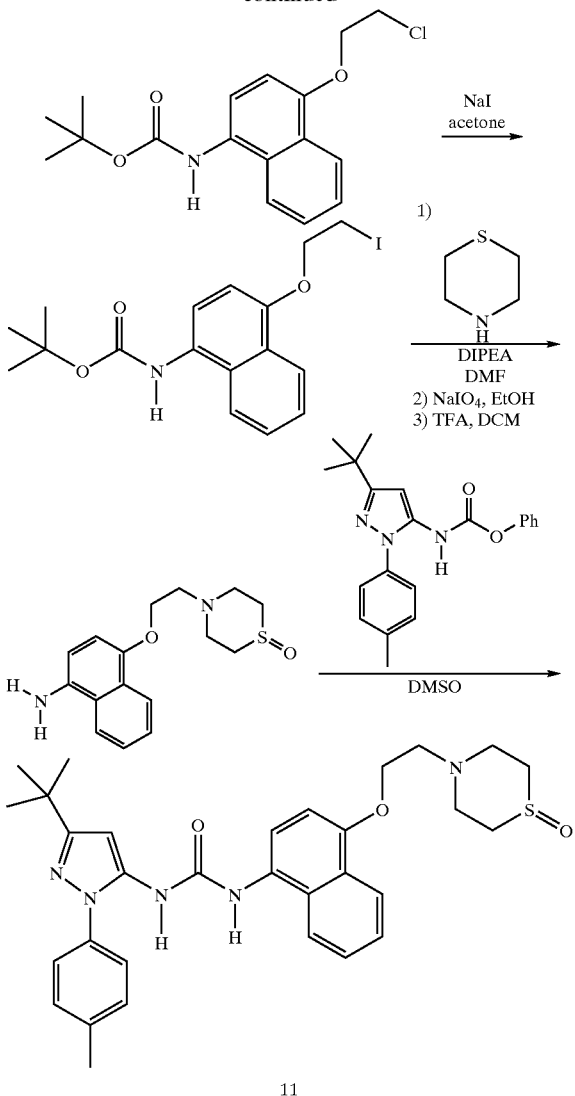

To N-Boc-4-amino-naphthalene-1-ol (5.0 g) and potassium carbonate (13.3 g) suspended in 100 mL anhydrous acetonitrile was added bromochloroethane (5.5 g, 38.6 mmol). The resulting brown suspension was heated to 80° C. overnight. After cooling, the reaction mixture was partitioned between EtOAc and water. The organic phase was washed with brine and dried (MgSO$_4$). After filtration the solvent was removed in vacuo and the product purified by column chromatography on silica gel (25% EtOAc in hexanes), then by recrystallization. The desired chloroethyl ether was obtained as a tan solid (1.98 g).

The above chloroethyl ether (3.30 g, 10.2 mmol) was dissolved in 30 mL dry acetone and treated with 15 g (102 mmol) of NaI. The orange suspension was heated to reflux for 64 h. After cooling, 50 mL dichloromethane were added and precipitated salts were filtered off. The solvent was removed and the residue was partitioned between dichloromethane and water. The organic portion was dried (Na$_2$SO$_4$), filtered and the solvent removed providing the iodoethyl ether as a beige solid (4.03 g). The iodoethyl ether (1.0 g, 2.4 mmol) was dissolved in 5 mL DMF and treated with N,N-diisopropyl-ethyl amine (0.31 g, 2.4 mmol) and thiomorpholine (0.25 g, 2.4 mmol). The mixture was stirred at 40° C. overnight, then cooled and partitioned between Et$_2$O and water. The organic phase was washed with water and brine, then dried (MgSO$_4$) and filtered. Removal of solvent, followed by column chromatography, afforded 726 mg of a colorless solid. This material was suspended in 50 mL EtOH, cooled to 0° C., treated with NaIO$_4$ (417 mg) and left stirring at room temperature for 2 days. The solvent was removed, the residue partitioned between EtOAc and water and the organic layer was washed with brine and dried (MgSO$_4$). Filtration, removal of solvent and purification by chromatography afforded 451 mg of sulfoxide. This material was dissolved in 5 mL dichloromethane, treated with trifluoroacetic acid (0.43 mL) and stirred at room temperature overnight. Powdered K$_2$CO$_3$ (770 mg) was then added and after stirring 0.5 h the solids were filtered off and the solvent removed to afford the desired naphthylamine intermediate as a purple residue (318 mg).

Pyrazolamine carbamate (173 mg, made analogously to the pyrazole carbamates in Examples 3 and 4) and the above naphthylamine intermediate (100 mg) were combined in 1 mL DMSO and stirred two days. The mixture was partitioned between EtOAc and water. The organic layer was washed with water and brine, then dried (MgSO$_4$). Filtration, removal of solvent and purification by chromatography afforded the title compound as a yellow solid (80 mg).

Example 12

Synthesis of 1-[5-tert-Butyl-2-(6-methyl-1-oxy-pyridin-3-yl)-2H-pyrazol-3-yl]-3-[4-(2-morpholin-4-yl-ethoxy)-naphthalen-1-yl]-urea

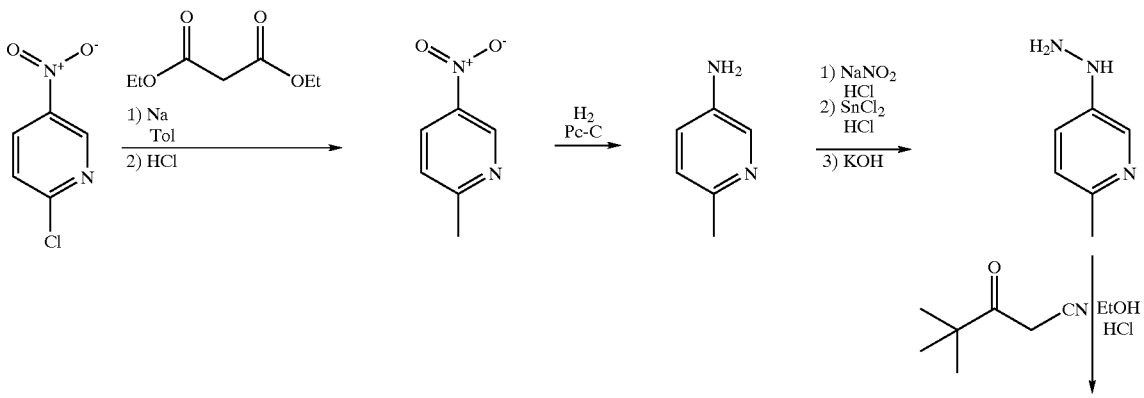

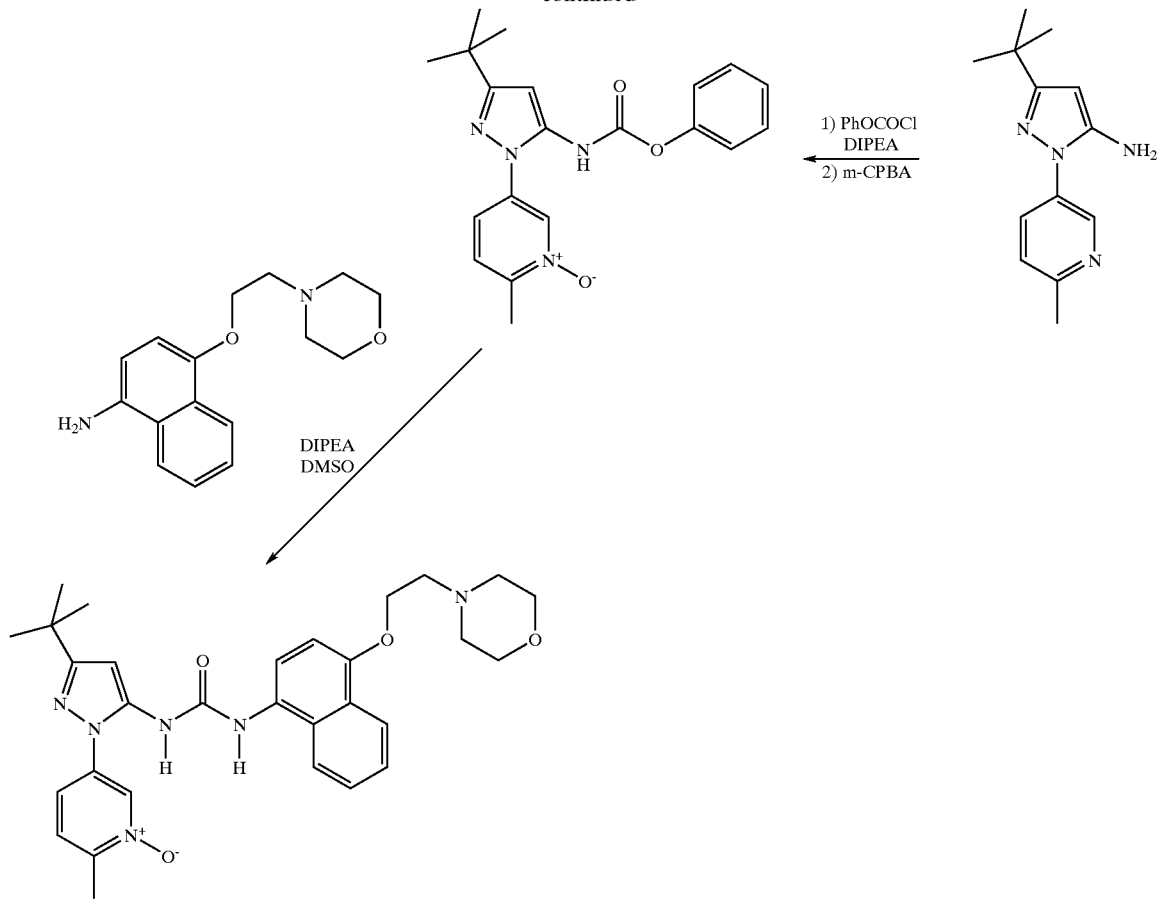

12

A slurry of diethyl malonate (42 mL, 0.28 mol) and sodium (4.71 g, 0.20 mol) was warmed slowly to 90° C. The slurry was stirred at 90° C. for 2 h, at 120° C. for 30 min before being cooled to room temperature. Toluene (200 mL) and 2-chloro-5-nitropyridine (25.0 g, 0.16 mmol) were added and the slurry was heated at 110° C. for 1.5 h at ambient temperature for 17 h. After evaporation of the volatiles, 6 N HCl (200 mL) was added, the slurry was heated to reflux for 4 h and then cooled to room temperature. The solution was neutralized with solid sodium carbonate, extracted with BtOAc (6×100 mL), dried over solid magnesium sulfate, and concentrated to a dark solid. This material was flashed through a plug of silica gel (2"×2", eluant =20% EtOAc/petroleum ether) to afford 2-methyl-5-mitropyridine as a tan solid (15.2 g).

2-Methyl-5-nitropyridine from above (13.0 g, 94.1 mmol) was dissolved in 1,4-dioxane (150 mL). The catalyst (10% Pd/C, 100 mg) was added prior to assembling the Parr apparatus. Hydrogenation at 50 psi for 24 h, filtration over diatomaceous earth and evaporation of the volatiles afforded 5-amino-2-methyl-pyridine (9.90 g) as a tan solid.

5-Amino-2-methyl-pyridine (9.90 g, 91.6 mmol) was dissolved in 6 N HCl (100 mL), cooled to 0° C., and vigorously stirred throughout the procedure. Sodium nitrite (6.32 g, 91.6 mmol) was dissolved in water (50 mL), this solution was added to the reaction solution. After 30 min, tin (II) chloride dihydrate (52.0 g, 230 mmol) in 6 N HCl (100 mL) was added, and the reaction slurry was stirred at 0° C. for 3h. The pH was adjusted to pH 14 with 40% aqueous potassium hydroxide solution. EtOAc extractions (6×250 mL), drying the organics over solid magnesium sulfate, and concentration afforded 5-hydrazino-2-methyl-pyridine as a tan solid (8.0 g). This material was used directly without further purification.

A solution of 5-hydrazino-2-methyl-pyridine (8.0 g, 65.0 mmol) and 4,4-dimethyl-3-oxopentanenitrile (10.0 g, 79.9 mmol) in EtOH (200 mL) containing 6 N HCl (6 mL) was refluxed for 17 h, then cooled to room temperature. Solid sodium hydrogen carbonate was added to neutralize the solution. The slurry was filtered. The filtrate was concentrated. Column chromatography (silica gel, 2.5"×5", eluant= EtOAc) afforded the desired 5-amino-3-tert-butyl-1-(2-methylpyridine-5-yl)pyrazole (9.21 g, 62%) as a tan solid.

A magnetically stirred slurry of the above pyrazolamine in anhydrous THF under inert atmosphere is treated dropwise with N,N-diisopropyl-ethyl amine base until all solids have dissolved. The solution is then cooled to −10° C. and phenyl chloroformate is added dropwise over 2 min. The cooling bath is removed and the mixture allowed to reach room temperature and stir 1.5 h. The reaction is quenched with water and extracted 3 times with EtOAc. The combined organic extracts are washed with water and brine, dried ($Na_2SO_4$) and filtered. Removal of solvents in vacuo affords the carbamate. This is immediately used as is for oxidation to the pyridyl N-oxide in a standard way with m-CPBA (or with hydrogen peroxide-urea complex and trifluoroacetic acid according to the method of S. Caron et al., *Tetrahedron Lett.*, 2000, 41(14), 2299–2302) to afford the corresponding pyridine N-oxide.

Urea formation is done by mixing the above carbamate with 4-(2-morpholin-4-yl-ethoxy)naphthalen-1-yl amine and N,N-diisopropyl-ethyl amine in anhydrous DMSO. This mixture is heated at 50° C. for some hours, then cooled to room temperature, quenched with water and extracted with EtOAc as described in Examples above. The title compound is isolated pure after column chromatography using EtOH in CH₂Cl₂.

Example 13

Synthesis of 1-[5-(2-hydroxy-1,1-dimethyl-ethyl)-2-(6-methyl-pyridin-3-yl)-2H-pyrazol-3-yl]-3-[4-(2-pyridin-4yl-ethoxy)-naphthalen-1-yl]-urea

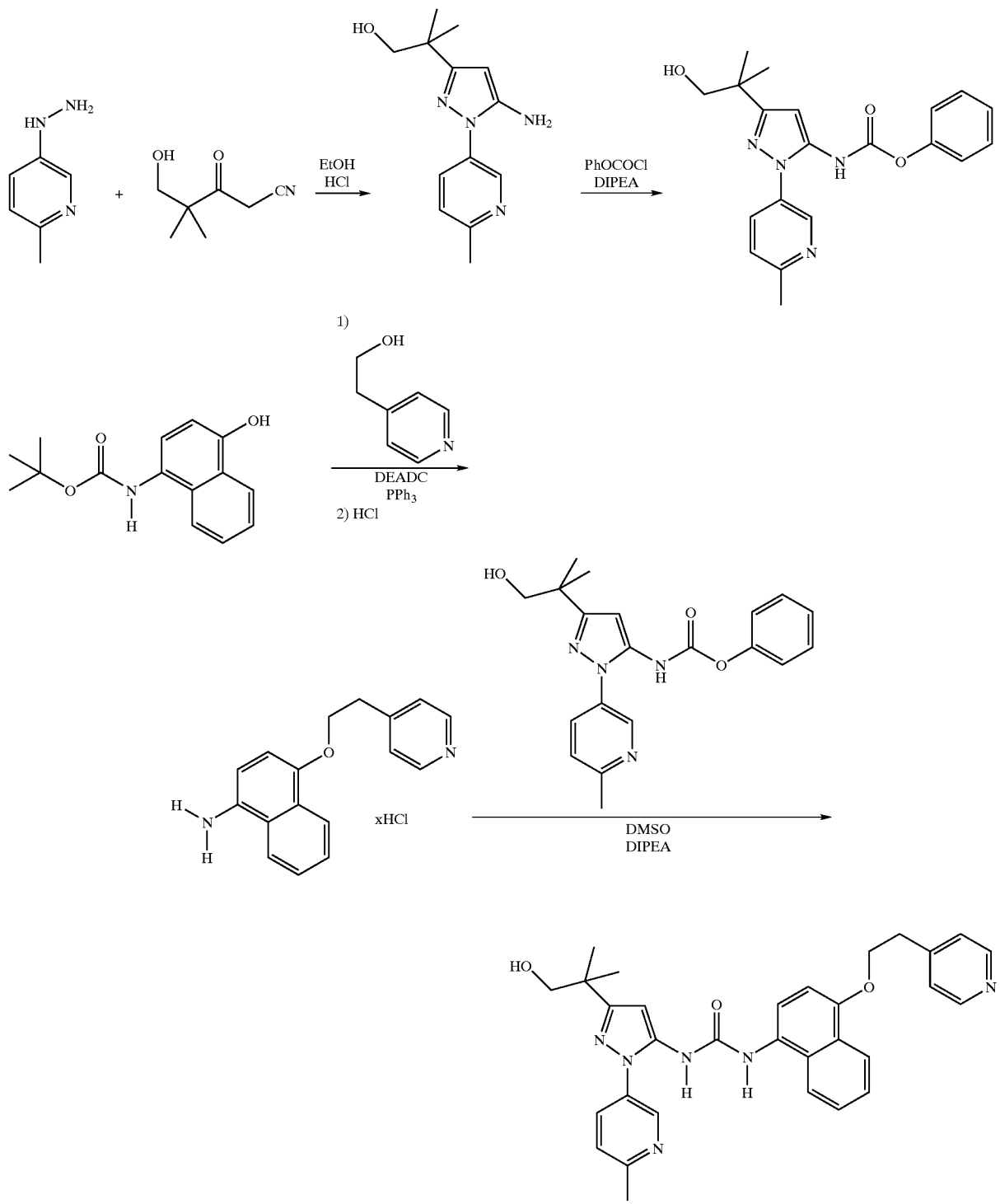

5-Hydrazino-2-methyl-pyridine (see Example 12) is combined with the hydroxy-β-ketonitrile intermediate (see Example 1) in EtOH, in the presence of concentrated HCl. The mixture is refluxed for a few hours, then the volatiles are removed in vacuo, the residue is basified with NaOH and the desired pyrazolamine is isolated by extraction with EtOAc. The product is then purified by column chromatography on silica gel, and reacted with a slight excess of phenyl chloroformate in the presence of N,N-diisopropyl-ethyl amine to afford the desired carbamate.

To a solution of N-Boc-4-amino-naphthalene-1-ol (0.962 g), 2-(pyridin-4-yl)ethanol (1.4 g) and triphenylphosphine (2.90 g) in THF (25 mL) was added dropwise diethyl azodicarboxylate (1.8 mL). The mixture was stirred overnight and the volatiles removed in vacuo. Purification of the residue with flash chromatography using EtOAc as the eluent and concentration in vacuo of the product-rich fractions provided the desired naphthyl ether. To a solution of this product (1.4 g) in dioxane (15 mL) was added HCl (10 mL of a 4M dioxane solution). The solution was stirred overnight and product salt was filtered and dried.

The above salt and the pyrazole carbamate are combined in DMSO in the presence of excess N,N-diisopropyl-ethyl amine and heated to 60° C. for a few hours. The reaction is quenched with water and extractive isolation with EtOAc, followed by purification of the residue by flash chromatography affords the title compound.

Example 14

1-[5-tert-Butyl-2-p-tolyl-2H-pyrazol-3-yl]-3-[4-(pyridin-4-yl-methoxy)naphthalen-1-yl]-urea:

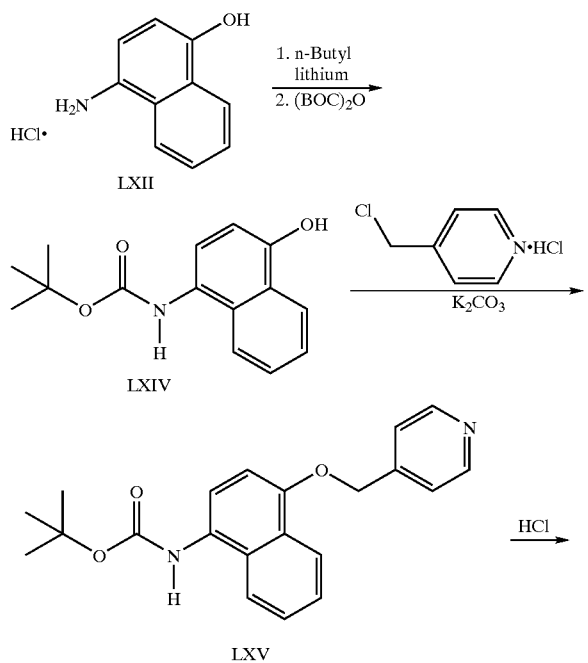

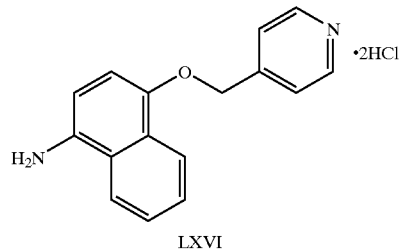

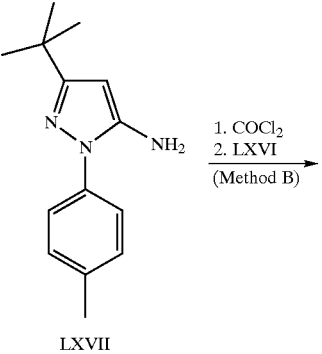

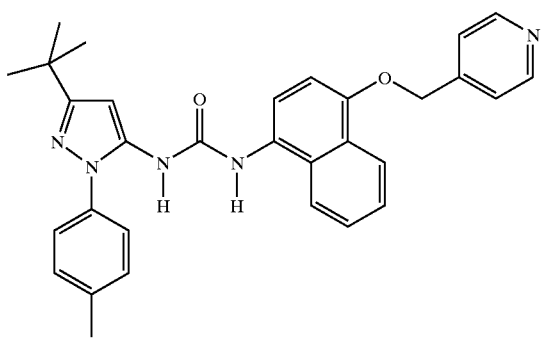

14

A mixture of 4-methylphenyl hydrazine hydrochloride (10.0 g) and 4,4-dimethyl-3-oxopentanenitrile (8.67 g) in 150 mL ethanol and 7 mL concentrated HCl was heated at reflux overnight, cooled to room temperature, basified to pH 12 with alkali and extracted with diethyl ether. The combined organic extracts were washed with brine and dried (MgSO₄). Removal of the volatiles in vacuo left a residue which was triturated with hot petroleum ether (100 mL) and provided 12.5 g of LXVII.

To a mixture of 4-amino-1-naphthol hydrochloride (LXIII) (172.1 g) in 750 mL anhydrous THF at −78° C. was added dropwise over 60 min n-butyl lithium (490 mL of a 1.60 M solution in hexanes). After the addition was complete the mixture was allowed to warm to room temperature and then cooled to −78° C. and di-tert-butyl dicarbonate ((BOC)₂O, 192 g) in 200 mL THF was added over 20 min. The mixture was slowly warmed to room temperature and stirred for 3 h and most of the volatiles removed in vacuo. The residue was diluted with ethyl acetate (1 L) and washed with water (2×200 mL) and brine (200 mL) and filtered through celite and dried (MgSO₄). Removal of the volatiles in vacuo provided LXIV (226.1 g).

A mixture of LXIV (0.397 g), 4-chloromethylpyridine hydrochloride (0.237 g) and potassium carbonate (0.996 g, powdered) in 10 mL of acetonitrile was heated at 80° C. for 6 hr, cooled to room temperature and diluted with water and ethyl acetate. The organic layer was washed with water and brine and dried (MgSO$_4$). Removal of the volatiles in vacuo and purification of the residue with flash chromatography using ethyl acetate as the eluent provided 0.277 g LXV. A mixture of LXV (0.26 g) and HCl (0.6 mL of 4M HCl in dioxane) in 5 mL dioxane was stirred at room temperature for 18 hr. Removal of the volatiles in vacuo provided LXVI.

As outlined in Method B (Scheme I), a mixture of LXVII (0.076 g) and phosgene (0.68 mL of a 1.93 M solution in toluene) in 10 mL methylene chloride and 10 mL saturated sodium bicarbonate was stirred rapidly for 15 min at 0–5° C. and the organic layer dried (MgSO$_4$). Removal of the volatiles in vacuo left a residue which was added to a mixture of the dihydrochloride salt from above (0.104 g) and N,N-di-iso-propylethylamine (0.32 mL) in 5 mL anhydrous THF. The mixture was stirred overnight and diluted with ethyl acetate and water. The organic layer was washed with water and brine and dried (MgSO$_4$). Removal of the volatiles in vacuo and purification of the residue with flash chromatography using ethyl acetate as the eluent and recrystallization of the solid with water and ethanol gave 14, m.p. 132–133° C.

Example 15

1-[5-tert-Butyl-2-p-tolyl-2H-pyrazol-3-yl]-3-[4-(3-(tetrahydropyran-2-yl-oxy)propyn-1-yl)naphthalen-1-yl]-urea:

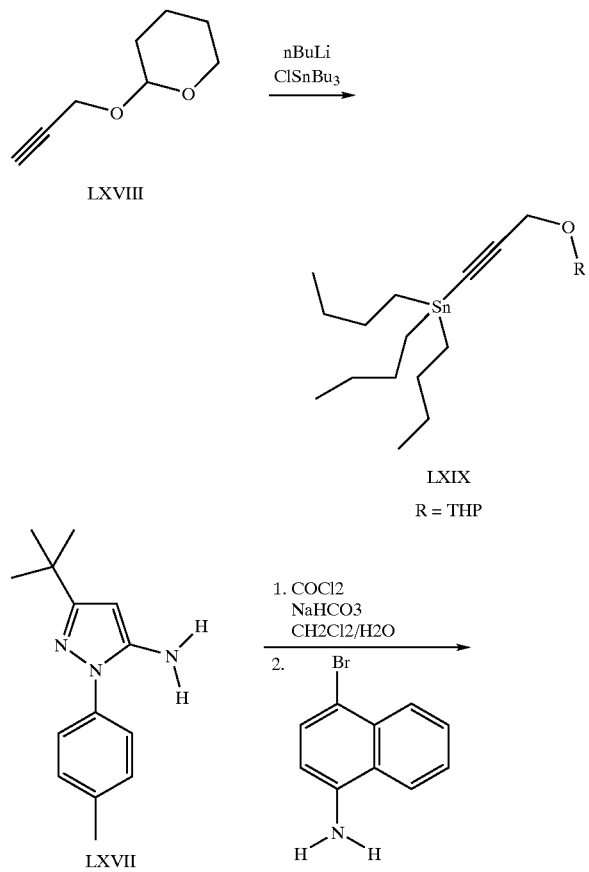

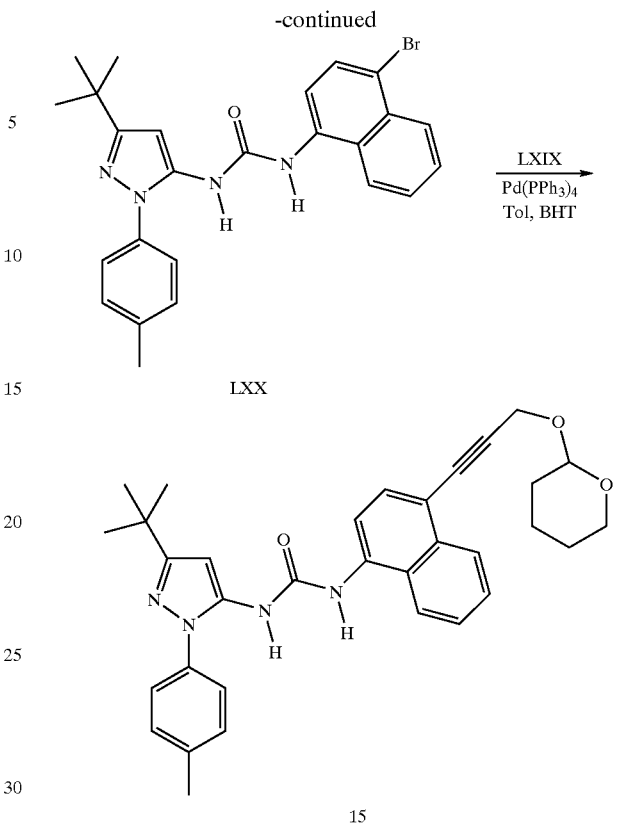

Tetrahydro-2-(2-propynyloxy)-2H-pyran (LXVIII) (2.50 mL; 17.8 mmol) in 100 mL anhydrous THF at −78° C. under inert atmosphere was treated with n-butyllithium (7.1 mL of a 2.5 M solution in hexanes), added via syringe. The reaction was warmed to −20° C. and after 1 h stirring, tributyltin chloride (4.8 mL, 17.8 mmol) was added. After stirring at −20° C. for 1 h the reaction mixture was quenched with dilute NaHCO$_3$ solution (75 mL) and extracted with ethyl ether (3×50 mL). The combined ethereal extracts were washed with brine and dried (MgSO$_4$). After filtration all volatiles were removed in vacuo to produce LXIX as a yellow oil (4.7 g; 11.0 mmol or 62% yield).

A mixture LXVII (Example 1) (1.00 g; 3.76 mmol) and phosgene (5.6 mL of a 2 M solution in toluene) and 4-bromonaphthylamine were reacted according to Method B (Scheme I and Example 14). The product was purified by trituration with hot heptane to afford LXX, mp 193–194° C. (1.75 g, 3.67 mmol, 97% yield).

A mixture of LXX (970 mg, 2.03 mmol) and LXIX (1.31 g, 3.05 mmol) and BHT (50mg) in 50 mL toluene at reflux under inert atmosphere was treated with tetrakis (triphenylphosphine)palladium(0) (350 mg, 0.305 mmol). The reaction mixture slowly changed color to black. After 40 min heating was stopped and, when the reaction mixture had cooled to ambient temperature, a 5 M aqueous solution of KF (~75 mL) was added. The mixture was stirred vigorously for 6 h, then the product was extracted with ethyl acetate (3×50 mL). The combined organic extracts were washed with brine and dried (MgSO$_4$), filtered and all volatiles were removed in vacuo. Column chromatography, using 25% ethyl acetate in hexane eluant, followed by recrystallization from hot ethyl acetate/hexane afforded 780 mg of 15, mp 159–160° C., (1.45 mmol, 72% yield).

Example 16

1-[5-tert-Butyl-2-p-tolyl -2H-pyrazol-3-yl]-3-[4-(3-pyridin-4-propoxy)naphthalen-1-yl]-urea:

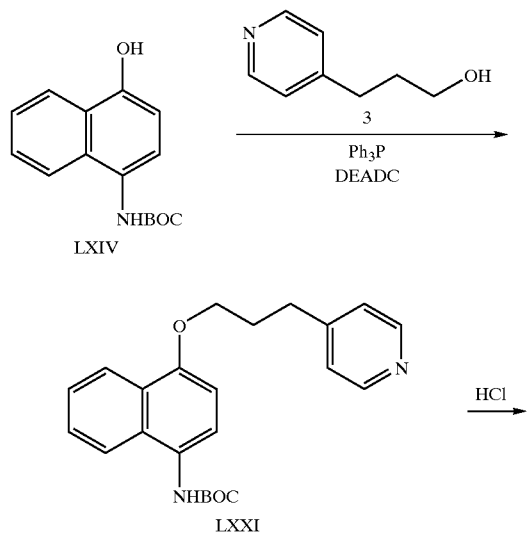

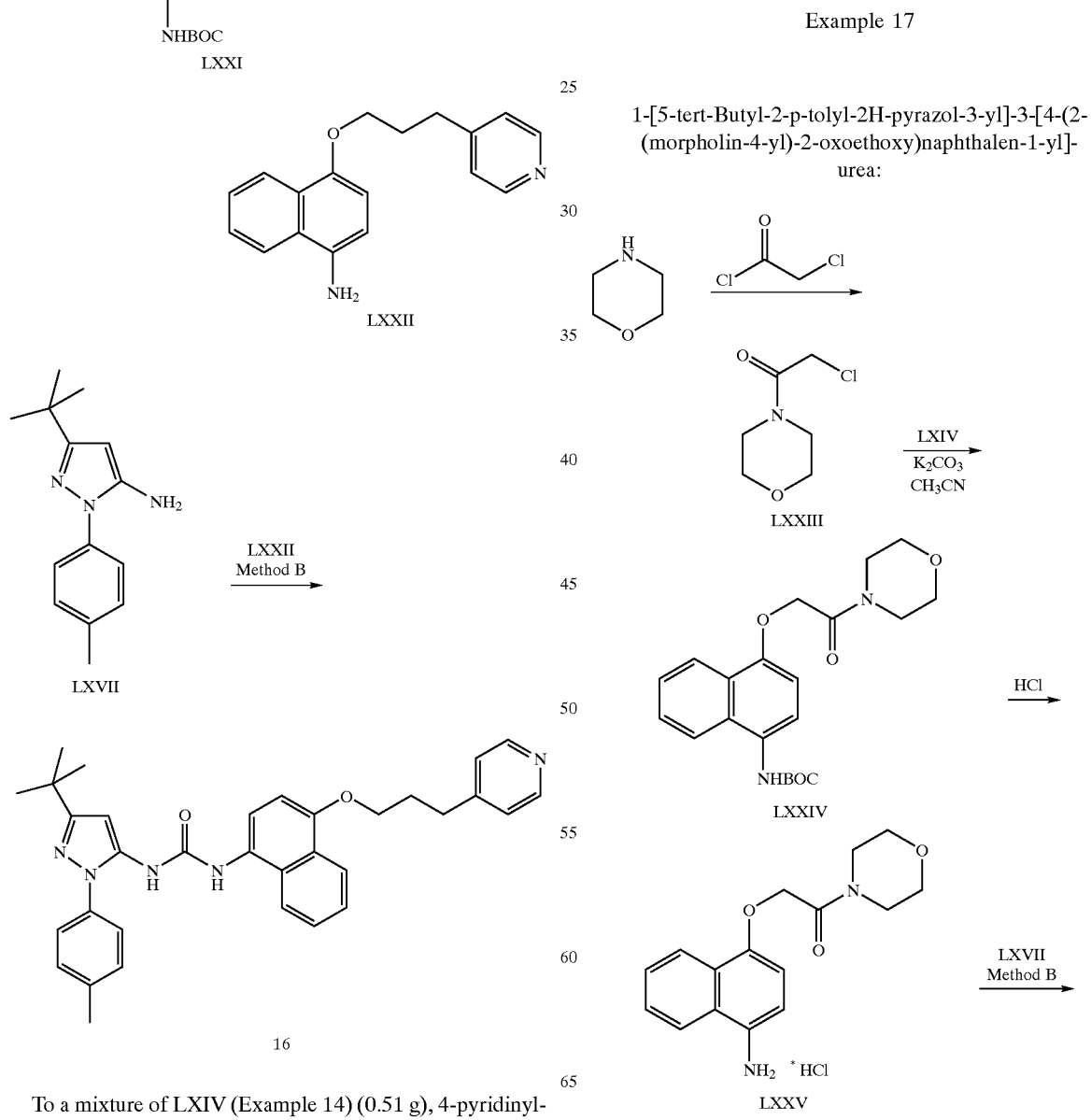

To a mixture of LXIV (Example 14) (0.51 g), 4-pyridinyl-1-propanol (0.76 mL), and triphenylphosphine (1.5 g) in 10 mL anhydrous THF was added dropwise diethyl azodicarboxylate (DEADC, 0.90 mL). After stirring overnight, the volatiles were removed in vacuo. Purification of the residue by flash chromatography using 25% hexanes in ethyl acetate as the eluent and concentration of the product-rich fractions in vacuo provided ether LXXI. A mixture of LXXI (0.74 g) and HCl (5 mL, 4.0 M in dioxane) in 10 mL anhydrous dioxane was stirred overnight. Collection of the precipitate by vacuum filtration provided LXXII. LXXVII (Example 14) (0.23 g), saturated NaHCO₃ (15 mL), dichloromethane (15 mL), phosgene (2.1 mL, 1.93M in toluene) and LXXII (0.32 g) were reacted according to Method B (Scheme I and Example 14). Purification of the residue by flash chromatography using 25% hexanes in ethyl acetate as the eluent, concentration of the product-rich fractions in vacuo, followed by recrystallization from ethyl acetate/methanol provided urea 16, m.p. 205–207° C.

Example 17

1-[5-tert-Butyl-2-p-tolyl-2H-pyrazol-3-yl]-3-[4-(2-(morpholin-4-yl)-2-oxoethoxy)naphthalen-1-yl]-urea:

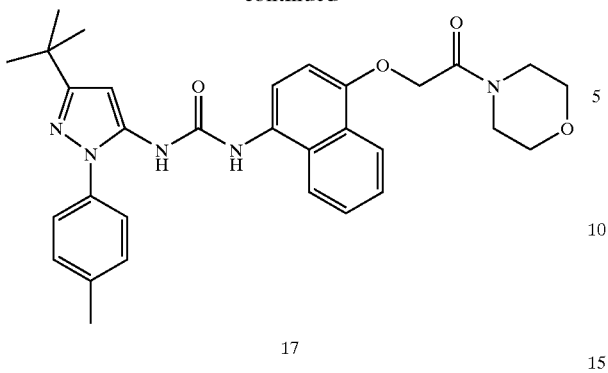

17

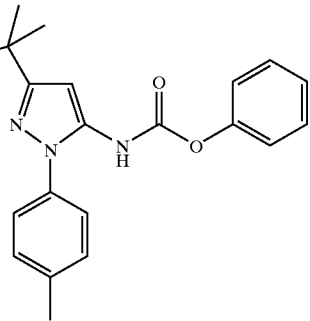

LXXVIII

To a solution of morpholine (0.55 mL) in 5 mL of anhydrous ether at 0° C. was added chloroacetyl chloride. Collection of the precipitate by vacuum filtration provided amide LXXIII. A mixture of LXIV (Example 14) (0.44 g), LXXIII (0.30 g), and powered potassium carbonate (0.70 g) in 10 mL acetonitrile was heated to 80° C. for 3.5 hours, cooled to room temperature, and diluted with ethyl acetate and water. The organic layer was washed with water, saturated $NaHCO_3$, brine, dried ($MgSO_4$) and the volatiles removed in vacuo. Purification of the residue by flash chromatography using 20% ethyl acetate in hexanes as the eluent and concentration of the product-rich fractions in vacuo provided ether LXXIV. A mixture of LXXIV (0.26 g) and HCl (0.7 mL, 4.0 M in dioxane) in 4 mL anhydrous dioxane was stirred overnight. Collection of the precipitate by vacuum filtration provided LXXV. LXVII (Example 14), (0.13 g), and LXXV were reacted according to Method B (Scheme I and Example 14). Trituration of the residue in hot methanol/water followed by collection of the solid by vacuum filtration provided urea 17, m.p. 240–241° C.

Example 18

1-[5-tert-Butyl-2-p-tolyl-2H-pyrazol-3-yl]-3-[4-(2-(1-oxothiomorpholin-4-yl)ethoxy)naphthalen-1-yl]-urea:

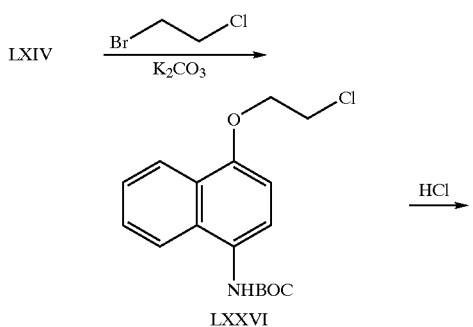

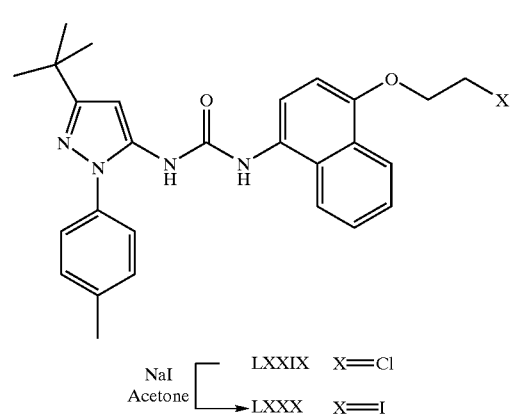

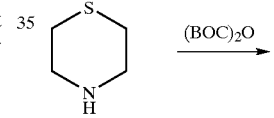

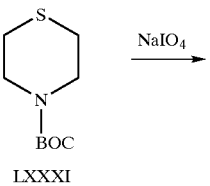

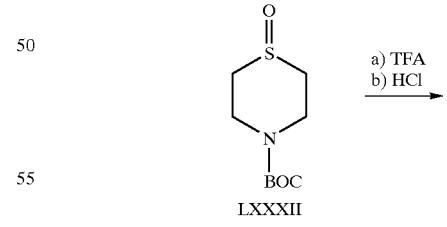

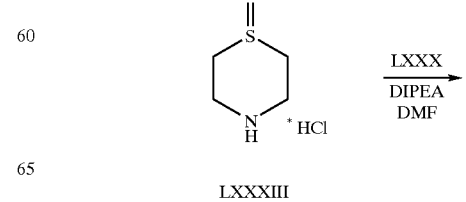

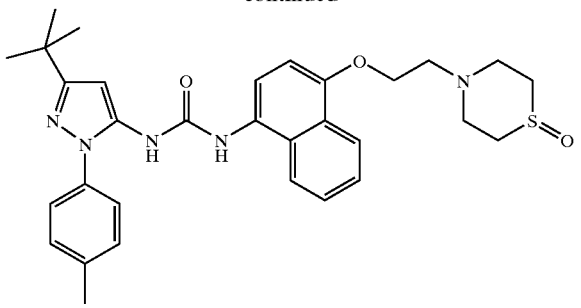

18

A suspension of LXIV (Example 1) (5.0 g), powdered potassium carbonate (13.3 g) and 1-bromo-2-chloroethane (5.5 g) in 100 mL acetonitrile was heated at 80° C. overnight, cooled to room temperature and partitioned between ethyl acetate and water. The organic layer was washed with brine, dried (MgSO₄) and the volatiles removed in vacuo. Purification of the residue by flash chromatography using 25% ethyl acetate in hexanes as the eluent and concentration of the product-rich fractions in vacuo provided ether LXXVI. A mixture of LXVI (2.0 g) and HCl (15 mL, 4.0 M in dioxane) in 10 mL anhydrous dioxane was stirred overnight. Ether was added and the precipitate collected by vacuum filtration to afford LXXVII. As outlined in Method C, (Scheme I) a solution of LXXVII (1.6 g), phenyl carbamate LXXVIII, prepared from LXVII, phenyl chloroformate (1.05 equiv), pyridine (3 equiv.) in THF, (2.3 g) and diisopropylethylamine (3.1 g) in 10 mL anhydrous DMSO was stirred for one hour and diluted with ethyl acetate and water. The organic layer was washed with water, 50% NaHCO₃, brine, dried (MgSO₄), and the volatiles removed in vacuo. Purification of the residue by flash chromatography using 33% ethyl acetate in hexanes as the eluent, concentration of the product-rich fractions in vacuo, followed by trituration with 33% ethyl acetate in hexanes provided LXXIX. A mixture of LXXIX (1.6 g) and sodium iodide (5.0 g) in 10 mL acetone was heated at reflux for 4 days, cooled to room temperature and diluted with dichloromethane. The organics were washed with water, dried (Na₂SO₄) and the volatiles removed in vacuo to provide LXXX.

To a solution of thiomorpholine (0.50 g) in 25 mL of dichloromethane was added di-tert-butyldicarbonate. The mixture was stirred for 18 h at room temperature and the volatiles removed in vacuo. Recrystallization of the residue from hexanes provided LXXXI. To a solution of LXXXI (0.40 g) in 8 mL ethanol at 0° C. was added sodium periodate. The mixture was stirred at 0° C. one hour, warmed to room temperature and stirred five days. The mixture was diluted with water and extracted with dichloromethane. The organic layer was washed with brine, dried (Na₂SO₄) and the volatiles removed in vacuo. Trituration of the residue with hexanes provided sulfoxide LXXXIII. To a solution of LXXXIII (0.15 g) in 5 mL dichloromethane was added trifluoroacetic acid (TFA, 0.52 mL). The mixture was stirred 5 h and the volatiles removed in vacuo. The residue was dissolved in methanol and HCl (4.0 M in dioxane) was added. The volatiles were removed in vacuo to provide sulfoxide LXXXIII. A mixture of LXXXIII (0.05 g), LXXX (0.19 g), DIPEA (0.06 mL) in 2.5 mL DMF was stirred overnight. The mixture was partitioned between ethyl acetate and water and the aqueous layer extracted with ethyl acetate. The combined organic layers were washed with brine, dried (MgSO₄) and the volatiles removed in vacuo. Purification of the residue by flash chromatography using 9% methanol in ethyl acetate as the eluent and concentration of the product-rich fractions in vacuo provided urea 18, m.p. 205–207° C.

Example 19

1-[5-tert-Butyl-2-p-tolyl-2H-pyrazol-3-yl]-3-[4-(2-pyridin-4-yl-ethenyl)naphthalen-1-1 -yl]-urea:

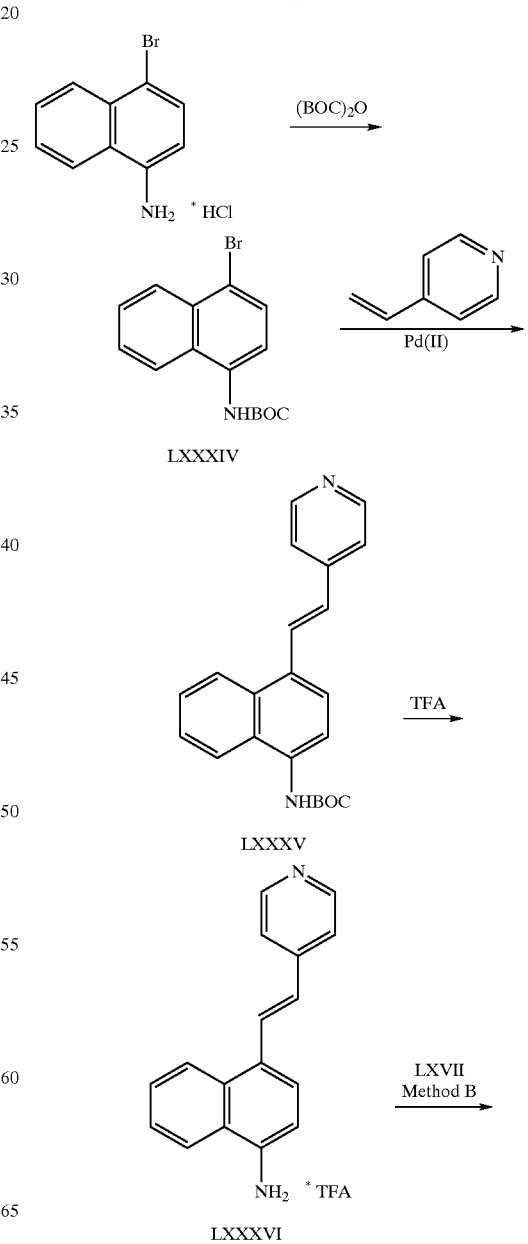

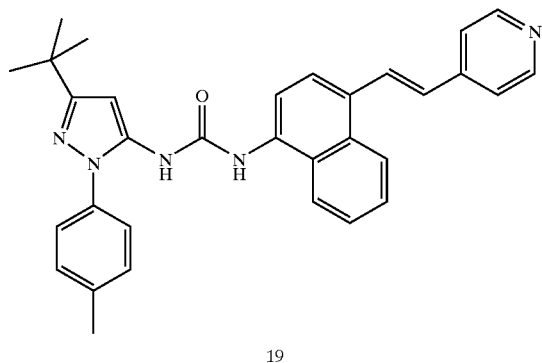

19

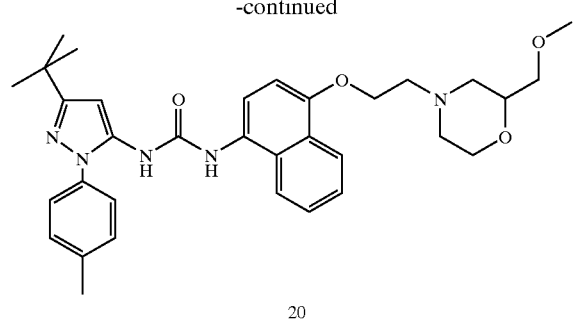

20

A mixture of 4-bromoaminonaphthalene (5.0 g) and di-tert-butyldicarbonate (5.9 g) in 100 mL toluene was heated at 70° C. for 15 hours, cooled to room temperature and the volatiles removed in vacuo. The residue was dissolved in ethyl acetate, washed with 0.1M HCl and brine, dried (MgSO$_4$) and the volatiles removed in vacuo. Recrystallization of the residue from hot petroleum ether provided LXXXIV. 4-Vinylpyridine (0.86 mL) was added to a suspension of LXXXIV (2.0 g) in 5 mL of triethylamine, followed by palladium (II) acetate (0.014 g) and tri-ortho-tolylphosphine (0.038 g). The mixture was heated at 110° C. for four hours, cooled to room temperature, diluted with water and ethyl acetate. The organic layer was washed with brine, dried (MgSO$_4$) and the volatiles removed in vacuo. Purification of the residue by flash chromatography using 50% ethyl acetate in hexanes as the eluent and concentration of the product-rich fractions in vacuo provided naphthalene LXXXV. A solution of LXXXV (0.34 g) in 10 mL TFA was stirred one hour and the volatiles removed in vacuo to provided LXXXVI. LXXXVI and LXVII (Example 14) were reacted according to Method B to provide 19, m.p. 203° C. (dec).

A mixture of LXXXVII (prepared by the method of Y. Jinbo et al; *J. Med. Chem.*, 1994, 37, 2791) (0.044 g), LXXX (see Example 5) (0.15 g) and DIPEA (0.068 g) was stirred overnight, diluted with ether and water. The organic layer was washed with brine, dried (MgSO$_4$) and the volatiles removed in vacuo. Purification of the residue by flash chromatography using a gradient of 1–4% methanol in ethyl acetate as the eluent and concentration of the product-rich fractions in vacuo provided 20, m.p. 85–90° C.

Example 21

1-[5-tert-Butyl-2-p-tolyl-2H-pyrazol-3-yl]-3-[4-(2-morpholin-4-yl-ethoxy)naphthalen1-yl]-urea:

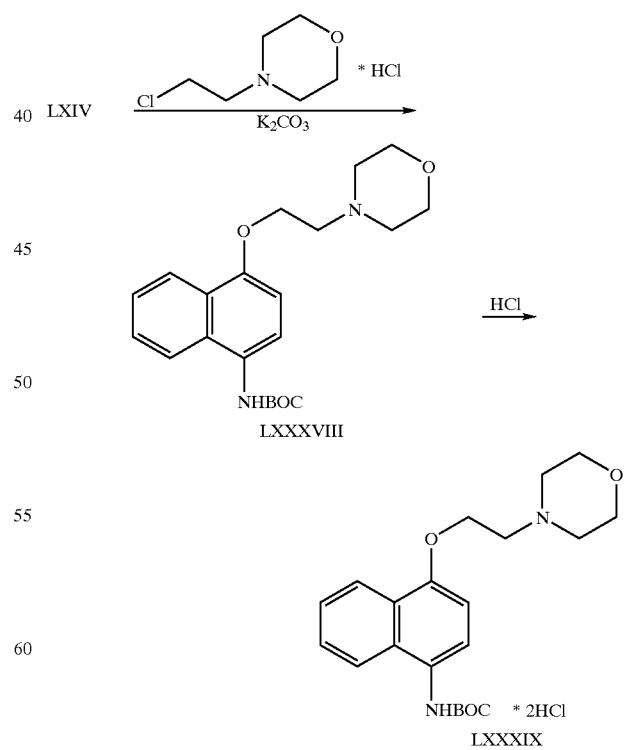

Example 20

1-[5-tert-Butyl-2-p-tolyl-2H-pyrazol-3-yl]-3-[4-(2-(2-(methoxymethyl)morpholin-4-yl)ethoxy) naphthalen-1-yl]-urea:

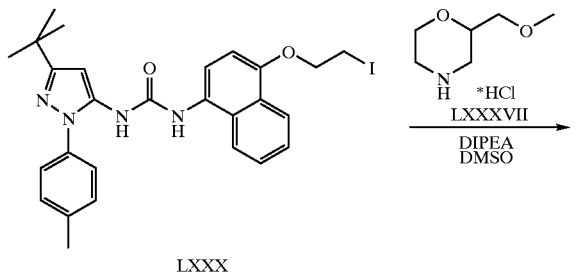

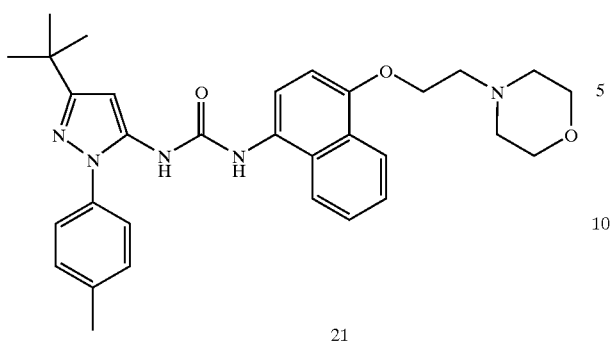

21

A mixture of LXIV (Example 14) (0.464 g), 4-(2-chloroethyl)morpholine hydrochloride (0.3435 g) and powdered potassium carbonate (0.93 g) was heated in acetonitrile (15 mL) at 80° C. for 3 hours, cooled to room temperature and diluted with ethyl acetate and water. The organic layer was washed with water, brine, dried (MgSO$_4$) and the volatile removed in vacuo. Purification of the residue by flash chromatography using 12% hexanes in ethyl acetate as the eluent and concentration in vacuo of the product-rich fractions afforded LXXXVIII. A solution of LXXXVIII (0.511 g) and HCl (1 mL of a 4M dioxane solution) in 5 mL dioxane was stirred at room temperature 20 hours. Removal of the volatiles in vacuo provided the product LXXXIX, which was reacted with LXVII (Example 14) according to Method B to provide 21, m.p. 142–143° C.

Example 22

1-[5-tert-Butyl-2-(2-methylpyridin-5-yl)-2H-pyrazol-3-yl]-3-[4-(2-morpholin-4-yl-ethoxy)naphthalen-1-yl]-urea:

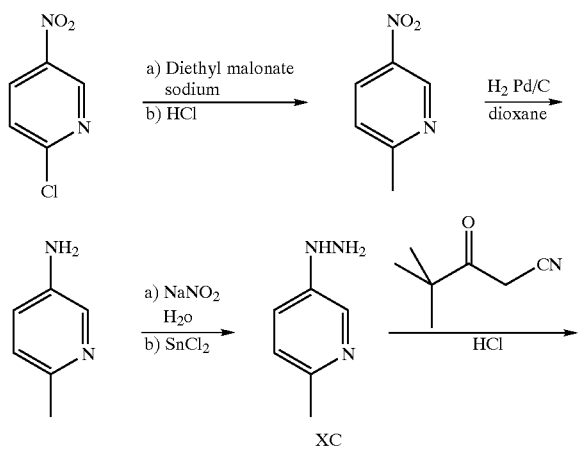

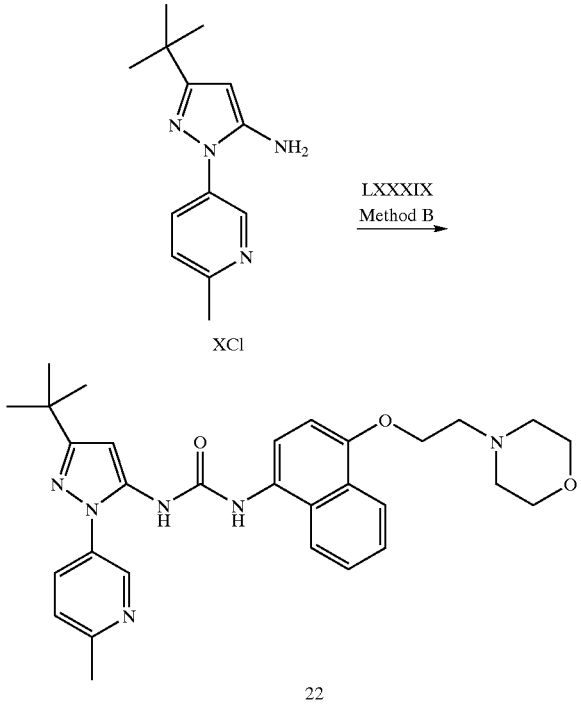

22

A slurry of diethyl malonate (42 mL) and sodium (4.71 g) was warmed slowly to 90° C. and stirred at 90° C. for 2 hours and 120° C. for 30 min. before being cooled to room temperature. Toluene (200 mL) and 2-chloro-5-nitropyridine (25.0 g) were added and the mixture was heated at 110° C. for 1.5 hours and ambient temperature for 17 h. After removal of the volatiles in vacuo, 6 N HCl (200 mL) was added and the mixture heated to reflux for 4 h and cooled to room temperature. The solution was neutralized with solid sodium carbonate, extracted with ethyl acetate (6×100 mL), dried over solid magnesium sulfate, and concentrated to a dark solid. This material was purified by flash chromatography using 20% ethyl acetate in petroleum ether as the eluent. Concentration in vacuo of the product-rich fractions afforded 2-methyl-5-nitropyridine. A mixture of 2-methyl-5-nitropyridine (13.0 g) and 10% Pd on activated carbon (0.1 g) in 1,4-dioxane (150 mL) was hydrogenated at 50 psi for 24 hours and filtered over celite. Removal of the volatiles in vacuo provided 2-methyl-5-aminopyridine. A solution of this compound (9.90 g) was dissolved in 6 N HCl (100 mL), cooled to 0° C., and vigorously stirred throughout the procedure. Sodium nitrite (6.32 g) in water (50 mL) was added. After 30 min, tin (II) chloride dihydrate (52.0 g) in 6 N HCl (100 mL) was added and the reaction slurry was stirred at 0° C. for 3 hours. The pH was adjusted to pH 14 with 40% aqueous potassium hydroxide solution and extracted with ethyl acetate. The combined organic extracts were dried (MgSO$_4$) and removal of the volatiles in vacuo provided hydrazine XC. A solution of XC (8.0 g) and 4,4-dimethyl-3-oxopentanenitrile (10.0 g) in ethanol (200 mL) and 6 N HCl (6 mL) was refluxed for 17 hours and cooled to room temperature. Solid sodium hydrogen carbonate was added to neutralize the solution. The slurry was filtered and removal of the volatiles in vacuo provided a residue which was purified by column chromatography using ethyl acetate as the eluent. Concentration in vacuo of the product-rich fractions afforded XCI, which was reacted with LXXXIX (Example 21) according to Method B to provide 22, m.p. 121–123° C.

Example 23

1-[5-tert-Butyl-2-(2-methylpyridin-5-yl)-2H-pyrazol-3-yl]-3-[4-(2-pyridin-4-yl-ethoxy)naphthalen-1-yl]-urea

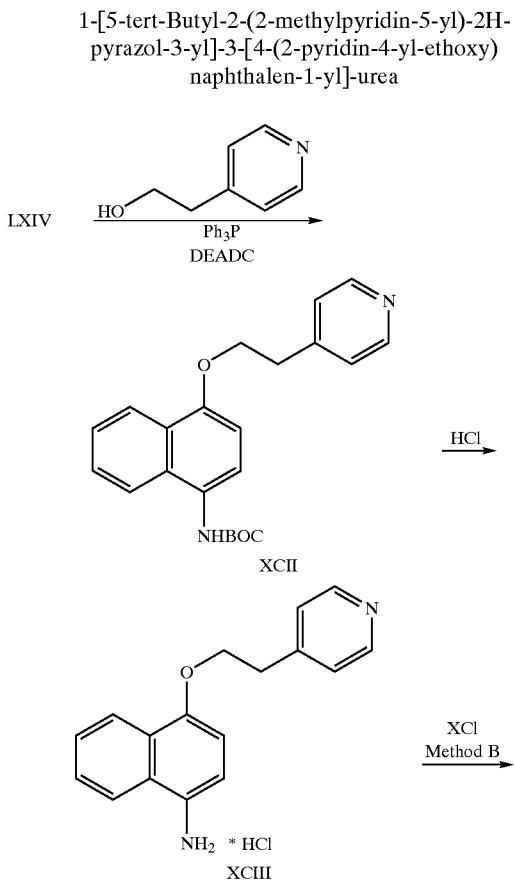

To a solution of LXIV (Example 14) (0.962 g), 2-(pyridin-4-yl)ethanol (1.4 g) and triphenylphosphine (2.90 g) in THF (25 mL) was added dropwise DEADC (1.8 mL). The mixture was stirred overnight and the volatiles removed in vacuo. Purification of the residue with flash chromatography using ethyl acetate as the eluent and concentration in vacuo of the product-rich fractions provided XCII. To a solution of XCII (1.4 g) in dioxane (15 mL) was added HCl (10 mL of a 4M dioxane solution). The solution was stirred overnight and product XCIII was filtered and dried. This was reacted with XCI (Example 22) according to Method B to provide 23, m.p. 189–190° C.

Example 24

1-[5-(1-Methylcyclohex-1-yl)-2-phenyl-2H-pyrazol-3-yl]-3-[4-(2-morpholin-4-yl-ethoxy)naphthalen-yl]-urea

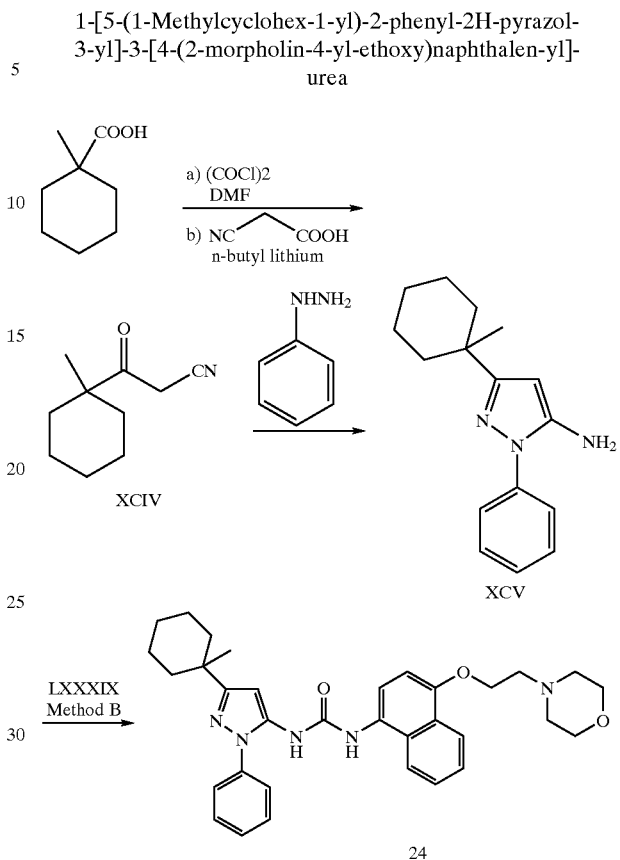

To a solution of cyclohexane-1-methyl-1-carboxylic acid (1.31 g) in 5 mL methylene chloride was added oxalyl chloride solution (5.5 mL of a 2.0 M methylene chloride solution) and 1 drop of anhydrous DMF. The mixture was refluxed for 3 hours under inert atmosphere and cooled to room temperature. Cyanoacetic acid (1.57 g) in ethyl acetate was dried ($MgSO_4$) and the volatiles removed in vacuo. The residue and 2,2-bipyridine (~10 mg) in anhydrous THF (70 mL) was cooled to −70° C. and treated with n-BuLi (2.5 M in Hexanes) slowly, while allowing the reaction mixture to reach 0° C. When the red color persists at 0° C. (ie. after 15.0 mL of n-BuLi solution), the solution was recooled to −70° C. and the acid chloride solution from above (9.21 mmol) was added via syringe in one portion. The mixture was warmed to room temperature, stirred 0.5 hours, poured onto 1 N aq. HCl (200 mL) and extracted with chloroform (3×100 mL). The combined organic layers were washed with saturated aqueous $NaHCO_3$, brine and dried ($MgSO_4$). Removal of volatiles in vacuo provided a residue which was purified by column chromatography using hexanes and ethyl acetate as the eluent. Concentration in vacuo of the product-rich fractions provided XCIV. A solution of XCIV (0.80 g) and phenylhydrazine (0.48 mL) in toluene (5 mL) was heated with azeotropic removal of water overnight and the volatiles removed in vacuo. Purification of the residue with flash chromatography using ethyl acetate and hexanes as the eluent and concentration in vacuo of the product-rich fractions provided XCV, which was reacted with LXXXIX (Example 21) according to Method B to provide 24, m.p. 147–149° C.

Example 25

1-[5-tert-Butyl-2-p-tolyl-2H-pyrazol-3-yl]-3-[4-(pyridin-4-yl-methylamino)nalhthalen-1-yl]-urea:

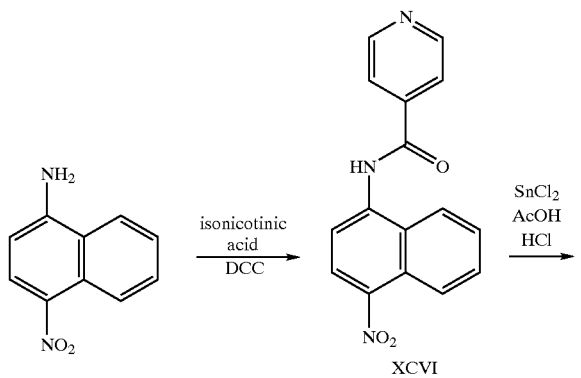

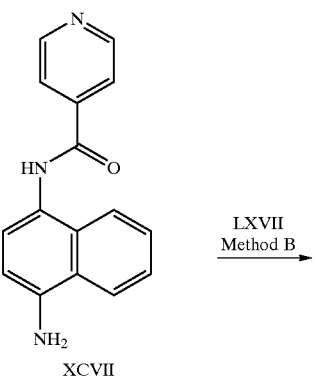

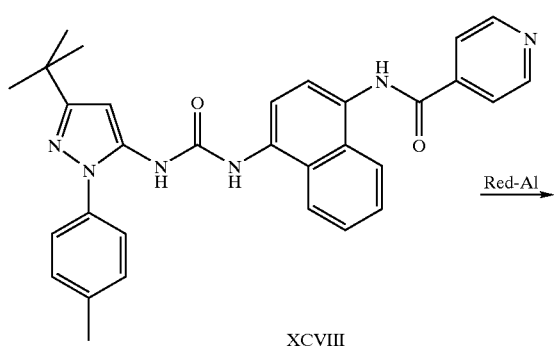

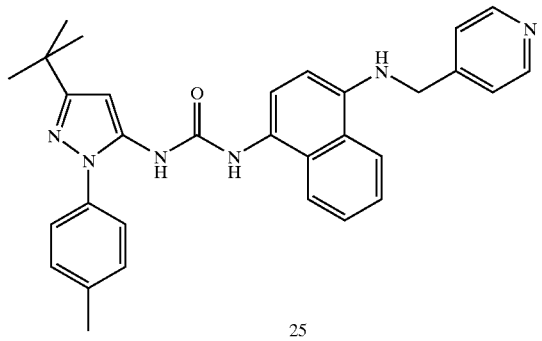

Isonicotinic acid (1.13 g) and DCC (2.5 g) were mixed together in methylene chloride (80 mL) under an inert atmosphere and at room temperature. After 30 min 4-nitro-1-naphthylamine (1.70 g) was added to this suspension as well as a catalytic amount of DMAP (~50 mg). After 2 days the suspension was filtered through Celite, the volatiles removed in vacuo and the residue purified by column chromatography to afford XCVI. A mixture of XCVI (0.299 g) in acetic acid (6 mL) was treated at room temperature with a solution of tin chloride (1.55 g) in 6 mL of concentrated HCl. After stirring for 1.5 hours, the mixture was poured slowly into 200 mL 15% aqueous NaOH solution and extracted with ethyl acetate (3×100 mL). Drying (MgSO$_4$), removal of volatiles in vacuo and purification of the residue by column chromatography using 5% methanol in ethyl acetate as the eluent afforded XCVII, which was reacted with LXVII (Example 14) according to Method B to provide XCVIII. To a suspension of XCVIII (0.101 g) in anhydrous THF (7 ML) at room temperature was added dropwise Red-Al (65% w/w solution in toluene; 0.27 mL) under an inert atmosphere. The mixture was then refluxed for 1 h (dark red color), cooled and methanol was added dropwise until no more evolution of H$_2$ was detected. Removal of most of the solvent in vacuo provided a residue which was purified by column chromatography using hexanes, 50% ethyl ecetate in hexanes and finally ethyl acetate as the eluents. Concentration of the product-rich fractions in vacuo furnished solid 25, m.p. 174–177° C.

Example 26

1-[5-tert-Butyl-2-(3-(2-morpholin-4-yl-ethyl)phenyl)-2H-:pyrazol-3-yl]-3-[4-(2-morpholin-4-yl-ethoxy)naphthalen-1-yl]-urea:

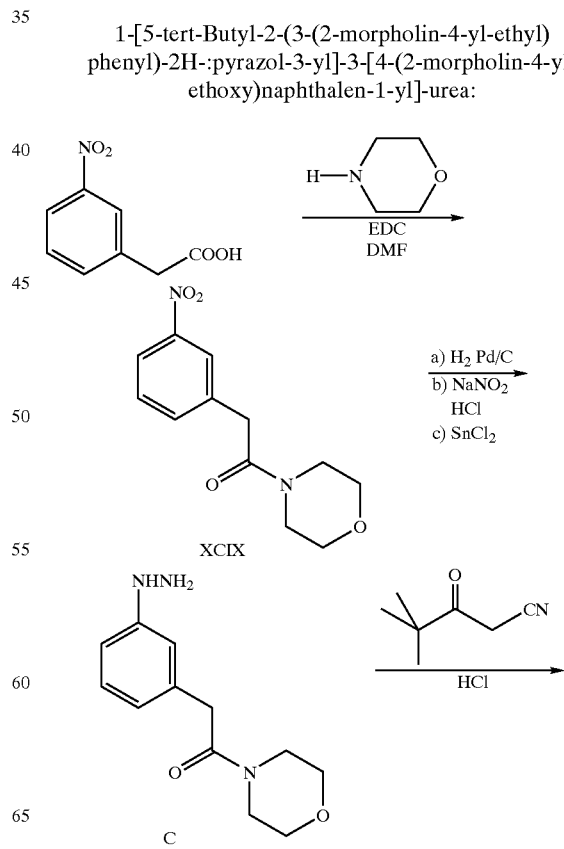

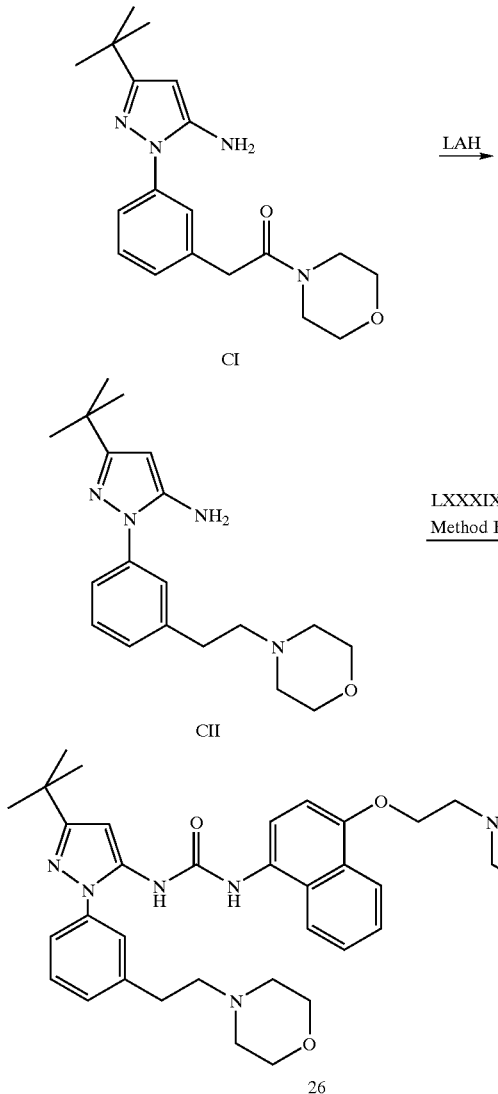

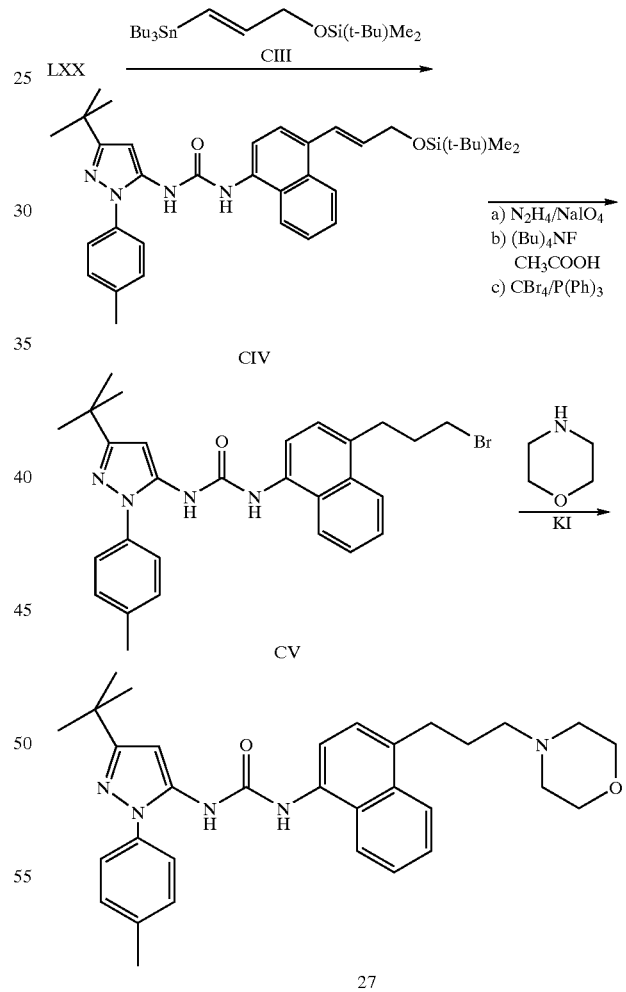

A mixture of 3-nitrophenylacetic acid (5.02g), morpholine (4.83 mL) and EDC (10.62 g) in 80 mL DMF at room temperature was stirred for 6 hours and diluted with water and extracted with ethyl acetate. The combined organic extracts were washed with water and brine and dried (MgSO$_4$). Removal of the volatiles in vacuo provided XCIX. A mixture of XCIX (6.7 g) and 10% Pd on carbon (0.1 g) in ethyl acetate (100 mL) was hydrogenated at 45 psi for 15 hours and filtered over celite. Removal of the volatiles in vacuo furnished an amine (5.7 g) which was dissolved in 6 N HCl (40 mL), cooled to 0° C., and vigorously stirred. Sodium nitrite (2.11 g) in water (5 mL) was added in a dropwise fashion. After 30 min, tin (II) chloride dihydrate (52.0 g) in 6 N HCl (100 mL) was added via addition funnel and the reaction slurry was stirred at 0° C. for 3 hours. The pH was adjusted to 14 with 40% aqueous sodium hydroxide solution and the solution extracted with ethyl acetate. The organic layers were dried (MgSO$_4$). Removal of the volatiles in vacuo provided C. A solution of C (2 g) and 4,4-dimethyl-3-oxopentanenitrile (1.1 g) in ethanol (80 mL) containing 6 N HCl (2 mL) was refluxed for 17 hours, cooled to room temperature and the pH was adjusted to 14 with 40% aqueous sodium hydroxide solution. The mixture was extracted with ethyl acetate and the combined organic extracts were dried (MgSO$_4$). Removal of the volatile in vacuo provided CI. To a solution of CI (150 mg) in dry THF (10 mL) at 0° C. was added dropwise a solution of LAH in ether (2.13 mL of a 1M solution). The mixture was slowly warmed to 60° C., stirred for 5 hours, cooled to room temperature and stirred 16 hours. The reaction was quenched with the addition of 10% aqueous NaOH solution until a neutral pH was achieved The mixture was extracted with ethyl acetate and the combined organic extracts were dried (MgSO$_4$). Removal of the volatile in vacuo provided a residue which was purified by column chromatography using ethyl acetate as the eluent. Concentration of the product-rich fractions in vacuo furnished CII, which was reacted with LXXXIX (Example 21) according to Method B to provide 26, as an oil.

Example 27

1-[5-tert-Butyl-2-p-tolyl-2H-pyrazol-3-yl]-3-[4-(3-morpholin-4-yl-propyl)naphthalen-1-yl]-urea:

A mixture of LXX (Example 15) (3.0 g), CIII (prepared by the procedure of J. W. Labadie et al; 1983, J. Org. Chem. 48, 4634) (3.0 g) and tetrakistriphenylphosphinepalladium (0.15 g) in 18 mL toluene was heated to 100° C. for 30 min. Another 0.050 g of catalyst was added. The mixture was heated three hours, cooled to room temperature, diluted with ether and washed with 5% NH$_4$OH, water, brine, dried (MgSO$_4$) and the volatiles removed in vacuo. Purification of the residue by flash chromatography using 1% methanol in dichloromethane as the eluent and concentration of the product-rich fractions in vacuo provided CIV. To CIV (2.2 g), and hydrazine (4.9 g) in 50 mL ethanol and 10 mL THF at 0° C. was added dropwise a solution of sodium periodate (8.1 g) in 15 mL water. The mixture was warmed to room temperature, stirred six hours, heated to 40° C. for two hours and diluted with dichloromethane, washed with IN sodium hydroxide, water, brine and dried (MgSO$_4$). Removal of the volatiles in vacuo provided the saturated olefin. A mixture of this alkane (2.1 g) and tetrabutylammonium flouride (14.4 mL, 1M in THF) and acetic acid (1.1 g) was stirred overnight, diluted with ethyl acetate and washed with water, brine, and dried (MgSO$_4$). Removal of the volatiles in vacuo, purification of the residue by flash chromatography using 33% hexanes in ethyl acetate as the eluent and concentration of the product-rich fractions in vacuo provided the alcohol. To a solution of this alcohol (0.60 g) in acetonitrile at 0° C. was added triphenylphosphine (0.52 g) then carbon tetrabromide (0.65 g). The mixture was stirred at room temperature for two days and the volatiles removed in vacuo. Purification of the residue by flash chromatography using 33% ethyl acetate in hexanes as the eluent and concentration of the product-rich fractions in vacuo provided CV. A mixture of CV (0.23 g), morpholine (0.039 g), KI (0.073 g) and DIPEA (0.1 mL) in DMF (3 mL) was stirred 6 hours at room temperature and diluted with ether and water. The organic layer was washed with brine and dried (MgSO$_4$). Removal of the volatiles in vacuo provided a residue which was purified by flash chromatography using ethyl acetate as the eluent. Concentration in vacuo of the product-rich fractions provided 14 which was recrystallized from hexanes and ethyl acetate, m.p. 147–149° C.

Table 1 illustrates additional compounds of the invention, which were prepared by methods analogous to those described above.

TABLE 1

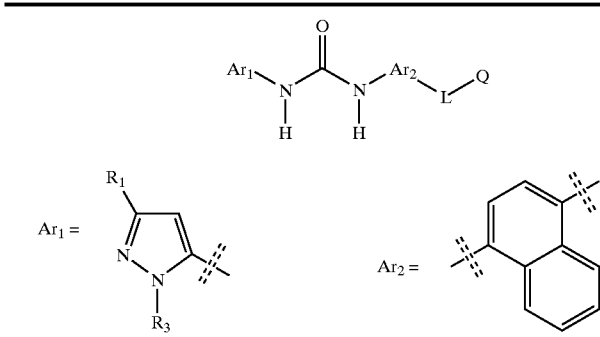

| Ex. No. | R$_1$ | R$_3$ | Q—L— | m.p.° C. |
|---|---|---|---|---|
| 28 | tert-butyl | 2-Cl-pyridin-5-yl | 2-(morpholin-4-yl)ethoxy | 123–125 |
| 29 | tert-butyl | 4-methyl-phenyl | 2-(imidazol-1-yl)ethoxy | 201–202 |
| 30 | tert-butyl | 2-methoxy-pyridin-5-yl | 2-(morpholin-4-yl)ethoxy | 108–110 |
| 31 | tert-butyl | pyridin-3-yl | 2-(morpholin-4-yl)ethoxy | 191–192 |
| 32 | tert-butyl | 4-Cl-phenyl | 2-(morpholin-4-yl)ethoxy | 116–118 |
| 33 | tert-butyl | 4-methyl-phenyl | pyridin-3-ylmethylamino | 137–140 |
| 34 | tert-butyl | 4-methyl-phenyl | morpholin-4-yl-methyl | 174 |
| 35 | tert-butyl | 4-methyl-phenyl | 2-(pyridin-4-yl)ethoxy | 187–190 |
| 36 | tert-butyl | 4-methyl-phenyl | 3-(pyridin-3-yl)-n-propoxy | 162–163 |
| 37 | tert-butyl | 4-methyl-phenyl | morpholine-4-carbonyloxyethoxy | 176–177 |
| 38 | tert-butyl | 4-methyl-phenyl | 2-(morpholin-4-yl)ethoxy (Ar$_2$ = 3-methylnapth-1-yl) | 176–177 |
| 39 | tert-butyl | 4-methyl-phenyl | 2-(pyridin-4-yl)ethyl | 117–120 |
| 40 | tert-butyl | methyl | 2-(morpholin-4-yl)ethoxy | 201–202 |
| 41 | tert-butyl | 4-methyl-phenyl | 2-(thiomorpholin-4-yl)ethoxy | 122–124 |
| 42 | tert-butyl | 4-methyl-phenyl | 2-(piperazin-1-yl)ethoxy | 190 |
| 43 | tert-butyl | 4-methyl-phenyl | 2-(morpholin-4-yl)-n-propoxy | 110–111 |
| 44 | tert-butyl | 4-methyl-phenyl | 2-(4-tetrahydropyran-4-yl)ethoxy | 174–175 |
| 45 | tert-butyl | 4-methyl-phenyl | 3-(morpholin-4-yl)propyn-1-yl | 120–121 |
| 46 | tert-butyl | 4-methyl-phenyl | 3-(piperidin-1-yl)propyn-1-yl | 109–112 |
| 47 | tert-butyl | 4-methyl-phenyl | 4-[4-(tetrahydropyran-2-yloxy)but-1-ynyl] | 180–181 |
| 48 | tert-butyl | 4-methyl-phenyl | 2-(3,4-dimethoxyphenyl)ethoxy | 183–184 |
| 49 | tert-butyl | 4-methyl-phenyl | (pyridine-4-carbonyl)amino | >250 |
| 50 | i-Pr | phenyl | 2-(morpholin-4-yl)ethyl | 177–178 |
| 51 | CF$_3$CH$_2$ | 4-methyl-phenyl | 2-(morpholin-4-yl)ethyl | 176–178 |
| 52 | 3-tetrahydro-pyranyl | phenyl | 2-(morpholin-4-yl)ethyl | 155–156 |
| 53 | cyclohexyl | phenyl | 2-(morpholin-4-yl)ethyl | 191–192 |
| 54 | tert-butyl | n-butyl | 2-(morpholin-4-yl)ethyl | 81–83 |
| 55 | tert-butyl | benzyl | 2-(morpholin-4-yl)ethyl | 180–181 |
| 56 | tert-butyl | 4-methyl-3-morpholin-4-yl-methylphenyl | 2-(morpholin-4-yl)ethyl | oil |

TABLE 1-continued

| Ex. No. | $R_1$ | $R_3$ | Q—L— | m.p.° C. |
|---|---|---|---|---|
| 57 | tert-butyl | 4-methyl-3-C(O)NH$_2$-phenyl | 2-(morpholin-4-yl)ethyl | oil |
| 58 | tert-butyl | 4-methyl-3-(dimethyl)NCH$_2$-phenyl | 2-(morpholin-4-yl)ethyl | oil |
| 59 | tert-butyl | 4-methyl-phenyl | pyridin-4-yl-oxy | |
| 60 | 1-methyl-cycloprop-1-yl | 4-methyl-phenyl | 2-(morpholin-4-yl)ethoxy | 146–8 |
| 61 | tert-butyl | 4-methyl-phenyl | 2-(morpholin-4-yl)ethoxy Ar$_2$ = 5,6,7,8-tetrahydronaphthalene | 99–100 |
| 62 | tert-butyl | 4-methyl-phenyl | 2-(trans-2,6-dimethyl-morpholin-4-yl)ethoxy | 137–139 |
| 63 | tert-butyl | 4-methyl-phenyl | 2-(cis-2,6-dimethyl-morpholin-4-yl)ethoxy | 153–154 |
| 64 | tert-butyl | 4-methyl-phenyl | 2-(2-methoxymethyl-morpholin-4-yl)ethoxy | 85–90 |
| 65 | tert-butyl | 4-methyl-phenyl | 2-(1-oxo-thiomorpholin-4-yl)ethoxy | 205–207 |
| 66 | tert-butyl | 4-methyl-phenyl | 2-(1-oxo-thiazolidin-3-yl)ethoxyl | 193–195 |
| 67 | tert-butyl | 4-methyl-phenyl | 5-methylamino-5-oxo-butyloxy | 117–119 |
| 68 | tert-butyl | 4-methyl-phenyl | 5-amino-5-oxo-butyloxy | foam |
| 69 | tert-butyl | 4-methyl-phenyl | 5-(morpholin-4-yl)-5-oxo-butyloxy | foam |
| 70 | tert-butyl | 2-methyl-pyridin-5-yl | pyridin-4-yl-thio | |

Assessment of Biological Properties

Inhibition of TNF Production in THP Cells

The inhibition of cytokine production can be observed by measuring inhibition of TNFα in lipopolysaccharide stimulated THP cells. All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was non-sterile. Initial stock solutions were made in DMSO followed by dilution into RPMI 1640 2-fold higher than the desired final assay concentration. Confluent THP.1 cells ($2 \times 10^6$ cells/ml, final conc.; American Type Culture Company, Rockville, Md.) were added to 96 well polypropylene round bottomed culture plates (Costar 3790; sterile) containing 125 μl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 μg/ml final; Siga L-2630, from E.coli serotype 0111.B4; stored as 1 μg/ml stock in endotoxin screened distilled H$_2$O at −80° C.). Blanks (unstimulated) received H$_2$O vehicle; final incubation volume was 250 μl. Overnight incubation (18–24 hr) proceeded as described above. Assay was terminated by centrifuging plates 5 min, room temperature, 1600 rpm (400 x g); supernatants were transferred to clean 96 well plates and stored −80° C. until analyzed for human TFNα by a commercially available ELISA kit (Biosource #KHC3015, Camarillo, Calif.). Data was analyzed by non-linear regression (Hill equation) to generate a dose response curve using SAS Software.

System (SAS institute, Inc., Cary, N.C.). The calculated IC50 value is the concentration of the test compound that caused a 50% decrease in the maximal TNFα production.

Representative compounds from the synthetic examples above and Table 1 were evaluated and all had IC$_{50}$<10 uM in this assay.

Inhibition of Other Cytokines

By similar methods using peripheral blood monocytic cells, appropriate stimuli, and commercially available ELISA kits for a particular cytokine, inhibition of IL-1, GM-CSF, IL-6 and IL-8 was demonstrated by representatives from the synthetic examples and Table 1.

All references cited in this application are incorporated herein in their entirety.

What is claimed is:

1. A compound selected from:

1-[5-(2-hydroxy-1,1-dimethyl-ethyl)-2-p-tolyl-2H-pyrazol-3-yl]-3-[4-(2-morpholin-4-yl-ethoxy)-naphthalen-1-yl]-urea;
1-[5-tert-butyl-2-(3-hydroxy-4-methyl-phenyl)-2H-pyrazol-3-yl]-3-[4-(2-morpholin-4-yl-ethoxy)-naphthalen-1-yl]-urea;
1-[5-tert-butyl-2-(4-hydroxymethyl-phenyl)-2H-pyrazol-3-yl]-3-[4-(2-morpholin-4-yl-ethoxy)-naphthalen-1-yl]-urea;
1-[5-tert-butyl-2-p-tolyl-2H-pyrazol-3-yl]-3-{4-[2-(3-oxo-morpholin-4-yl)-ethoxy]-naphthalen-1-yl}-urea;
1-[5-tert-butyl-2-p-tolyl-2H-pyrazol-3-yl]-3-{4-[2-(4-oxy-morpholin-4-yl)-ethoxy]-naphthalen-1-yl}-urea;
1-[5-(2-hydroxy-1,1-dimethyl-ethyl)-2-(6-methyl-pyridin-3-yl)-2H-pyrazol-3-yl]-3-[4-(2-morpholin-4-yl-ethoxy)-naphthalen-1-yl]-urea;
1-[5-tert-butyl)-2-(1-oxy-6-methyl-pyridin-3-yl)-2H-pyrazol-3-yl]-3-[4-(2-morpholin-4-yl-ethoxy)-naphthalen-1-yl]-urea;
1-[5-tert-butyl)-2-(6-methyl-pyridin-3-yl)-2H-pyrazol-3-yl]-3-{4-[2-(4-oxy-morpholin-4-yl)-ethoxy]-naphthalen-1-yl}-urea;
1-[5-(2-hydroxy-1,1-dimethyl-ethyl)-2-(6-methyl-pyridin-3-yl)-2H-pyrazol-3-yl]-3-[4-(2-pyridin-4-yl-ethoxy)-naphthalen-1-yl]-urea;
1-[5-tert-butyl)-2-(6-methyl-pyridin-3-yl)-2H-pyrazol-3-yl]-3-[4-(2-hydroxy-2-pyridin-4-yl-ethoxy)-naphthalen-1-yl]-urea;
1-[5-tert-butyl)-2-(6-methyl-pyridin-3-yl)-2H-pyrazol-3-yl]-3-{4-[2-(1-oxy-pyridin-4-yl)-ethoxy]-naphthalen-1-yl}-urea;
1-[5-(2-hydroxy-1,1-dimethyl-ethyl)-2-p-tolyl-2H-pyrazol-3-yl]-3-{4-[2-(1-oxo-thiomorpholin-4-yl)-ethoxy]-naphthalen-1-yl}-urea;
1-[5-tert-butyl-2-(4-hydroxymethyl-phenyl)-2H-pyrazol-3-yl]-3-{4-[2-(1-oxo-thiomorpholin-4-yl)-ethoxy]-naphthalen-1-yl}-urea;
1-[5-tert-butyl-2-p-tolyl-2H-pyrazol-3-yl]-3-{4-[2-(1,3 dioxo-thiomorpholin-4-yl)-ethoxy]-naphthalen-1-yl}-urea;
1-[5-(2-hydroxy-1,1-dimethyl-ethyl)-2-methyl-2H-pyrazol-3-yl]-3-[4-(2-morpholin-4-yl-ethoxy)-naphthalen-1-yl]-urea and
1-[5-tert-butyl-2-methyl-2H-pyrazol-3-yl]-3-{4-[2-(4-oxy-morpholin-4-yl)-ethoxy]-naphthalen-1-yl}-urea or physiologically acceptable acids or salts thereof.

2. A compound selected from:

1-[5-tert-Butyl-2-(2-hydroxy-4-methyl-phenyl)-2H-pyrazol-3-yl]-3-[4-(2-morpholin-4-yl-ethoxy)-naphthalen-1-yl]-urea;
4-(3-tert-Butyl-5-{3-[4-(2-morpholin-4-yl-ethoxy)-naphthalen-1-yl]-ureido}-pyrazol-1-yl)-benzoic acid;
1-[5-(1,1-Dimethyl-2-oxo-ethyl)-2-p-tolyl-2H-pyrazol-3-yl]-3-[4-(2-morpholin-4-yl-ethoxy)-naphthalen-1-yl]-urea;
2-Methyl-2-(5-{3-[4-(2-morpholin-4-yl-ethoxy)-naphthalen-1-yl]-ureido}-1-p-tolyl-1H-pyrazol-3-yl)-propionic acid;
1-(5-tert-Butyl-2-p-tolyl-2H-pyrazol-3-yl)-3-[4-(2-morpholin-4-yl-2-oxo-ethoxy)-naphthalen-1-yl]-urea and
1-(5-tert-Butyl-2-p-tolyl-2H-pyrazol-3-yl)-3-{4-[2-(1-oxo-1$\lambda^4$-thiomorpholin-4-yl)-ethoxy]-naphthalen-1-yl}-urea or physiologically acceptable acids or salts thereof.

3. A method of treating a cytokine mediated disease or condition selected from rheumatoid arthritis, multiple sclerosis, Guillain-Barre syndrome, Crohn's disease, ulcerative colitis, psoriasis, graft versus host disease, systemic lupus erythematosus and insulin-dependent diabetes mellitus, toxic shock syndrome, osteoarthritis, diabetes, inflammatory bowel diseases, acute and chronic pain, contact dermatitis, atherosclerosis, glomerulonephritis, reperfusion injury, bone resorption diseases, asthlna, stroke, myocardial infarction, thermal injury, adult respiratory distress syndrome (ARDS), multiple organ injury secondary to trauma, dermatoses with acute inflammatory components, acute purulent meningitis, necrotizing entrerocolitis, syndromes associated with hemodialysis, septic shock, leukopherisis and granulocyte transfusion comprising administering to a patient in need of such treatment a therapeutically effective amount of a compound according to claims 1 or 2.

4. The method according to claim 3 wherein the cytokine mediated disease or condition is selected from rheumatoid arthritis, Crohn's disease and psoriasis.

5. A method of treating a cytokine mediated disease or condition selected from restenosis following percutaneous transluminal coronary angioplasty, Alzheimer's disease, chronic obstructive pulmonary disease and congestive heart failure comprising administering to a patient in need of such treatment a therapeutically effective amount of a compound according to claims 1 or 2.

6. A pharmaceutical composition comprising a compound according to claims 1 or 2 and one or more pharmaceutically acceptable adjuvants and/or carriers.

* * * * *